(12) United States Patent
Laine et al.

(10) Patent No.: US 7,868,198 B2
(45) Date of Patent: Jan. 11, 2011

(54) MULTI-FUNCTIONAL SILSESQUIOXANES FOR NOVEL COATING APPLICATIONS

(76) Inventors: Richard M. Laine, 1375 Folkstone Ct., Ann Arbor, MI (US) 48105; Vera Popova, 7020 Berwick Ct., Ypsilanti, MI (US) 48197; Daniel W. Bartz, 771 Valley Circle Dr., Saline, MI (US) 48176; David J. Krug, III, 2884 Hawks Ave., Ann Arbor, MI (US) 48108; Michael Z. Asuncion, 555 E. William #12B, Ann Arbor, MI (US) 48104

( * ) Notice: Subject to any disclaimer, the term of this patent is extended or adjusted under 35 U.S.C. 154(b) by 74 days.

(21) Appl. No.: 12/156,643

(22) Filed: Jun. 3, 2008

(65) Prior Publication Data

US 2009/0012317 A1   Jan. 8, 2009

Related U.S. Application Data

(60) Provisional application No. 60/944,115, filed on Jun. 15, 2007, provisional application No. 61/058,117, filed on Jun. 3, 2008.

(51) Int. Cl.
    C07F 7/02      (2006.01)
    C04B 41/50     (2006.01)
(52) U.S. Cl. ................. 556/460; 549/215; 106/287.1
(58) Field of Classification Search ............... 556/460; 106/287.1; 549/215, 287.1
    See application file for complete search history.

(56) References Cited

U.S. PATENT DOCUMENTS

| 5,039,771 | A | 8/1991 | Morimoto et al. |
| 5,047,492 | A | 9/1991 | Weidner et al. |
| 5,330,734 | A | 7/1994 | Johnson et al. |
| 6,100,417 | A | 8/2000 | Lichtenhan et al. |
| 6,207,364 | B1 | 3/2001 | Takamuki et al. |
| 6,329,490 | B1 * | 12/2001 | Yamashita et al. ............ 528/42 |
| 6,770,724 | B1 | 8/2004 | Lichtenhan et al. |
| 6,927,301 | B2 | 8/2005 | Laine et al. |

(Continued)

FOREIGN PATENT DOCUMENTS

EP    0736584 A2    10/1996

(Continued)

OTHER PUBLICATIONS

S. Sulaiman, C.M. Brick, C.M. De Sana, J.M. Katzenstein, R.M. Laine, R.A. Basheer,"Tailoring the Global Properties of Nanocomposites. Epoxy Resins with Very Low Coefficients of Thermal Expansion," Macromolecules 39 5167-9 (2006).

(Continued)

*Primary Examiner*—Porfirio Nazario Gonzalez
(74) *Attorney, Agent, or Firm*—Kubotera & Associates, LLC

(57) ABSTRACT

A multi-functional silsesquioxane, method of making the same, and coatings incorporating the same, including a polyhedral silsesquioxane including at least one first face and at least one second face that is spaced apart from the at least one first face; at least one first functionality bonded to the at least one first face; and at least one second functionality different from the first functionality, and being bonded to the at least one second face. In one particular respect, silica for the silsesquioxane may be derived from rice hull ash via an octa(tetramethylammonium)silsesquioxane octaanion.

16 Claims, 37 Drawing Sheets

U.S. PATENT DOCUMENTS

| | | | |
|---|---|---|---|
| 7,256,243 | B2 | 8/2007 | Oikawa et al. |
| 2002/0090572 | A1 | 7/2002 | Sooriyakumaran et al. |
| 2003/0120099 | A1 | 6/2003 | Laine et al. |
| 2005/0033077 | A1 | 2/2005 | Yamahiro et al. |
| 2005/0142054 | A1 | 6/2005 | Hasegawa et al. |
| 2006/0040103 | A1 | 2/2006 | Whiteford et al. |
| 2006/0083925 | A1 | 4/2006 | Laine et al. |
| 2006/0122351 | A1 | 6/2006 | Laine et al. |
| 2007/0045619 | A1 | 3/2007 | Park et al. |

FOREIGN PATENT DOCUMENTS

| | | |
|---|---|---|
| EP | 0736584 A3 | 10/1996 |
| WO | 02-100867 A | 12/2002 |
| WO | 03-102695 A1 | 12/2003 |
| WO | 2004-038769 A | 6/2004 |
| WO | 2006-132656 A | 12/2006 |

OTHER PUBLICATIONS

M. Z. Asuncion, R.M. Laine, "Silsesquioxane Barrier Materials," Macromolecules 40, 555-562 (2007).

http://www.mayaterials.com/html/coatings.html (last accessed Jun. 15, 2007).

C. Brick, E. R. Chan, S.C. Glotzer, D.C. Martin, R.M. Laine, "Self-lubricating nano ball bearings," Adv. Mater. 19 82-9 (2007).

R. M. Laine, J. Choi, I. Lee, "Organic-Inorganic Nanocomposites with Completely Defined Interfacial Interactions," Adv. Mater. 13, 800-3 (2001).

C. Zhang, T.J. Bunning, R.M. Laine, "Synthesis and Characterization of Liquid Crystalline (LC) Silsesquioxanes," Chem. of Mater.; 13; 3653-62 (2001).

J. Choi, J. Harcup, A.F. Yee, Q. Zhu, R.M. Laine, "Organic/inorganic hybrid composites from cubic silsesquioxanes," J. Am. Chem. Soc. 123, 11420-30 (2001).

R. Tamaki, Y. Tanaka, M. Z. Asuncion, J. Choi, R.M. Laine, "Octa(aminophenyl)silsesquioxane as a Nanoconstruction Site," J. Am. Chem. Soc. 123, 12416-7 (2001).

R. Tamaki, J. Choi, R.M. Laine "A Polyimide Nanocomposite from Octa(aminophenyl)-silsesquioxane" Chem. Materials 15, 793-7 (2003).

J. Choi, R. Tamaki, S.G. Kim, R.M. Laine, "Organic/Inorganic Imide Nanocomposites from Aminophenylsilsesquioxanes," Chem. Mater. 15 3365-3375 (2003).

J. Choi, Albert F. Yee, and Richard M. Laine, "Organic/Inorganic Hybrid Composites from Cubic Silsesquioxanes. Epoxy Resins of Octa(dimethylsiloxy-ethylcyclohexylepoxide) Silsesquioxane," Macromolecules 36, 5666-82 (2003).

J. Choi, A.F. Yee, R.M. Laine, "Toughening of cubic silsesquioxane epoxy nanocomposites using core shell rubber particles; a three component hybrid system," Macromol. 37, 3267-76 (2004).

M.Z. Asuncion, I. Hasegawa, J. Kampf, R.M. Laine, "The selective dissolution of rice hull ash to form $[OSiO_{1.5}]_8[R_4N]_8$ (R=Me, $CH_2CH_2OH$) octasilicates. Basic nanobuilding blocks and possible models of intermediates formed during biosilification processes," Materials Chemistry 15, 2114-21 (2005).

R.M. Laine, "Nano-building blocks based on the $[OSiO_{1.5}]_8$ silsesquioxanes," J. Mater. Chem., 15, 3725-44 (2005).

N. Takamura, L. Viculis, R.M. Laine "A completely discontinuous organic/inorganic hybrid nanocomposite based on reactions of $[HMe_2SiOSiO_{1.5}]_8$ with vinylcyclohexene," International Polymers Journal web published Apr. 16, 2007.

A.R. Bassindale, H. Chen, Z. Liu, I. A. MacKinnon, D. J. Parker, P. G. Taylor, Y. Yang, M. E. Light, P. N. Norton, M. B. Hursthouse, *J. Organomet. Chem.* 2004, 689, 3287.

A. Sellinger, R.M. Laine, "Silsesquioxanes as Synthetic Platforms. Thermally and Photo Curable Inorganic/Organic Hybrids," Macromol. 29, 2327-30 (1996).

H.W. Ro, K. Char, E-C. Jeon, H-J. Kim, K. Kwon, H-J. Lee, J-K. Lee, H-W Rhee, C.L. Soles, D.Y. Yoon, "High Modulus Spin-On Organosilicates for Nanoporous Glasses," Adv. Mater. 19 705-710 (2007).

Liu Zhi—hua, Alan R. Bassindale and Peter G. Taylor, "Synthesis of SilsesquiOxane Cages from Phenyl-cis-tetrol, 1,3-DiVinyltetraethoxydisilOxane and Cyclopentyl Resins," Chem. Res. Chinese U., 20(4), 433-436 (2004).

J. Chojnowskli, W. Fortuniak, P. Ros' ciszewski, W. Werel, J. Łukasiak, W. Kamysz, R. Hałasa, Biocidal Polysilsesquioxanes: "Polysilsesquioxanes and Oligosilsesquioxanes Sub-stituted by Alkylammonium Salts as Antibacterial Biocides" J. Inorganic and Organometallic Poly. and Mater., 16, 219 (2006).

S.P. Denyer, "Mechanisms of Action of Antibacterial Biocides," International Biodeterioration & Biodegradation (1995) 221-245.

Alan R. Bassindale, Zhihua Liu, Iain A. MacKinnon, Peter G. Taylor, Yuxing Yang, Mark E. Light, Peter N. Horton and Michael B. Hursthouse, "A higher yielding route for $T_8$ silsesquioxane cages and X-ray crystal structures of some novel spherosilicates," Dalton Trans., 2945-2949 (2003).

O. Shchegolikhina, Y. Pozdniakova, M. Antipin, D. Katsoulis, N. Auner, B. Herrschaft, "Synthesis and Structure of Sodium Phenylsiloxanolates," Organometallics, 19, 1077-82 (2000).

K.A. Andrianov, V.S. Tikhonov, G.P. Makhneva, G.S. Chernov, "Synthesis of Polycyclic Tetramethyltetraphenylcyclooctasilsesesquioxane," Izvestiya Akademii Nauk SSSR, Seriya Khimicheskaya, 4, 956-957 (1973).

A. Sellinger, R.M. Laine, "Silsesquioxanes as Synthetic Platforms. III. Photocurable, Liquid Epoxides as Inorganic/Organic Hybrid Precursors," Chem. Mater. 8, 1592-3 (1996).

R. M. Laine, M. Roll, M. Asuncion, S. Sulaiman, V. Popova, D. Bartz, D. J. Krug, P. H. Mutin, "Perfect and nearly perfect silsesquioxane (SQs) nanoconstruction sites and Janus SQs," Journal of Sol-Gel Science and Technology, 46, 335-347 (2008).

M.G. Voronkov et al., "Polyhedral Oligosilsesquioxanes and their Homo Derivatives", Top. Curr. Chem., 102, 199-236 (1982).

R.Q. Su, T.E. Muller, J. Prochazka, J.A. Lercher, "A New Type of Low-k Dielectric Films Based on Polysilsesquioxanes," Adv. Mater. 14, 1369-73 (2002).

K. Takahashi, S. Sulaiman, J. Katzenstein, S. Snoblen, R. Laine, "New Aminophenylsilsesquioxanes—Synthesis, Properties and Epoxy Nanocomposites", Aust. J. Chem., 59, 564-570 (2006).

C. Zhang, F. Babonneau, C. Bonhomme, R. Laine, C. Soles, H. Hristov, A. Yee, "Highly Porous Polyhedral Silsesquioxane Polymers. Synthesis and Characterization," J. Am. Chem. Soc. ,120, 8380-8391 (1998).

J. Choi, J. Harcup, A.Yee, Q. Zhu, R. Laine, "Organic/Inorganic Hybrid Composites from Cubic Silsesquioxanes," J. Am. Chem. Soc., 123, 11420-11430 (2001).

S.G. Kim, J. Choi, R. Tamaki, Richard M. Laine, "Synthesis of amino-containing oligophenylsilsesquioxanes," Polymer, 46, 4514-4524, (2005).

Jiwon Choi, Seung Gyoo Kim, and Richard M. Laine, "Organic/Inorganic Hybrid Epoxy Nanocomposites from Aminophenylsilsesquioxanes," Macromolecules, 37, 99-109 (2004).

Dr. Orlin Velev, "2-faced" particles act like tiny submarines, http://www.eurekalert.org/pub_releases/2008-02/ncsu-pa022708.php.

T. Tashiro, "Antibacterial and Bacterium Adsorbing Macromolecules," Macromol. Mater. Eng. 286, 63-87 (2001).

\* cited by examiner

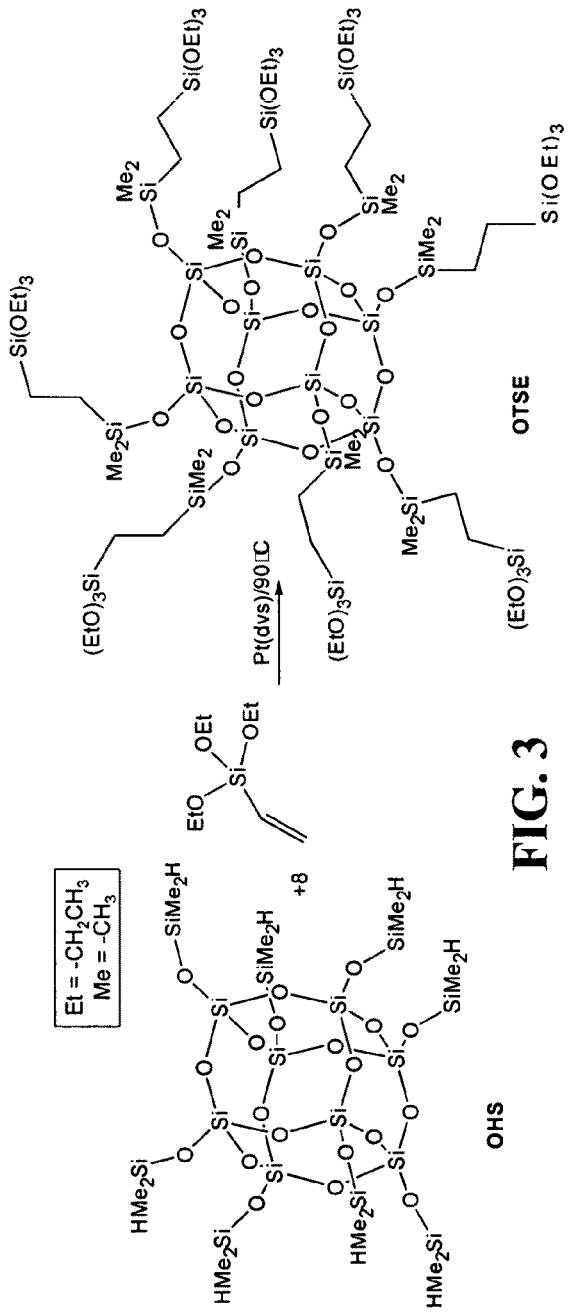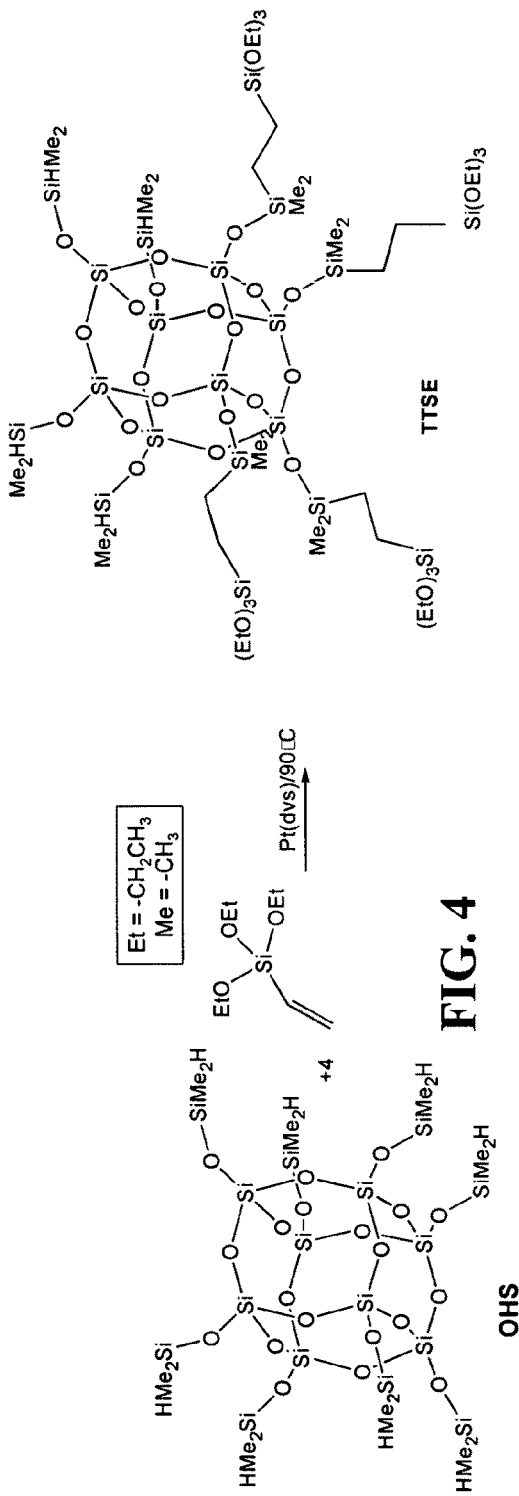
FIG. 3
FIG. 4

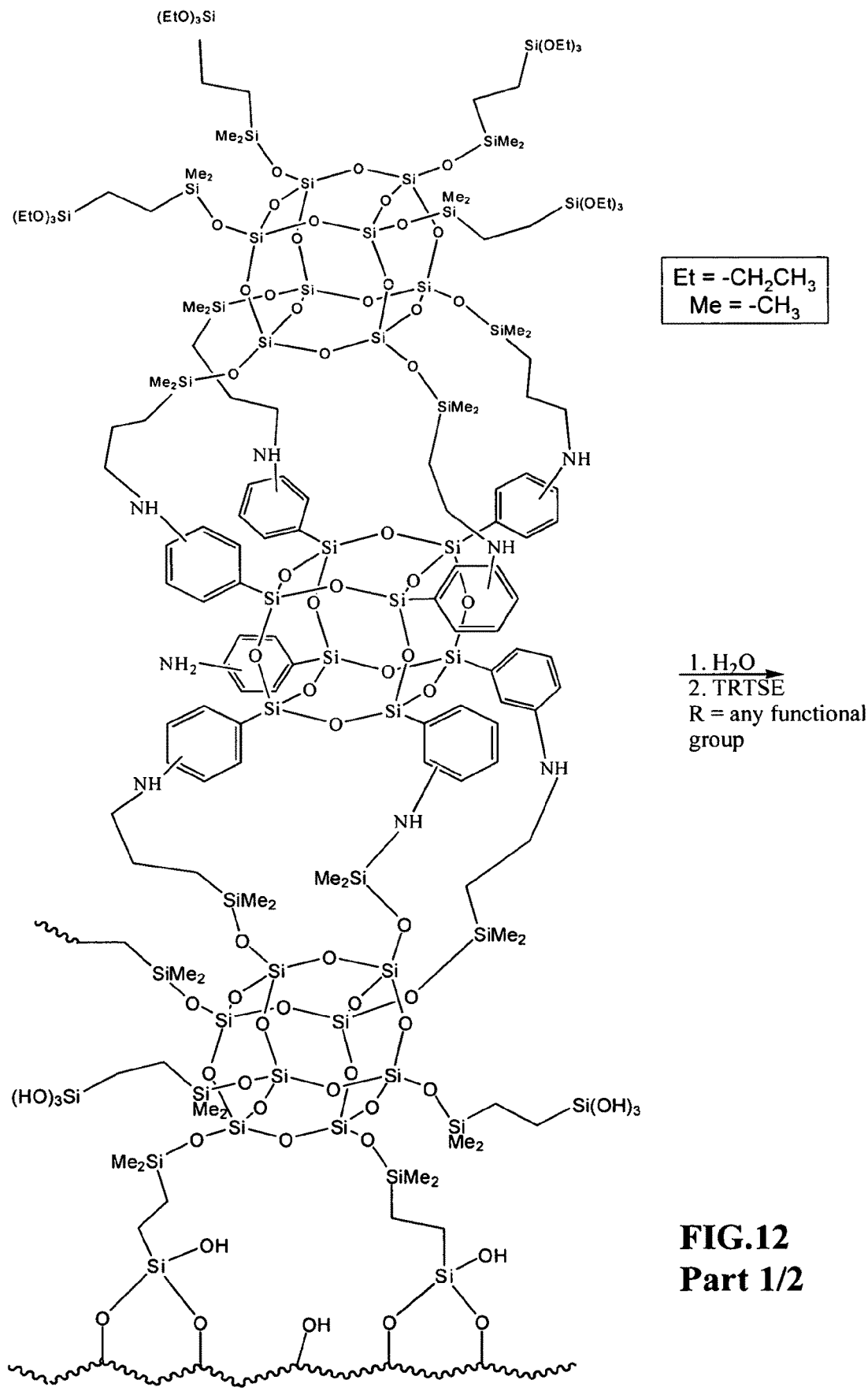
Et = -CH₂CH₃
Me = -CH₃
1. H₂O
2. TRTSE
R = any functional group
FIG. 12 Part 1/2

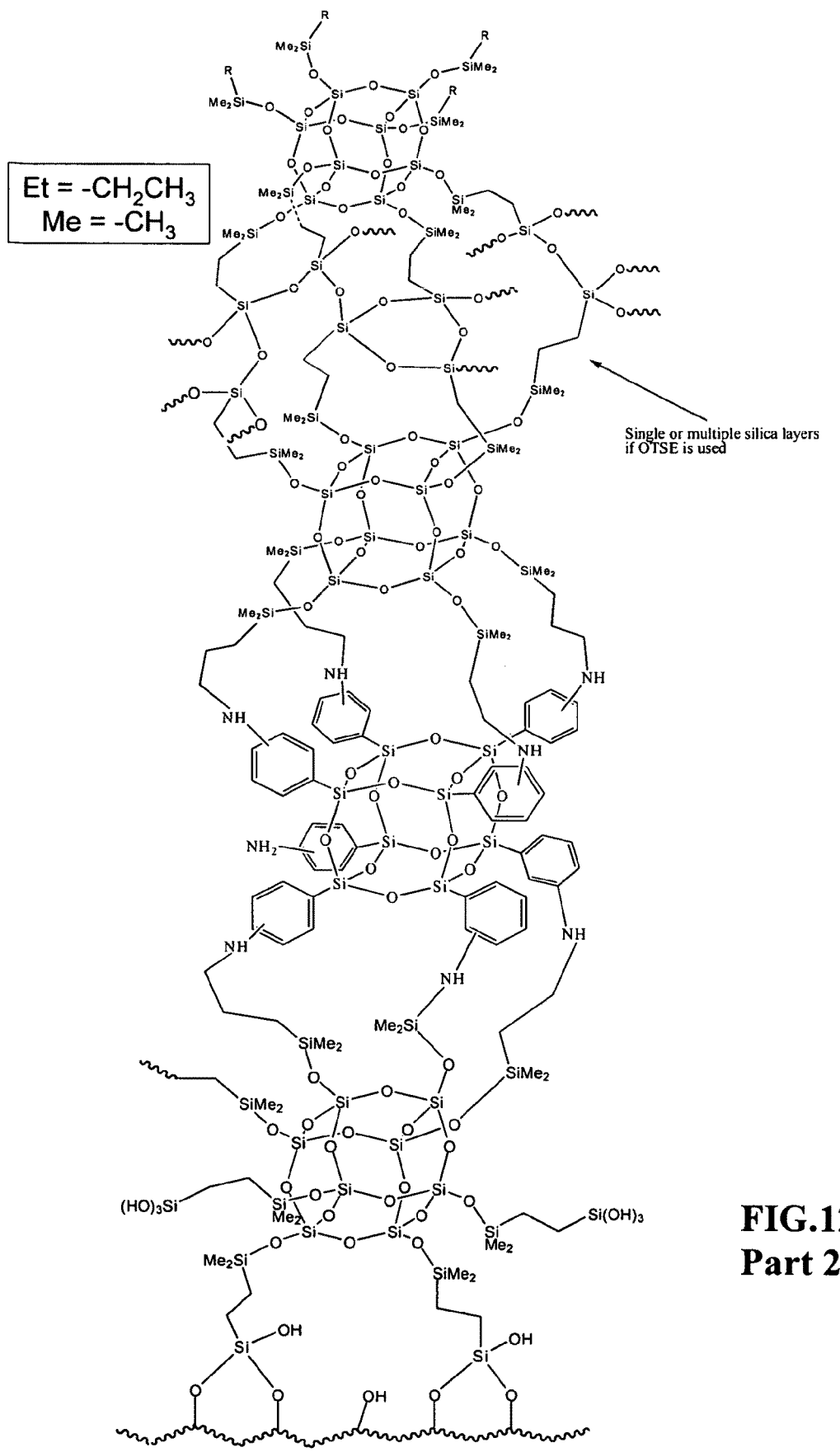
FIG.12 Part 2/2

a
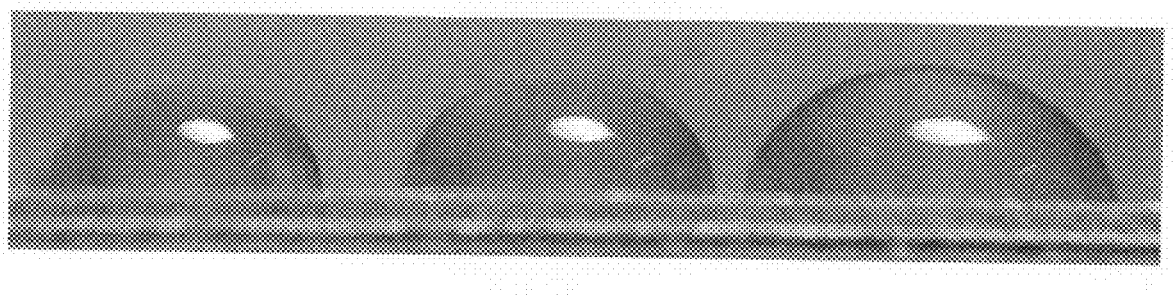
b
FIG. 18

Blank TCPTSE, ~90°

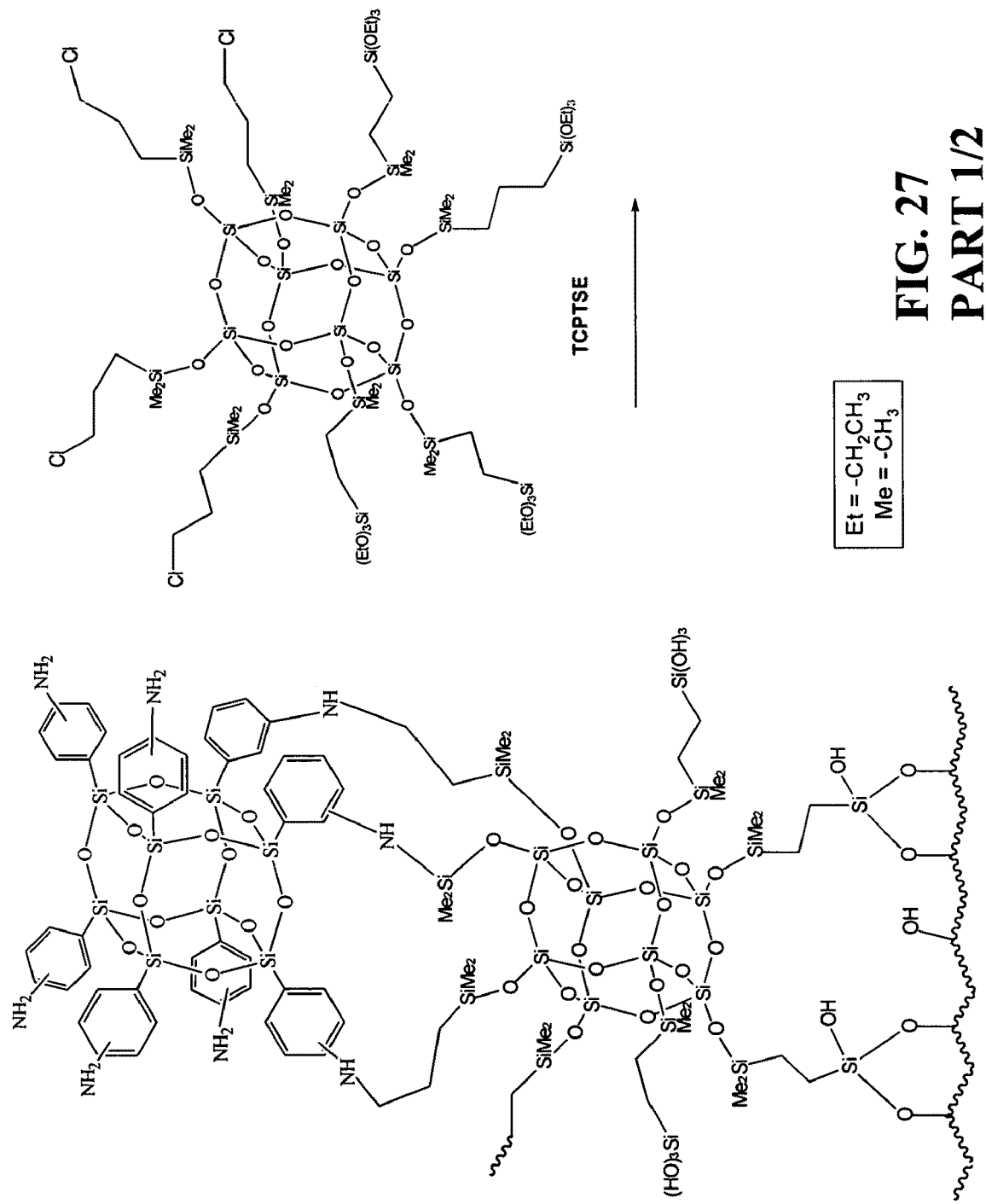
FIG. 27 PART 1/2

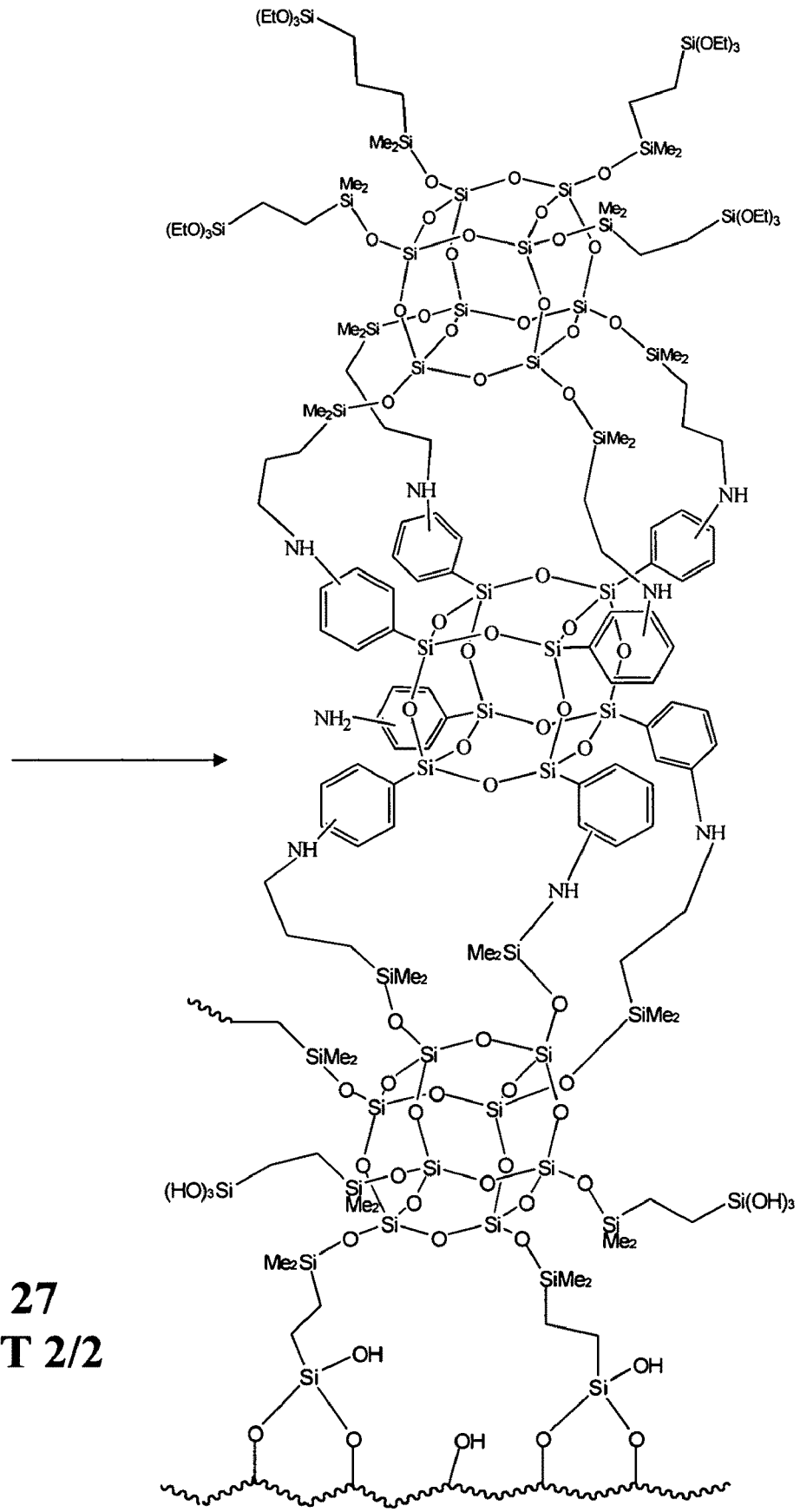
FIG. 27 PART 2/2

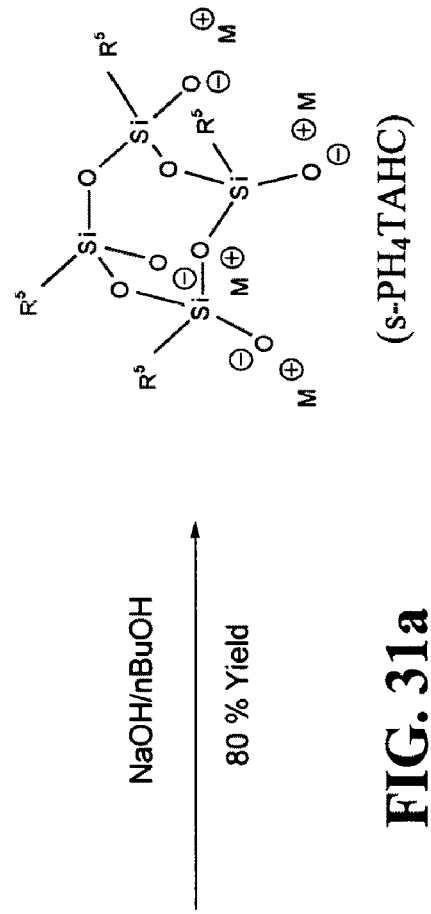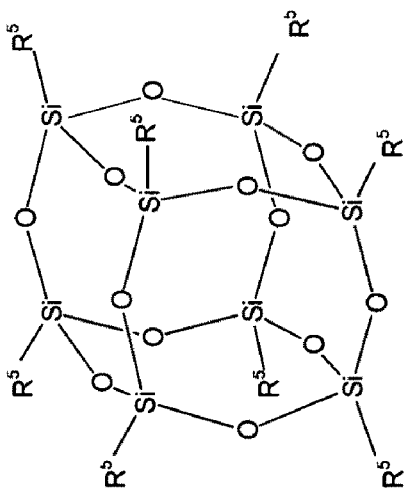
FIG. 31a
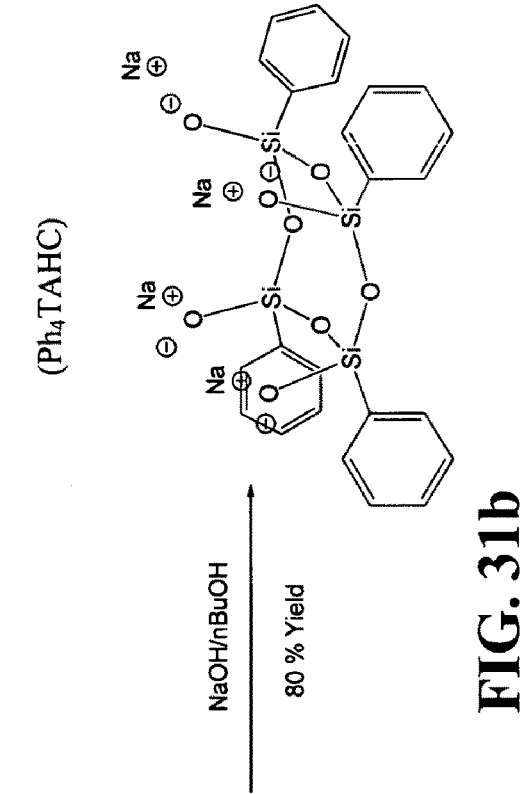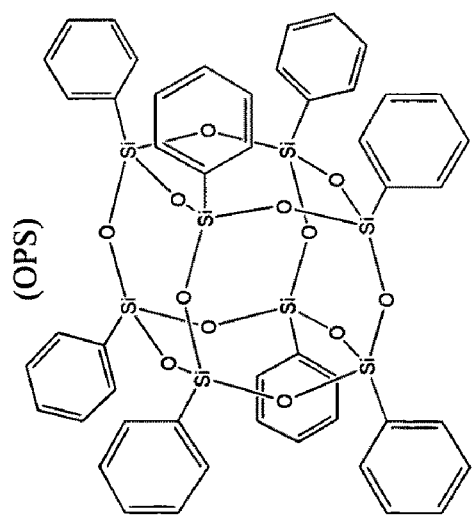
FIG. 31b

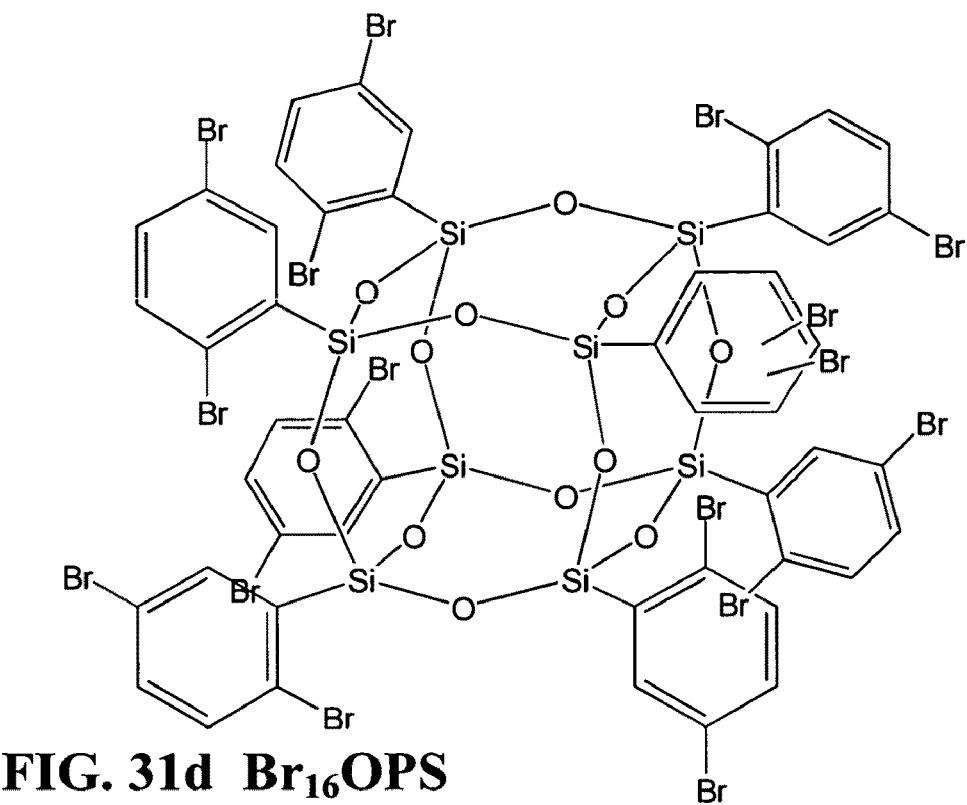
FIG. 31d Br₁₆OPS
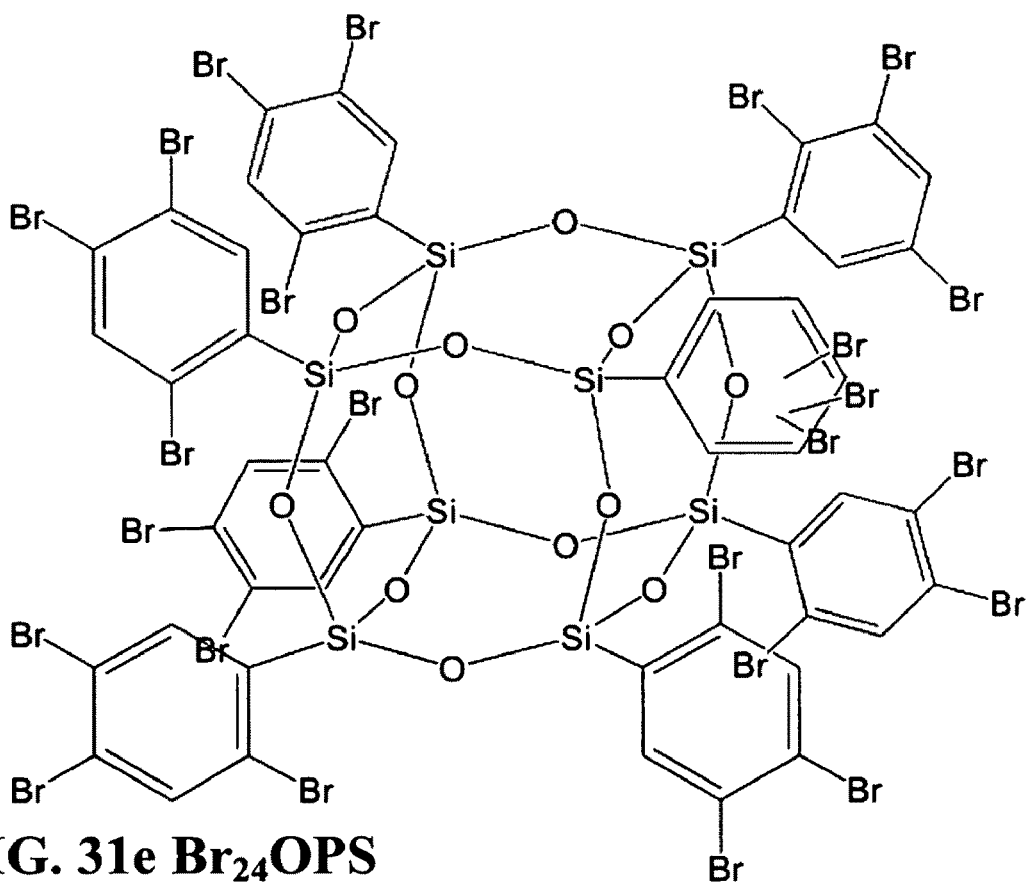
FIG. 31e Br₂₄OPS

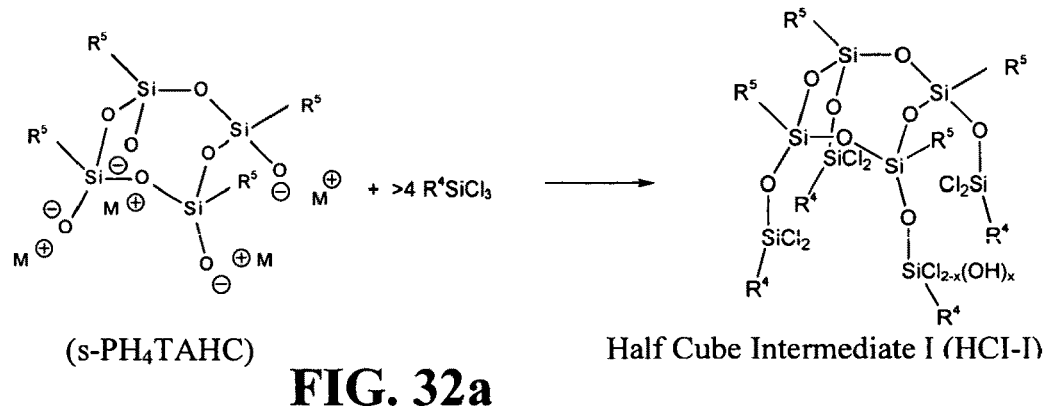
(s-PH4TAHC)    Half Cube Intermediate I (HCI-I)
FIG. 32a
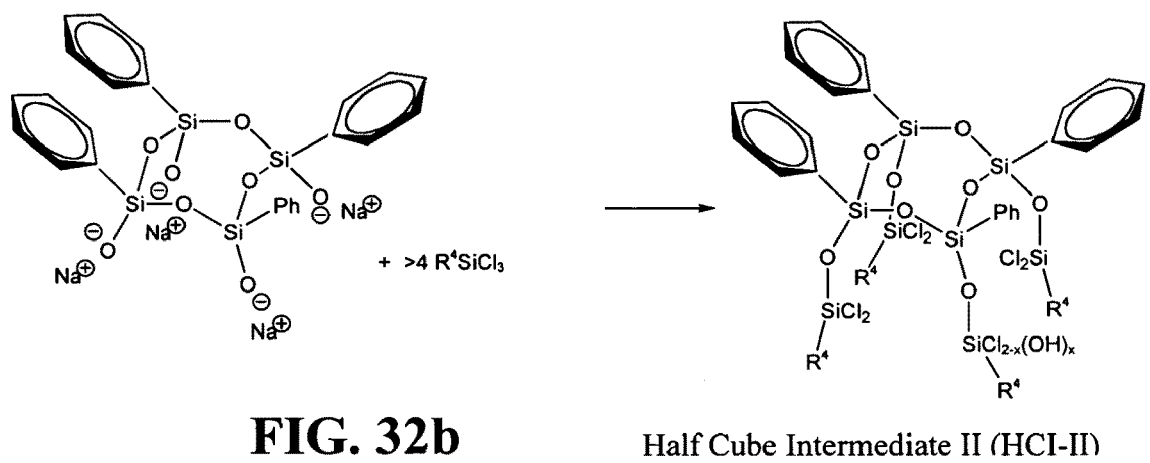
FIG. 32b    Half Cube Intermediate II (HCI-II)
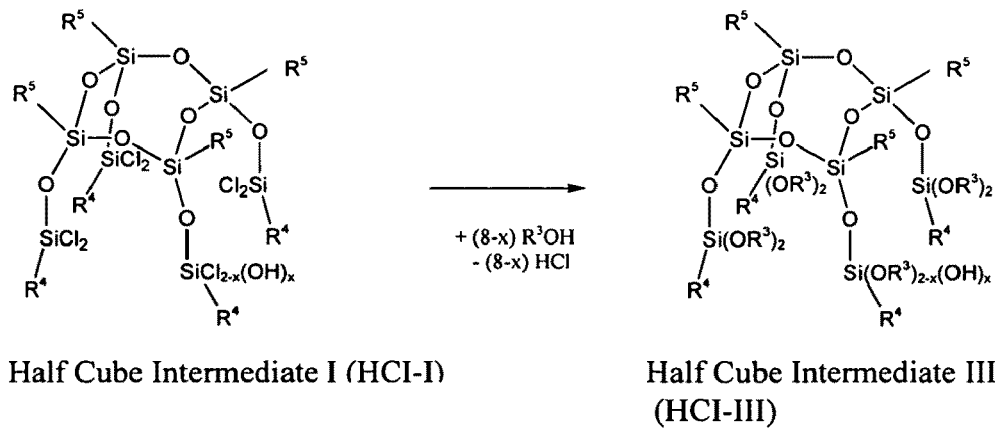
Half Cube Intermediate I (HCI-I)    Half Cube Intermediate III (HCI-III)
FIG. 33

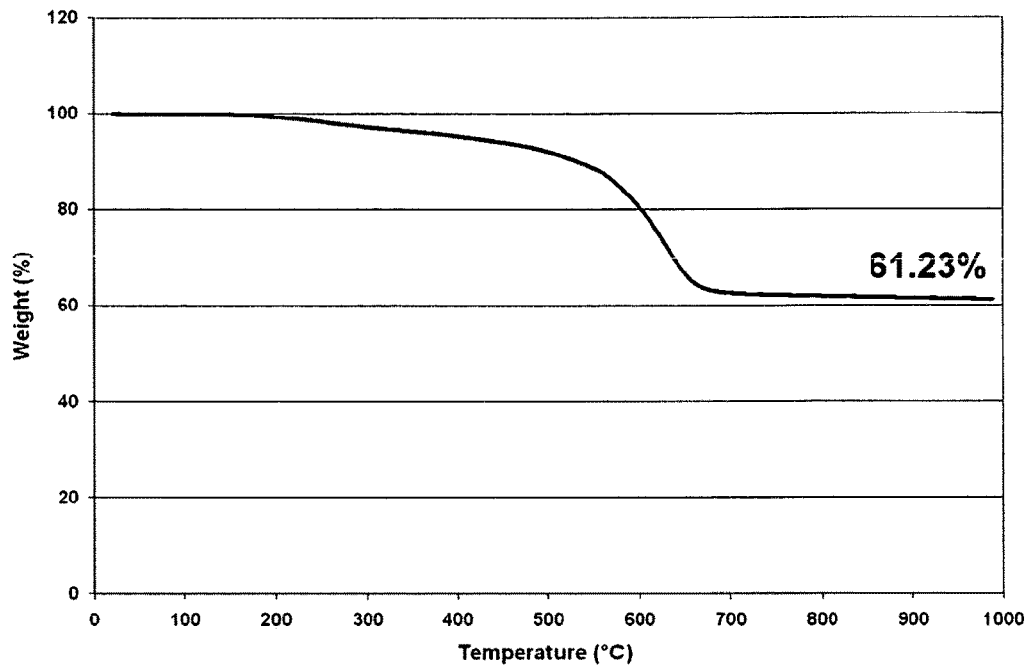
FIG. 36a. TGA (air) of Me$_4$Ph$_4$[Si$_8$O$_{12}$]. Theoretical ceramic yield is 61.21 and measured yield is 61.23.
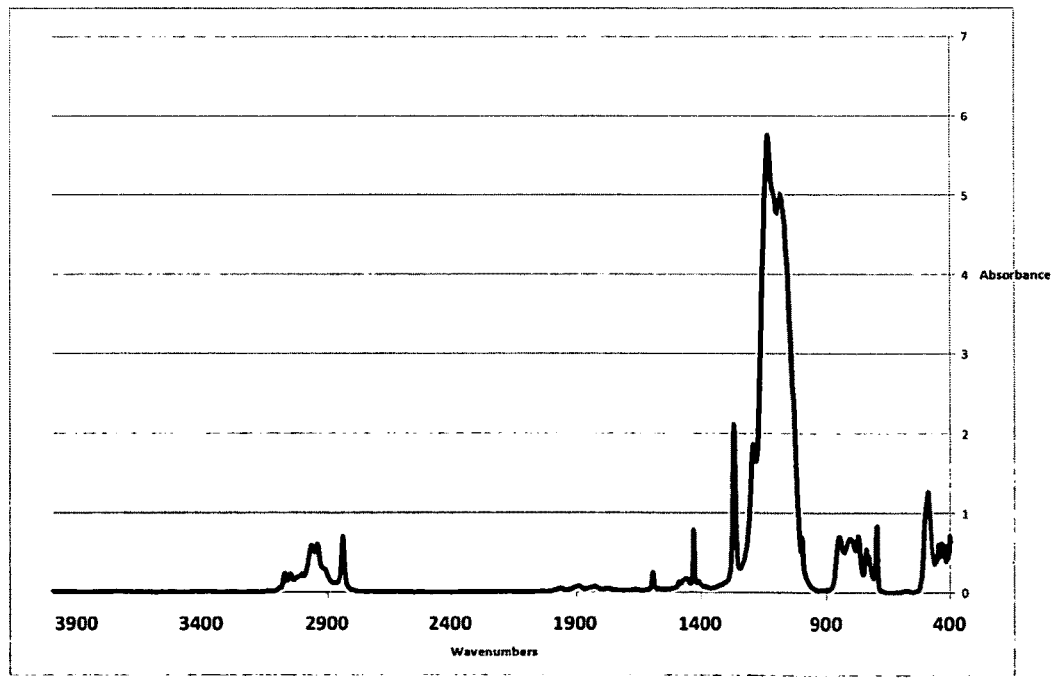
FIG. 36b. FTIR of Me4Ph$_4$[Si8O$_{12}$].

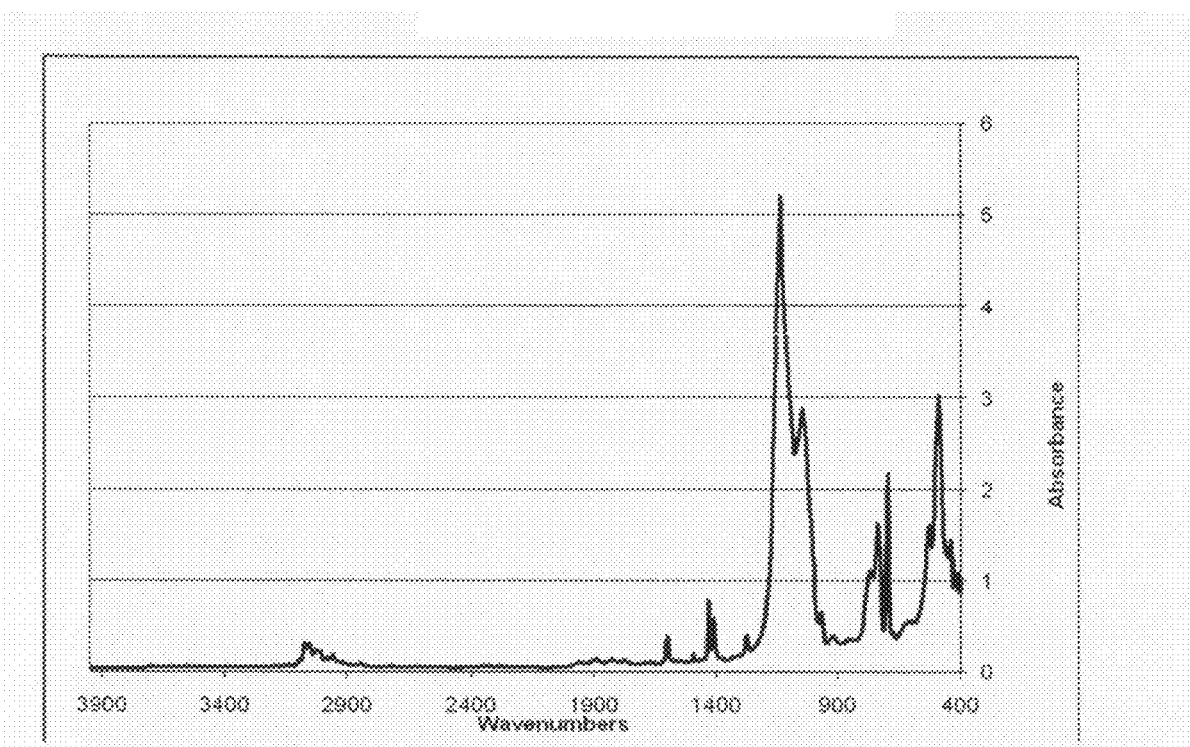
Fig. 37a. FTIR of Vinyl₄Ph₄ cubic silsesquioxane
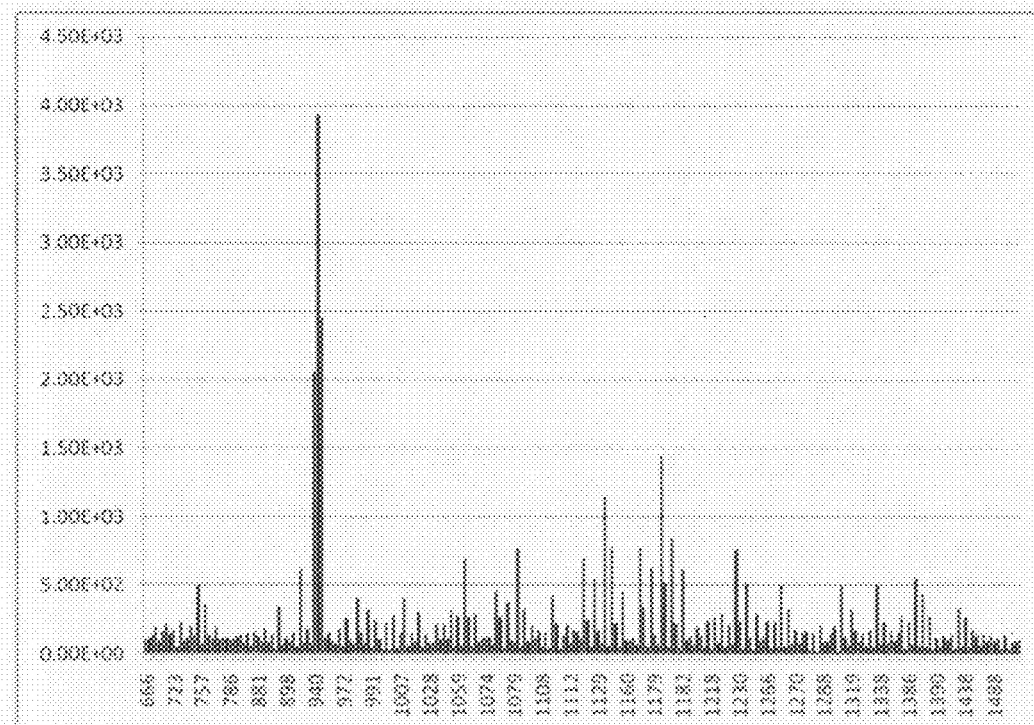
Fig. 37b. MALDI of Vinyl₄Ph₄[Si₈O₁₂] showing the expected MW at 941 Da.

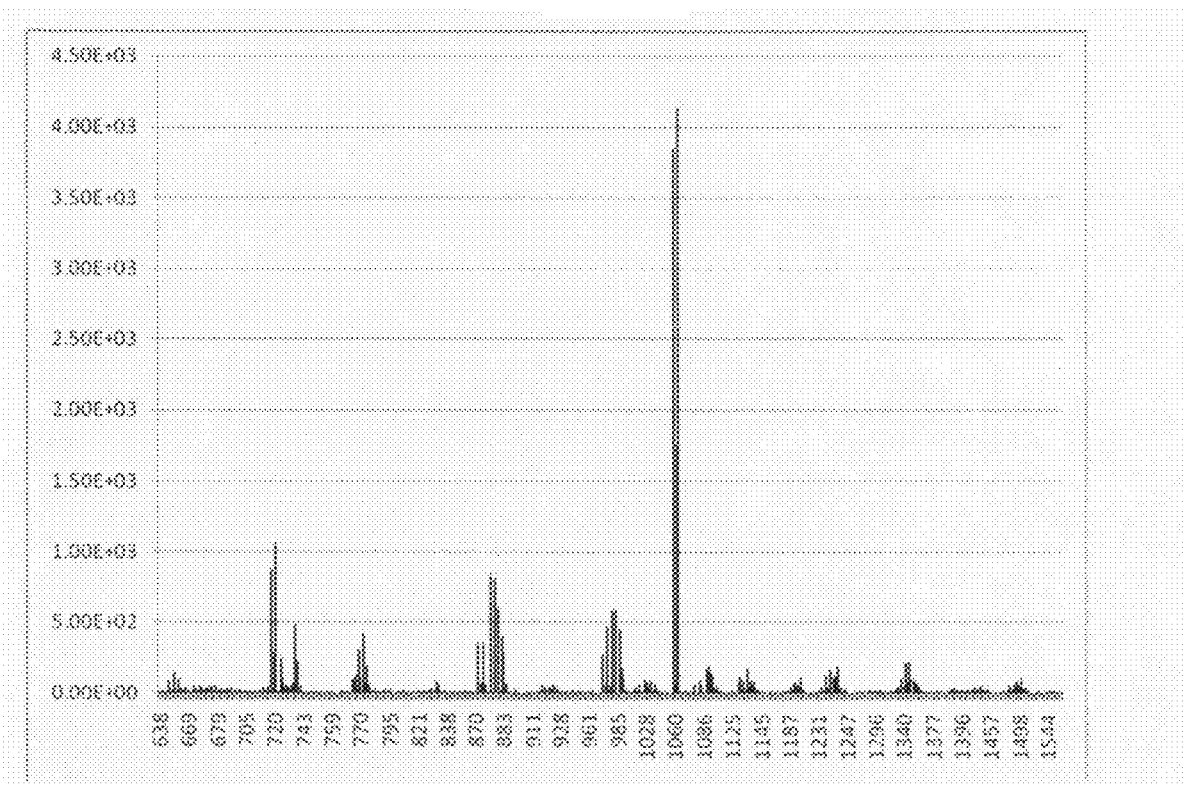
Fig. 38 MALDI of iBu$_4$Ph$_4$[Si$_8$O$_{12}$]. Expected MW=1061 Da.
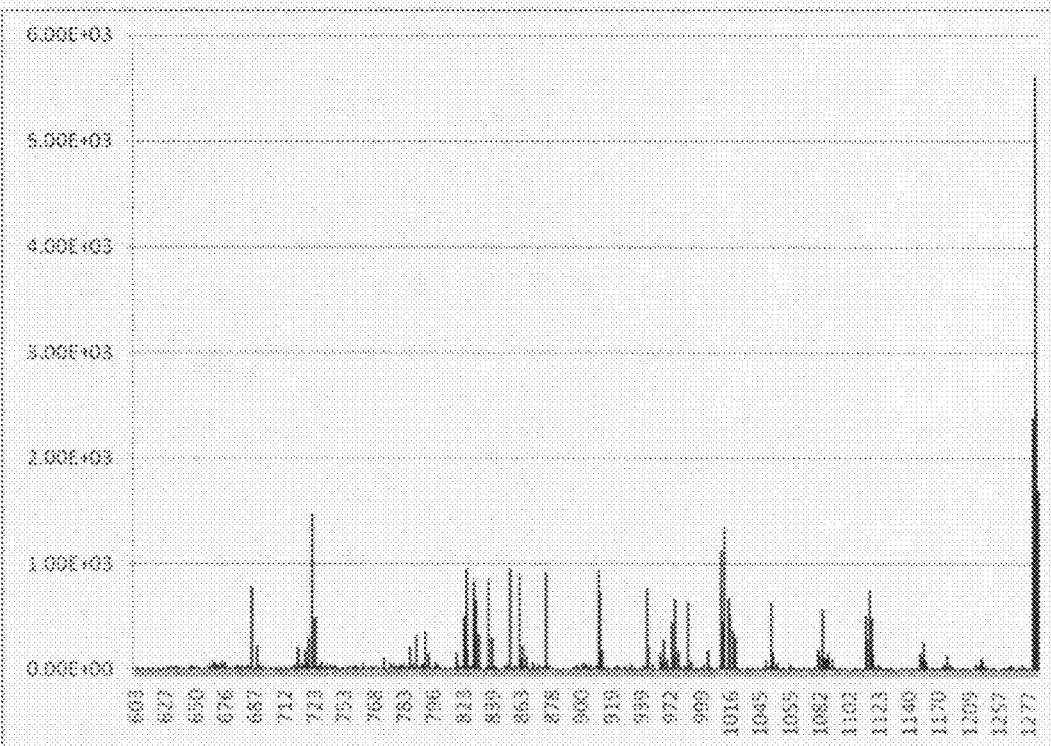
Fig. 39 MALDI of Octyl$_4$Ph$_4$[Si$_8$O$_{12}$]. Expected MW=1285 Da.

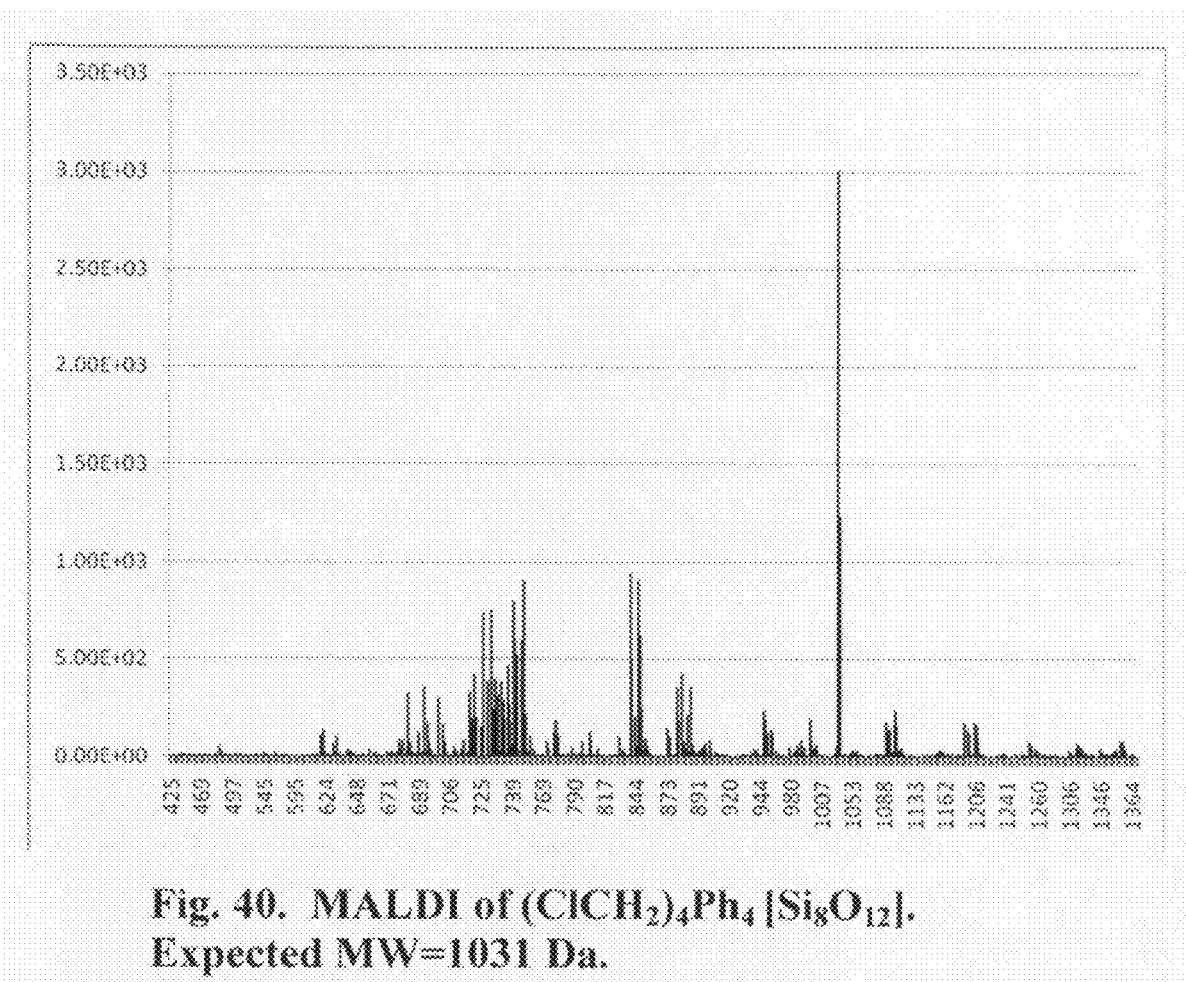
Fig. 40. MALDI of $(ClCH_2)_4Ph_4[Si_8O_{12}]$.
Expected MW=1031 Da.

MULTI-FUNCTIONAL SILSESQUIOXANES FOR NOVEL COATING APPLICATIONS

CROSS REFERENCE TO RELATED PATENT APPLICATIONS

This patent application claims the benefit of U.S. Provisional Patent Application Nos. 60/944,115 filed Jun. 15, 2007 and 61/058,117 filed on Jun. 3, 2008, and of PCT Patent Application No. PCT/US08/65554 filed on Jun. 2, 2008, which are each hereby incorporated by reference for all purposes.

GOVERNMENT RIGHTS

This invention was made in part with United States of America Government support under United States Air Force contract FA8650-05-C-5046. The United States Government has certain rights in this invention.

FIELD OF THE INVENTION

The present invention pertains to silsesquioxanes, and more particularly to multi-functional silsesquioxanes, such as derived using silica from rice hull ash.

BACKGROUND OF THE INVENTION

Silsesquioxanes (SQs) are unique molecules that can offer cubic symmetry (cubes) such that each functional group occupies a different octant in Cartesian space with typical diameters of about 1 nm. As such, they offer the opportunity to build nanocomposite/hybrid materials in 1-, 2- or 3-D, effectively one nanometer at a time. Furthermore the core adds the rigidity and heat capacity of silica making these compounds quite robust. In principle, the ability to assemble "cubes" on a nanometer by nanometer basis offers the potential to tailor materials properties (e.g. tailor materials properties) at nanometer length scales. Tailoring at such length scales should permit full optimization of global properties on an application-by-application basis and at relatively low cost. It can also aid in obtaining high reproducibility, predictability and therefore effective materials design. Information about the above can be gleaned from one or more of the following references, all of which are hereby incorporated by reference for all purposes:

1. S. Sulaiman, C. M. Brick, C. M. De Sana, J. M. Katzenstein, R. M. Laine, R. A. Basheer," Tailoring the Global Properties of Nanocomposites. Epoxy Resins with Very Low Coefficients of Thermal Expansion," Macromolecules 39 5167-9 (2006);
2. M. Z. Asuncion, R. M. Laine, "Silsesquioxane Barrier Materials," Macromolecules in press January (2007);
3. http://www.mavaterials.com/html/coatings.html (as accessed Jun. 15, 2007);
4. C. Brick, E. R. Chan, S. C. Glotzer, D. C. Martin, R. M. Laine, "Self-lubricating nano ball bearings," Adv. Mater. 19 82-9 (2007);
5. R. M. Laine, J. Choi, I. Lee, "Organic-inorganic Nanocomposites with Completely Defined Interfacial Interactions," Adv. Mater. 13, 800-3 (2001);
6. C. Zhang, T. J. Bunning, R. M. Laine, "Synthesis and Characterization of Liquid Crystalline (LC) Silsesquioxanes," Chem. of Mater.; 13; 3653-62 (2001);
7. J. Choi, J. Harcup, A. F. Yee, Q. Zhu, R. M. Laine, "Organic/inorganic hybrid composites from cubic silsesquioxanes," J. Am. Chem. Soc. 123, 11420-30 (2001);
8. R. Tamaki, Y. Tanaka, M. Z. Asuncion, J. Choi, R. M. Laine, "Octa(aminophenyl)silsesquioxane as a Nanoconstruction Site," J. Am. Chem. Soc. 123, 12416-7 (2001);
9. R. Tamaki, J. Choi, R. M. Laine "A Polyimide Nanocomposite from Octa(aminophenyl)-silsesquioxane" Chem. Materials 15, 793-7 (2003);
10. J. Choi, R. Tamaki, S. G. Kim, R. M. Laine, "Organic/Inorganic Imide Nanocomposites from Aminophenylsilsesquioxanes," Chem. Mater. 15 3365-3375 (2003);
11. Jiwon Choi, Albert F. Yee, and Richard M. Laine, "Organic/Inorganic Hybrid Composites from Cubic Silsesquioxanes. Epoxy Resins of Octa(dimethylsiloxy-ethylcyclohexylepoxide) Silsesquioxane," Macromolecules 15, 5666-82 (2003);
12. J. Choi, A. F. Yee, R. M. Laine, "Toughening of cubic silsesquioxane epoxy nanocomposites using core shell rubber particles; a three component hybrid system," Macromol. 37 3267-76 (2004);
13. M. Z. Asuncion, I. Hasegawa, J. Kampf, R. M. Laine, "The selective dissolution of rice hull ash to form $[OSiO_{1.5}]_8[R_4N]_8$ (R=Me, $CH_2CH_2OH$) octasilicates. Basic nanobuilding blocks and possible models of intermediates formed during biosilification processes," Materials Chemistry 15, 2114-21 (2005);
14. R. M. Laine, "Nano-building blocks based on the $[OSiO_{1.5}]_8$ silsesquioxanes," J. Mater. Chem., 15, 3725-44 (2005);
15. N. Takamura, L. Viculis, R. M. Laine "A completely discontinuous organic/inorganic hybrid nanocomposite based on reactions of $[HMe_2SiOSiO_{1.5}]_8$ with vinylcyclohexene," International Polymers Journal web published 16 April (2007);
16. A. R. Bassindale, H. Chen, Z. Liu, I. A. MacKinnon, D. J. Parker, P. G. Taylor, Y. Yang, M. E. Light, P. N. Norton, M. B. Hursthouse, J. Organomet. Chem. 2004, 689, 3287;
17. a. A. Sellinger, R. M. Laine, "Silsesquioxanes as Synthetic Platforms. Thermally and Photo Curable Inorganic/Organic Hybrids," Macromol. 29, 2327-30 (1996). b. A. Sellinger, R. M. Laine, "Silsesquioxanes as Synthetic Platforms. III. Photocurable, Liquid Epoxies as Inorganic/Organic Hybrid Precursors," Chem. Mater. 8, 1592-3 (1996);
18. H. W. Ro, K. Char, E-C. Jeon, H-J. Kim, K. Kwon, H-J. Lee, J-K. Lee, H-W Rhee, C. L. Soles, D. Y. Yoon, "High Modulus Spin-On Organosilicates for Nanoporous Glasses," Adv. Mater. 19 705-710 (2007);
19. *Controlled Interphases in Composite Materials*, H. Ishida Ed., Elsevier Press, New York, 1990. a. D. E. Leyden, Ed. *Silanes, Surfaces and Interfaces*; Gordon and Breach: New York, 1986. b. E. P Plueddemann; Silane Coupling Agents; Plenum: New York, 1982;
20. J. Chojnowski, W. Fortuniak, P. Ros'ciszewski, W. Werel, J. Lukasiak, W. Kamysz, R. Halasa, Biocidal Polysilsesquioxanes: "Polysilsesquioxanes and Oligosilsesquioxanes Sub-stituted by Alkylammonium Salts as Antibacterial Biocides" J. Inorganic and Organometallic Poly. and Mater., 16, 219 (2006);
21. S. P. Denyer, "Mechanisms of Action of Antibacterial Biocides International Biodeterioration & Biodegradation (1995) 221-245;
22. T. Tashiro, "Antibacterial and Bacterium Adsorbing Macromolecules," Macromol. Mater. Eng. 286, 63-87 (2001);
23. U.S. Pat. No. 6,927,301 (Laine et al);
24. Published U.S. Application No. 20060083925 (Laine et al);
25. Published U.S. Application No. 20050142054 (Hasegawa et al);

26. O. Shchegolikhina, Y. Pozdniakova, M. Antipin, D. Katsoulis, N. Auner, B. Herrschaft, "Synthesis and Structure of Sodium Phenylsiloxanolates," Organometallics, 19, 1077-82 (2000); and 27. K. A. Andrianov, V. S. Tikhonov, G. P. Makhneva, G. S. Chemov, "Synthesis of Polycyclic Tetramethyltetraphenylcyclooctasilsesesquioxane," Izvestiya Akademii Nauk SSSR, Seriya Khimicheskaya, 4, 956-957 (1973).

In this growing field, there remains a need for various materials that can offer attractive and unique properties. There also remains a need to be able to provide alternative solutions to selectively design improved functional nanometric materials. Further, there continues to be a need to develop alternative new materials from renewable or sustainable resources.

SUMMARY OF THE INVENTION

In this growing field, there remains a need for various materials that can offer attractive and unique properties. There also remains a need to be able to provide alternative solutions to selectively design improved functional nanometric materials. Further, there continues to be a need to develop alternative new materials from renewable or sustainable resources.

The invention meets the above needs by providing improved multi-functional silsesquioxanes having new properties, new methods for producing these materials, and methods for using these materials. One aspect of the invention is directed at a multi-functional silsesquioxane, comprising: a. a polyhedral silsesquioxane including at least one first face and at least one second face that is spaced apart from the at least one first face, b. at least one first functionality bonded to the at least one first face, and c. at least one second functionality different from the first functionality, and being bonded to the at least one second face, with the at least one first functionality being adapted for bonding to a surface, another silsesquioxane, an organic functional group, or any combination thereof.

This aspect of the invention may be characterized by one or any combination of the following features: the silica of the silsesquioxane is derived from rice hull ash via an octa(tetramethylammonium)silsesquioxane octaanion; the polyhedral silsesquioxane is generally cubic, is generally octahedral, or a combination thereof; silicon is positioned in each corner of the generally cubic structure; each silicon in the corners of the generally cubic structure is bonded by at least one oxygen; the at least one first functionality is a silanated functionality; the at least one second functionality is selected from a sulfur containing compound, a nitrogen containing compound, a lumiphore, a cationic group, an anionic group, a catalyst, a catalyst precursor, a medicament, a bactericide, an antifungal, an antiviral, a surfactant, a hydrophobe, a hydrophile, a branched chain oligomer, a straight chain oligomer, a mixed functional group, an additional set of functional groups, or any combination thereof; the multi-functional silsesquioxane is selected from TTSE, TCTSE, TCPTSE, TOETSE, TGTSE, or any combination thereof; the multi-functional silsesquioxane is bonded to a surface selected from a plastic, metal, ceramic, carbon, a composite of any of the foregoing, or any combination thereof; the multi-functional silsesquioxane is bonded to the surface by way of a Si—OH group; the at least one first functionality is bonded to a substrate selected from metal, ceramic, carbon, a composite of any of the foregoing, or any combination thereof; the at least one second functionality is bonded to a substrate selected from metal, ceramic, carbon, a composite of any of the foregoing, or any combination thereof; the multi-functional silsesquioxane is a porous structure; the multi-functional silsesquioxane includes a plurality of generally uniformly dispersed pores in the porous structure and optionally includes at least one of the first or second functionality within resulting pores of the porous structure; the porosity of the porous structure ranges from about 5 to about 50% by volume; the porosity of the porous structure ranges from about 15 to about 30% by volume; the multi-functional silsesquioxane has a dielectric constant of about 1 to about 4 as measured by ASTM D150; the multi-functional silsesquioxane has a dielectric constant of about 2 to about 3 as measured by ASTM D150; the multi-functional silsesquioxane has a refractive index of about 1 to about 2 as measured by ASTM D542; the multi-functional silsesquioxane has a refractive index of about 1.2 to about 1.6 as measured by ASTM D542; the multi-functional silsesquioxane includes a generally coreshell layered structure; the multi-functional silsesquioxanes of the first aspect of the invention is used to make a dielectric film; or any combination thereof.

In another aspect of the invention, the multifunctional silsesquioxanes of the first aspect of the invention may be used in, as or otherwise for a coating.

This aspect of the invention may be characterized by one or any combination of the following features: the coating exhibits a wetting angle of water of at least about 60° as measured by ASTM D5946; the coating exhibits a wetting angle of water of at least about 75° as measured by ASTM D5946; the coating exhibits a wetting angle of water of at least about 90° as measured by ASTM D5946; the coating exhibits a wetting angle of water of at least about 105° as measured by ASTM D5946; the coating exhibits a wetting angle of water of at least about 120° as measured by ASTM D5946; the coating exhibits a pencil hardness of at least about 5H as measured by ASTM D3363, or the coating exhibits a hardness of at least about F as measured by ASTM D3363.

In another aspect of the invention, the multifunctional silsesquioxanes of the first aspect of the invention may be used in an article.

This aspect of the invention may be characterized by one or any combination of the following features: the multi-functional silsesquioxane is bonded to a substrate selected from metal, ceramic, carbon, a composite of any of the foregoing, or any combination thereof, via the at least one first functionality; the multi-functional silsesquioxane is bonded to a substrate selected from metal, ceramic, carbon, a composite of any of the foregoing, or any combination thereof, via at least two SiOH groups of the at least one first functionality; further including at least one outer layer that is bonded to the multi-functional silsesquioxane by the at least one second functionality; the at least one outer layer includes a component selected from a sulfur containing compound, a nitrogen containing compound, a lumiphore, a cationic group, an anionic group, a catalyst, a catalyst precursor, a medicament, a bactericide, an antifungal, an antiviral, a surfactant, a hypdrophobe, a hydrophile, a branched chain oligomer, a straight chain oligomer, a mixed functional group, an additional set of functional groups, or any combination thereof; within the space defined between either or both of the substrate and the multi-functional silsesquioxane or the multi-functional silsesquioxane and the at least one outer layer; the at least one outer layer includes a plurality of layers; the at least one outer layer includes a nucleophile; the att least one outer layer includes a mercapto group, an amino group, or a combination thereof; the at least one outer layer is an antibacterial layer that includes at least one alkyl ammonium salt.

Another aspect of the invention is directed at a method for making a multi-functional silsesquioxane coating, comprising the steps of: a. providing at least one source of silica; b. reacting at least a portion of the silica for forming a polyhedral cage that includes silicon at its corners, and for defining at least one first face and at least one second face spaced apart from the at least one first face, c. bonding at least one first functional group to the at least one first face, d. bonding at least one second functional group to the at least one second face; and e. bonding the first functional group to a substrate via a Si—OH functionality for defining a first multi-functional silsesquioxane coating on the substrate.

This aspect of the invention may be further characterized by one or any combination of the following: the at least one source of silica is derived from rice hull ash, and the polyhedral cage is based upon an octa(tetramethylammonium)silsesquioxane octaanion; the polyhedral cage is generally cubic; the least one first face is positioned generally opposite the at least one second face; bonding step (c) includes bonding at least three of the first functional group to the at least one first face; the bonding step (d) includes bonding at least three of the second functional group to the at least one second face; the first functional group is selected from a silanated functionality, the second functional group is selected from a sulfur containing compound, a nitrogen containing compound, a lumiphore, a cationic group, an anionic group, a catalyst, a catalyst precursor, a medicament, a bactericide, an antifungal, an antiviral, a surfactant, a hypdrophobe, a hydrophile, a branched chain oligomer, a straight chain oligomer, a mixed functional group, an additional set of functional groups, or any combination thereof; at least one of the first functional group or the second functional group includes a glycidyl functionality; further comprising a step of bonding the at least one second functional group to at least one second multi-functional silsesquioxane that is the same as or different from the first multi-functional silsesquioxane; either or both of the bonding steps (c) or (d) includes a reaction step in the presence of a catalyst; either or both of the bonding steps (c) or (d) include a reaction step that is monitored by fourier transform infrared spectroscopy and is progressed until the vSi—H peak at 2200 cm$^{-1}$ disappears; either or both of the bonding steps (c) or (d) include a reaction step that includes stirring a mixture of reactants at reflux in the presence of a catalyst; either or both of the bonding steps (c) or (d) include a reaction step that includes dissolving reactants in a solvent, mixing the reactants with a catalyst, recovering catalyst that is mixed with the reactants, evaporating the solvent, or any combination thereof; the catalyst includes Pt/C, the reaction step takes place at a temperature in the range of about 60 to about 110°, or both; the first multi-functional silsesquioxane coating is hydrolyzed for forming a mesoporous silicate structure with at least one of the first or second functional groups on the surfaces and within pores of the resulting structure; the coating is applied to a substrate via a solvent; the coating is applied to the substrate in the presence of an amine-functional agent; the solvent is selected from acetone, ethanol or THF; the amine-functional agent is selected from EA, DEA, TEA, MAE, DDM, OAPS or any combination thereof; or the bonding at least one first functional group to the at least one first face is done via a core-shell structure.

Another aspect of the invention is directed at tetraanionic half cube (TAHC) structures (e.g. SQ half-cube structures) and at a method for making a multi-functional silsesquioxane, comprising the steps of: a. providing an octa(substituted-phenyl)octasilsesquioxane, b. reacting the octa(substituted-phenyl)octasilsesquioxane in a solution comprising a cation and a first alcohol to produce a tetraanionic half cube having the structure (s-Ph$_4$TAHC):

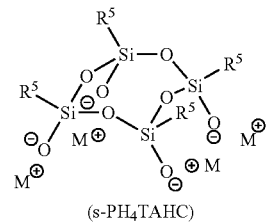

(s-PH$_4$TAHC)

wherein $R^5$ is a substituted phenyl group which may be selected from the group consisting of a phenyl, an alkyl phenyl, an allyl phenol, an ether phenyl, an amine phenyl, a thioether phenyl group and any combination thereof, and wherein the M$^+$ is a cation and may be selected from the group consisting of an alkali metal cation, an alkaline earth metal cation, a tetraalkyl ammonium cation, a tetraphosphonium cation, and any combination thereof.

This aspect of the invention may be further characterized by one or more of the following characteristics: the $R^5$ is a phenyl group, such that the octa(substituted-phenyl)octasilsesquioxane is octaphenyloctasilsesquioxane, and the tetraanionic half cube has the structure (PH$_4$-TAHC), wherein Ph is phenyl;

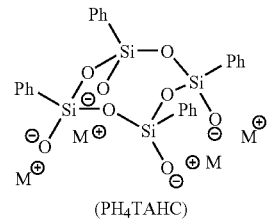

(PH$_4$TAHC)

the first alcohol is an alcohol having from 1 to about 20 carbon atoms; the first alcohol is selected from the group consisting of methanol, ethanol, n-propanol, n-butanol, isoamyl alcohol, n-pentanol, n-hexanol, ethylene glycol and any combination thereof; the cation is a sodium cation; the aspect further comprises the step of reacting the (s-PH$_4$TAHC) with a trichlorosilane; the trichlorosilane is selected from the group consisting of an alkyl trichlorosilane, an aryl trichlorosilane, a heteroaromatic trichlorosilane, a chloroalkyl trichlorosilane, an alkylepoxy trichlorosilane, an alkenyl trichlorosilane, an alkynyltrichlorosilane having a terminal or internal ether, and any combination thereof; the trichlorosilane is an alkyl trichlorosilane having from about 1 to about 8 carbon atoms; the aspect further comprises the step of reacting the (s-PH$_4$TAHC) with a first dimer having the structure: R$^6$SiCl$_2$—O—SiCl$_2$R$^7$, wherein R$^6$ and R$^7$ are selected from the group consisting of an alkyl, an aryl, a heteroaromatic, a chloroalky, an alkylepoxy, an alkenyl, an alkynyl having a terminal or internal ether, and any combination thereof, wherein R$^6$ and R$^7$ are identical to each other, wherein R$^6$ and R$^7$ are different from each other, or any combination thereof; the aspect further comprises reacting the s-PH$_4$TAHC with a second dimer having the structure: R$^8$SiCl$_2$—O—SiCl$_2$R$^8$ wherein R$^6$ and R$^8$ are different; the step of reacting the (s-PH$_4$TAHC) with a first dimer further comprises reacting the s-PH$_4$TAHC with a second dimer having the structure: R$^8$SiCl$_2$—O—SiCl$_2$R$^8$ wherein R$^8$ is different from both R$^6$ and R$^7$; the step of reacting the (s-PH$_4$TAHC) with a first dimer further comprises reacting the (s-PH₄TAHC) with a second dimer having the structure: R⁸SiCl₂-O—SiCl₂R⁸ wherein R⁸ is the same as R⁶ or R⁷; the aspect further comprises a step of reacting a second alcohol with a remaining chlorine atom of the trichlorosilane attached to the s-PH₄TAHC, wherein the second alcohol has a chemical structure of R⁹—OH, such that the chlorine atom is substituted with the second alcohol by alcoholysis to form a Si—O—R⁹ group, the second alcohol comprises a primary alcohol, a secondary alcohol or a tertiary alcohol, the second alcohol is a secondary alcohol or a tertiary alcohol; the aspect further comprises a step of hydrolyzing the s-PH₄TAHC following the alcoholysis step; or any combination thereof. The reaction products of any of the above-noted reactions of this aspect of the invention are also contemplated as within the scope of the invention.

BRIEF DESCRIPTION OF THE DRAWINGS

FIG. 3 illustrates an example of a reaction of a vinylsilane with a substituted silsesquioxane in accordance with the present invention, and more specifically a reaction of triethoxyvinylsilane and OHS to produce octa(triethoxysilylethylmethylsiloxy)silsesquioxane (OTSE).

FIG. 4 illustrates another example of a reaction of a vinylsilane, with a substituted silsesquioxane where the concentration of the vinylsilane is below the stoichemetric amount (e.g. a reaction of triethoxyvinylsilane and OHS at a molar ratio of about 4:1 to produce a SQs having about 4 triethoxysilane groups, such as tetratriethoxysilylethyldimethylsiloxy)(tetrahydridodimethylsiloxy)octasilsesquioxane (TTSE)).

FIG. 12 Part 1/2 and Part 2/2 illustrates an example of a multilayer SQ (e.g. multiple film layers of different monofunctional SQs and/or multi-functional SQs which may be based on OTSE and USE) structure that includes a relatively hard interlayer (e.g. OAPS).

FIG. 18a illustrates wetting of liquid droplets on an uncoated surface (e.g. water on an uncoated aluminum surface).

FIG. 18b illustrates wetting of liquid droplets expected for a coated surface (e.g. aluminum coated with TCTSE), and as compared with reference to FIG. 18a demonstrates that is possible to alter the wetting response of a surface by applying materials according to the present teachings.

FIG. 27 Part 1/2 and Part 2/2 illustrates the reaction of a monofunctional or multi-functional SQ (e.g. TCPTSE) onto a multi-layered SQ surface (e.g. a multi-layered structure having AOPS on the top layer) to form a structure having at least three layers of different SQs. FIG. 27 Part 1/2 illustrates the reactants and FIG. 27 Part 2/2 illustrates a product of the reaction.

FIG. 31$b$ illustrates an example of a reaction of an SQ (e.g. octaphenylocta silsesquioxane cube (OPS)) to form two half-cube SQs (e.g. tetrahenyltetraanionic silsesquioxane half cubes (PH$_4$TAHC)).

FIG. 31$c$ illustrates an example of a reaction of an SQ (e.g. an octa(iodophenyl) octasilsesquioxane cube) to form two half-cube SQs (e.g. tetraiodophenyltetraanionic silsesquioxane half cubes).

FIG. 31$d$ and FIG. 31$e$ illustrate examples of octa(substituted-phenyl)octa silsesquioxane cubes (s-Ph$_8$SQ) which contain bromine (e.g. Br$_{16}$OPS and Br$_{24}$OPS)

FIG. 32$a$ illustrates an example of a reaction between a trichlorosilane and an half-cube SQ (e.g. a s-PH$_4$TAHC) to form the half cube intermediate I. (HCl-I) which contains Si—Cl groups.

FIG. 32$b$ illustrates an example of a reaction between a trichlorosilane and an half-cube SQ (e.g. a PH$_4$TAHC) to form the half cube intermediate II (HCl-II) which contains Si—Cl groups.

FIG. 33 illustrates an example of an alcoholysis reaction of a half cube intermediate containing Si—Cl groups (e.g. HCl-I) to replace the chlorine atoms and form a half cube intermediate containing Si—O—R groups (e.g. HCl-III)

FIG. 36$a$ illustrates an example of a themogravimetric curve of a bifunctional cubic SQ (e.g. Me$_4$Ph$_4$[Si$_8$O$_{12}$]) and illustrates the measurement of the wt % concentration of the Si$_8$O$_{12}$.

FIG. 36$b$ illustrates an example of the FTIR spectra for a bifunctional cubic SQ (e.g. Me$_4$Ph$_4$[Si$_8$O$_{12}$]) showing the functional groups on the SQ molecule.

FIG. 37$a$ illustrates an example of the FTIR spectra of a Vinyl$_4$Ph$_4$ cubic SQ showing the functional groups on the SQ molecule.

FIG. 37$b$ illustrates an example of the MALDI spectra of a Vinyl$_4$Ph$_4$ cubic SQ for determining the molecular weight and of the SQ molecule.

FIG. 38 illustrates an example of the MALDI spectra for determining the molecular weight of i-Butyl$_4$Ph$_4$[Si$_8$O$_{12}$], such as one made from HCl-II.

FIG. 39 illustrates an example of the MALDI spectra for determining the molecular weight of Octyl$_4$Ph$_4$[Si$_8$O$_{12}$]), such as one made from HCl-I.

FIG. 40 illustrates an example of the MALDI spectra for determining the molecular weight of (ClCH$_2$)$_4$Ph$_4$[Si$_8$O$_{12}$]), such as one made from HCl-II.

DETAILED DESCRIPTION

Figure 1:
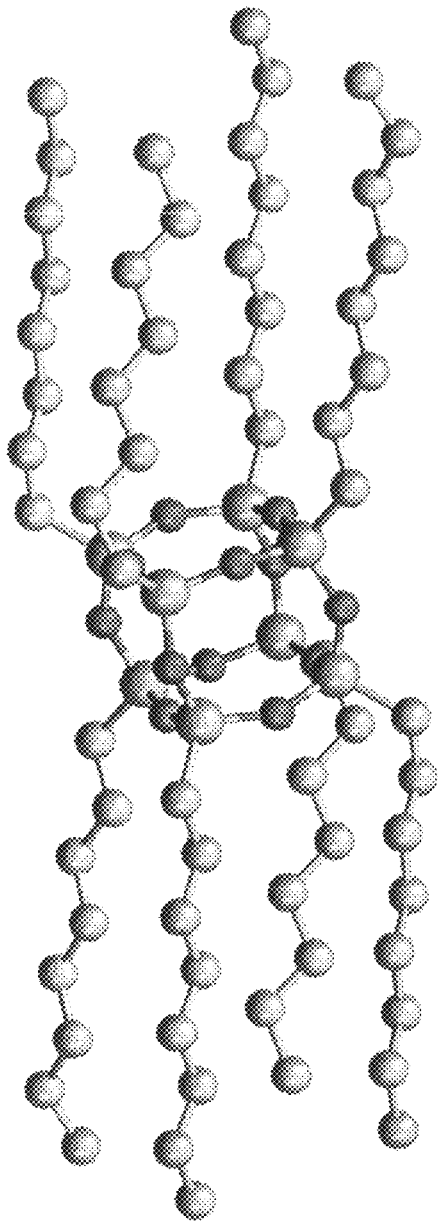
FIG. 1 illustrates an example of a silsesquioxane molecular structure having a functional group attached to some or all of the silicon atoms of the silsesquioxane (e.g. the single crystal structure of [octylSiO₁.₅]₈ as determined from x-ray spectroscopy).

For purposes herein, "OAPS" shall refer to octaminophenylsilsesquioxane. "MAE" shall refer to N-methylaminoethanol. "DDM" shall refer to 4,4'-Diaminodiphenylmethane. "EA" refers to ethanolamine. "DEA" refers to di-ethanol amine. "TEA" refers to tri-ethanolamine. "OTSE" shall refer to octa(triethoxysilylethyl methylsiloxy)silsesquioxane. "TTSE" shall refer to (tetratriethoxysilylethyldimethyl siloxy)(tetrahydridodimethylsiloxy)octasilsesquioxane. "TCTSE" shall refer to tetracyclohexenyltetratriethoxysilylethylsilsesquioxane. "TOETSE" shall refer to (Tetraoxyethanolethyldimethylsiloxyl)tetratriethoxysilylethylsilsesquioxane. "TGTSE" shall refer to (tetratriethoxysilylethyldimethylsiloxy)(tetraglycidyldimethylsiloxy) octasilsesquioxane. "TCPTSE" shall refer to (tetratriethoxysilylethyldimethylsiloxy) (tetra-3-chloropropyl-dimethylsiloxy)octasilsesquioxane. "OCPSE" shall refer to octa-3-chloropropyl-dimethylsiloxy)octasilsesquioxane. The formulas for the above which are shown in the following.

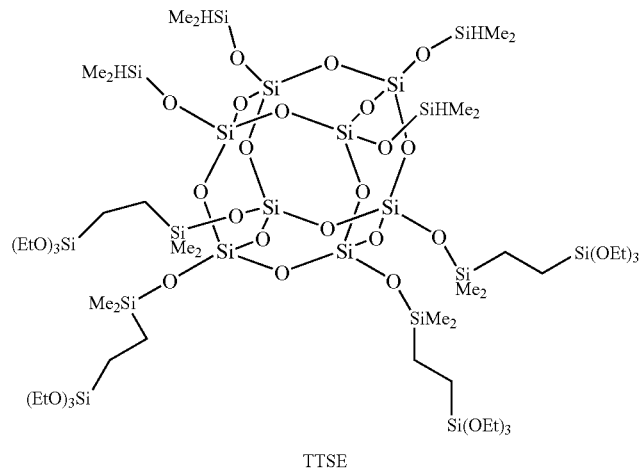
TTSE
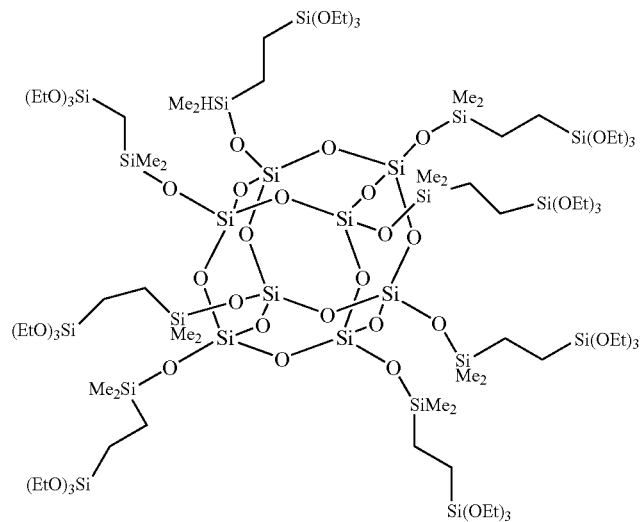
OTSE
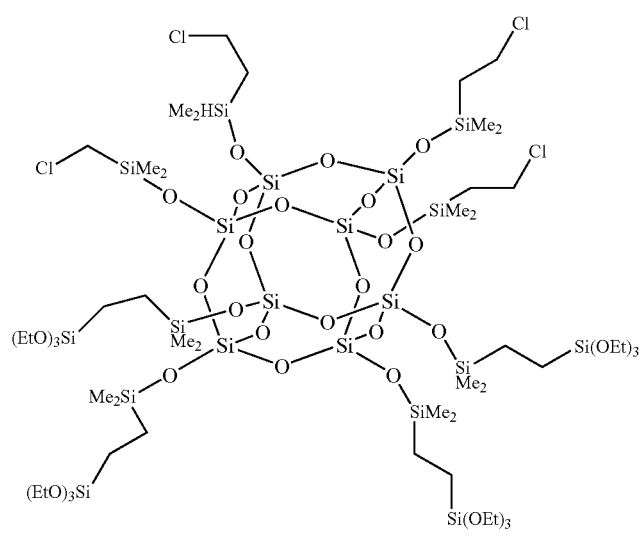
TCPTSE

-continued
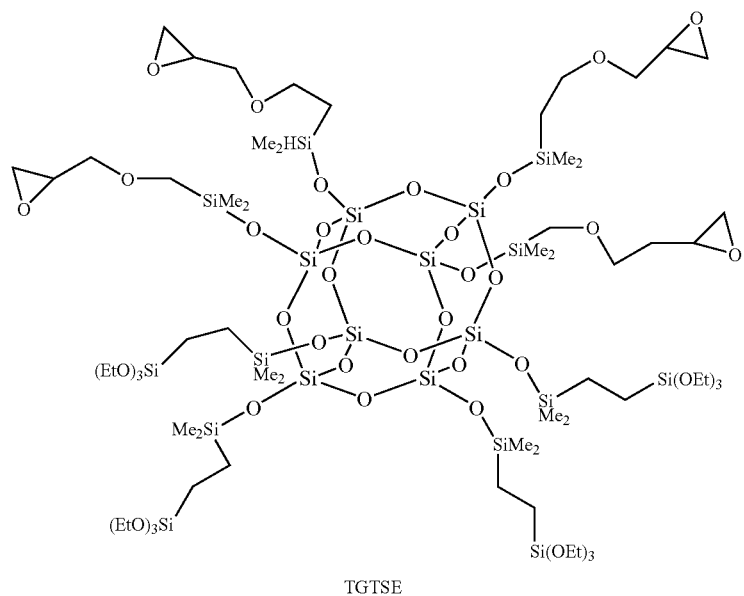
TGTSE
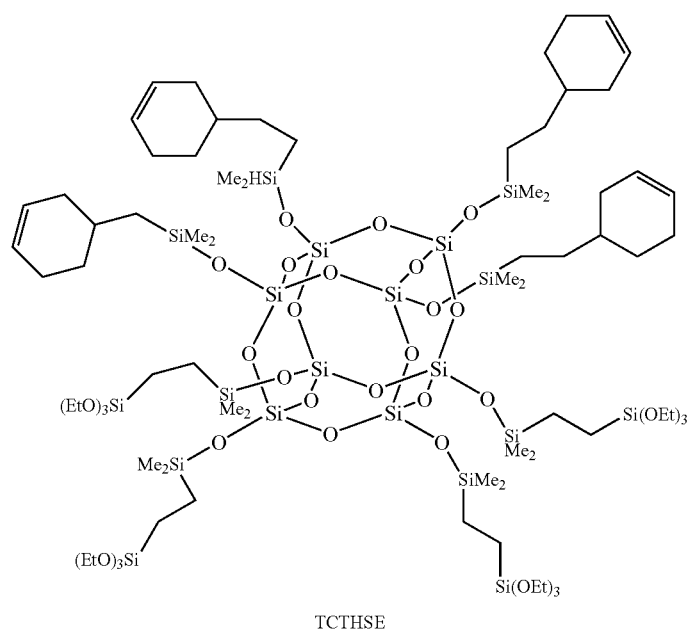
TCTHSE

-continued

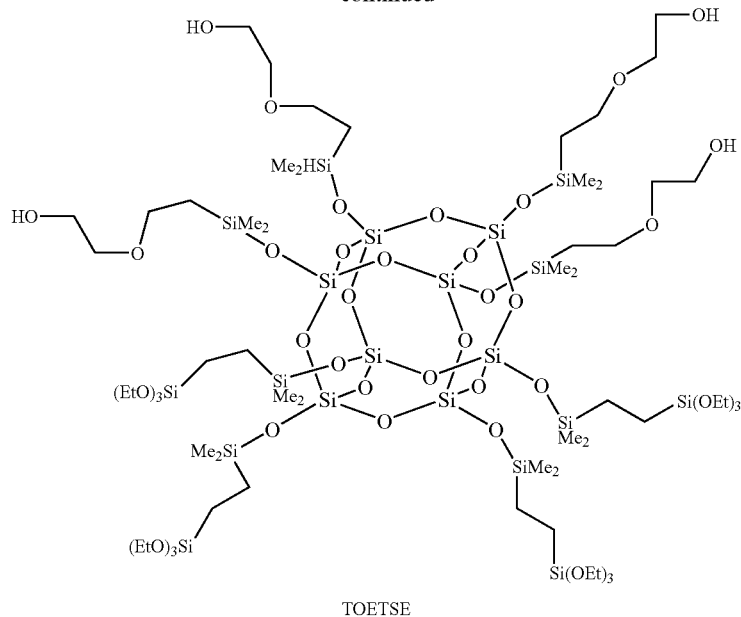

TOETSE

The present invention pertains to novel multifunctional silsesquioxane (SQ) structures and methods for making the same. In one general aspect, the invention makes use of an approach to the synthesis of hitherto unknown bi and/or tri-functional silsesquioxanes (SQs), wherein the functional groups are added (e.g., more or less statistically driven) by both attractive and repulsive forces between the reactive groups themselves on and off the SQ, by any catalyst, or a combination thereof. The resulting structures obtainable generally will be such that at least one functionality on the resulting SQ will have sufficiently different properties from another functionality on the resulting SQ. Partial (i.e. three of the four positions on one side) or complete (i.e. all four positions on one side) segregation as allowed by a statistical addition process is thereby possible, such that (for example) one first face of an octa (i.e. an octasilsesquioxane), one or two faces for a deca (i.e. a decasilsesquioxane), or possibly even one or two faces of a dodeca SQ (i.e. a dodecasilsesquioxane) are enriched in one first type of functional group, while another face (typically a face that is opposite to the first face) is enriched in a second, third or other type of functional group. It thus becomes possible that one face may have different reactivity than another face or faces for allowing one or both of a) a reaction with one or more other multi-functional molecules (e.g., bi or trifunctional molecules); or b) a reaction with surfaces with complementary reactivity allowing selective surface functionalization or surface enrichment in specific functional groups for modifying surface behavior in one or more respects such as scratch resistance, dielectric constants, hardness, transparency, ion conductivity, ion binding, metal and metal oxide particle binding, luminescence behavior, bactericidal property, any combination thereof, or otherwise. Such multi-functional SQ molecules may also be produced from an SQ or a functionalized SQ which is split into SQ half cubes and then adding functionalized silicon containing molecules to the half cubes in a way that these functionalized silicon containing molecules may also be used in reforming a full SQ structure.

In one respect, the present invention makes use of the recognition that polyhedral silsesquioxanes (SQs) functionalized with plural different functional groups, where the groups have differences in their properties, will organize themselves (e.g. in solution, in the melt state, in the liquid phase, or in the solid state) such that at least one first type of functional group tends to cluster at one face of the polyhedron, one SQ cubic face for example, while the other group or groups (e.g., at least one second type of functional group) will cluster away from (e.g., by approximately 180°) the at least one first type group, thereby effectively creating a molecular Janus or two faced molecule. Thus, as can be appreciated, such a design allows one side to have properties different and sometimes quite different to those of another side.

For example, if one set of functional groups is hydrolyzed to form Si—OH containing species, and the other set of functional groups remains unaffected (i.e. the other set of functional groups is not susceptible to hydrolysis), the Si—OH containing side can be used to coat wood, metal, ceramic, glass, and some plastic surfaces having Sur-OH groups where "Sur" refers to material surface, such as a surface of a polymer, ceramic, carbon, or any combination thereof. These Sur-OH groups may thus be able to bond to the Si—OH groups causing the molecule to adhere strongly to the surface; resulting in a bond strength that is much stronger (e.g. greater than at least 10%, and more preferably greater than at least 25% or even 50%) than the strength of bonds formed by simply silanization with a single silane group as used in traditional silanizing agents. The formation of such bonds places the remaining groups on the surface of this coating. These second types of functional group can then be reacted with a second set of two faced or single functional SQs or with other organic functional species that change (e.g. completely change) one or more of the original properties of the surface or that provide novel interlayers between the top layer and the surface. This provides the potential to design in novel properties that are significantly different from the original surface properties.

It is possible to design an upper set of functional groups to be reactive with other types of reactants and/or coating media providing ways to diversely manipulate the properties of the new surfaces for a wide variety of applications ranging from hydrophobicity/hydrophilicity to strong adhesion to antimicrobial to luminescent to scratch and abrasion resistant to forming interlayer dielectrics and/or hard strippable surfaces.

The present invention thus pertains to the development of multi-functional (e.g., bi-functional and trifunctional) cubic and other polyhedral silsesquioxanes (SQs) that can be used to process organic/inorganic nanocomposite thin films and coatings using multifunctional (e.g., bifunctional and occasionally trifunctional) SQs. The forms of the thin films, coatings or both can be as lines, thick films, multilayer systems with similar or different functionality, or any combination thereof. They may cover all or only a portion of an underlying surface. These films or coatings can be dense, graded, porous or any combination thereof. Functionality can be varied at nanometer length (e.g., on the order of about $10^1$ to about $10^3$ nm) scales with regard to mechanical and thermal properties, conductivity (electronic, ionic or thermal), biological interactions, light propagation (IR, visible, UV, mirror), other electromagnetic phenomena, or any combination thereof. The films can be prepared at room temperature or heated to a variety of temperatures including those that may degrade some parts of the functionality but not others. As will be seen, references to "layers" or "multi-layers" herein generally refer to a location in which the properties or characteristics of the molecule are substantially similar or even generally homogeneous. Multilayer structures can thus refer to a single molecular structure that has relatively controlled or consistent variation of properties or characteristics within the structure. Such structures may be possible from molecular synthesis. It also can refer to structures resulting from the assembly of plural discrete layers in separate steps (e.g., separate coating steps). In one aspect, it is also possible that the layers herein effectively are the layers that would result from a core-shell type of structure. Thus, layers or multi-layers is not intended to be limited to only planar arrangements of the structures.

For example, in one aspect, the present invention pertains to SQ resins (e.g., SQ epoxy resins, such as octa[(3-propylglycidylether)dimethylsiloxy]octasilsesquioxane and octa[1,2-epoxy-4-ethylcyclohexenyl)dimethylsilyloxy)]octasilsesquioxane) that offer, among other attributes at least one, or any combination of the following properties or characteristics:

1. thermal expansion coefficients (CTEs) tailored over 25-250 ppm/° C.;
2. $O_2$ barrier properties equal to commercial materials but with >100° C. higher stability, as measured e.g. using ASTM D3985;
3. low, room temperature viscosities (<1000 MPa·s, measured on the neat material e.g. using ASTM D445);
4. potential to be applied with minimal or no solvents to surfaces;
5. good adhesion to glass, carbon, ceramic, metal and some plastic surfaces;
6. superior resistance to moisture uptake and degradation (e.g., less than 1 wt %, preferably less than 0.5 wt % uptake after 7 d immersion);
7. resistance to hydraulic fluids, jet fuel and other organic solutions (e.g. volume swelling of less than about 50%, preferably less than about 30%);
8. one or any combination of mechanical properties such as high strength (e.g. high elastic modulus, E=2.4 GPa or higher), high fracture toughness ($K_{1C}$=1.8 MPa/m or tougher, as tested e.g. using ASTM E399), pencil hardness ($\geq$4H), high glass transition temperature (e.g. Tg$\geq$200° C.);
9. transparent to UV radiation;
10. hydrophobicity;
11. weatherability;
12. high temperature lubricant characteristics;
13. control of refractive index (RI); or
14. control of dielectric constants.

Turning now in further detail to the concept of bifunctional or Janus cubes, it is seen that the single crystal x-ray structure of $[octylSiO_{1.5}]_8$ shown in FIG. 1, one of several reported by A. R. Bassindale, et al, *J Organomet Chem.* 2004, 689, 3287 (incorporated by reference) points to a common feature of long chain flexible groups attached to cubes, the chains align uniformly to either side of the cage or silica core.

Figure 2:
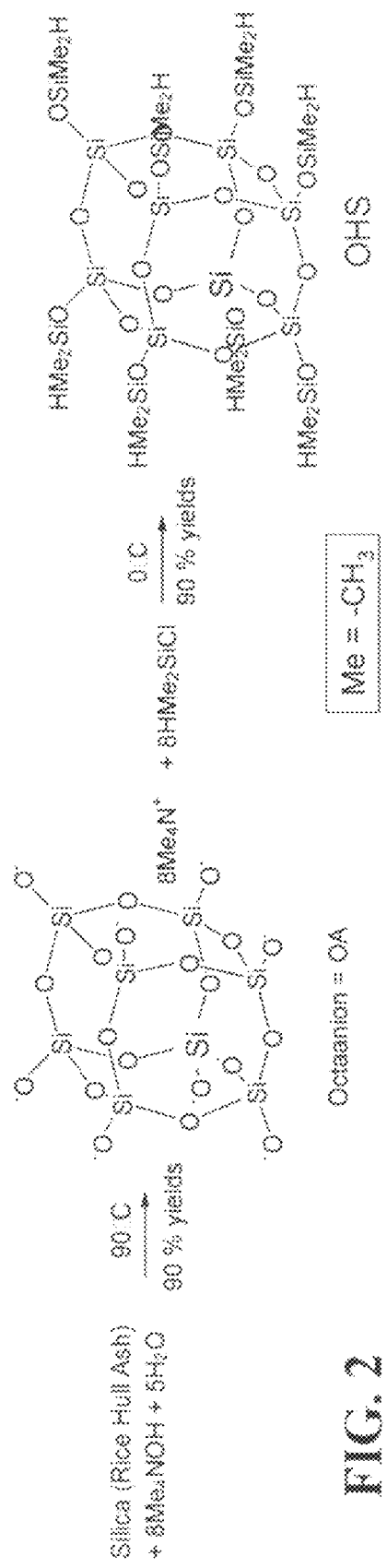
FIG. 2 illustrates an example of a reaction for producing a substituted silsesquioxane (e.g. octa(dimethylsilyloxy)silsesquioxane (OHS)) from silica (e.g. rice ash), pursuant to which the reaction may form an intermediate anion (e.g., an octaanion such as octa(tetramethylammonium)silsesquioxane).

One or the beneficial advantages of the present invention is that unique materials may be formed, having precisely tuned characteristics (particularly on the nano-scale) from sustainable or renewable material sources, such as bio-mass. Various reactions for preparing multi-functional SQs from a source of silica (such as a biomass material or by-product thereof, e.g., rice hull ash) may be used. FIG. 2 illustrates a reaction with an octaanion (e.g., octa(tetramethylammonium)silsesquioxane) for realizing a preferred silsesquioxane, such as octa(dimethylsilyloxy)silsesquioxane (OHS). FIG. 2 depicts a functionalized silsesquioxane produced by reacting the octaanion with chlorodimethylsilane. In general, other chlorosilanes may be used and even combinations of chlorosilanes may be used. For example, equal molar concentrations of two different chlorosilanes may be used to obtain a functionalized silsesquioxane having an average of four groups of one type and four of another. FIG. 3 illustrates a reaction to produce an octafunctional SQ, OTSE. Such SQ can thereafter be employed, for example as a "spacer layer" for building multilayer structures. For additional discussion of the formation of cage-like silica compounds akin to those of the present invention, see U.S. Pat. No. 6,927,301, incorporated by reference. See also, Published U.S. Application No. 20060083925 (Laine et al), incorporated by reference; and Published U.S. Application No. 20050142054 (Hasegawa et al), incorporated by reference.

FIG. 3 depicts a reaction where a silsesquioxane is reacted with an excess of an trialkoxyvinylsilane such that all of the vinylsilane is added to each functional site on the silsesquioxane. Lower concentrations of the reactant, shorter reaction times, or both may be used such that only some (e.g. half) of the functional sites are reacted and the silsesquioxane molecule thus may have multiple functional groups.

FIG. 4 illustrates another example of a suitable reaction herein by which it is possible to synthesize bifunctional SQs with an average very close to four of each type of functional group via reactions akin to reaction the reaction shown in FIG. 4. This is described in further detail, for instance in A. Sellinger, et al, "Silsesquioxanes as Synthetic Platforms. Thermally and Photo Curable Inorganic/Organic Hybrids," Macromol. 29, 2327-30 (1996); and A. Sellinger, et al., "Silsesquioxanes as Synthetic Platforms. Ill. Photocurable, Liquid Epoxides as Inorganic/Organic Hybrid Precursors," Chem. Mater. 8, 1592-3 (1996); both incorporated by reference.

The number of functional groups generally will be reported as an average because syntheses of oligomers typically may provide statistical numbers of additions (methods for synthesizing perfect Janus cubes (e.g. cubes having one face with exactly 4 functional groups of a first type and a second opposing face having exactly 4 functional groups of a second type) are described later). However, because the SQs often have cubic symmetry, there are six faces and therefore even if the groups add in a statistical manner off of the cage vertices, there will frequently be one face where three and possibly four of the same group can be found. Indeed it may be that the catalytic addition of a second group is driven to occur more frequently on the same face as the first group of that same type by its chemical affinity to the first group.

If one functionality is slightly more polar or hydrophobic than the other, then it is possible that this set of functionalities lies to one side and the opposing set may then "forced" to (or prefers) the opposite side. Thus statistically, it is reasonable to assume that solely based on polarity or "phobicity," bifunctional or Janus structures will form. This also provides a feature of the present invention that facilitates making novel surface coatings (e.g., films) with structures capable of being predictably tailored and controlled for predetermined characteristics at known nanometer distances projecting away from the surface.

Figure 5:
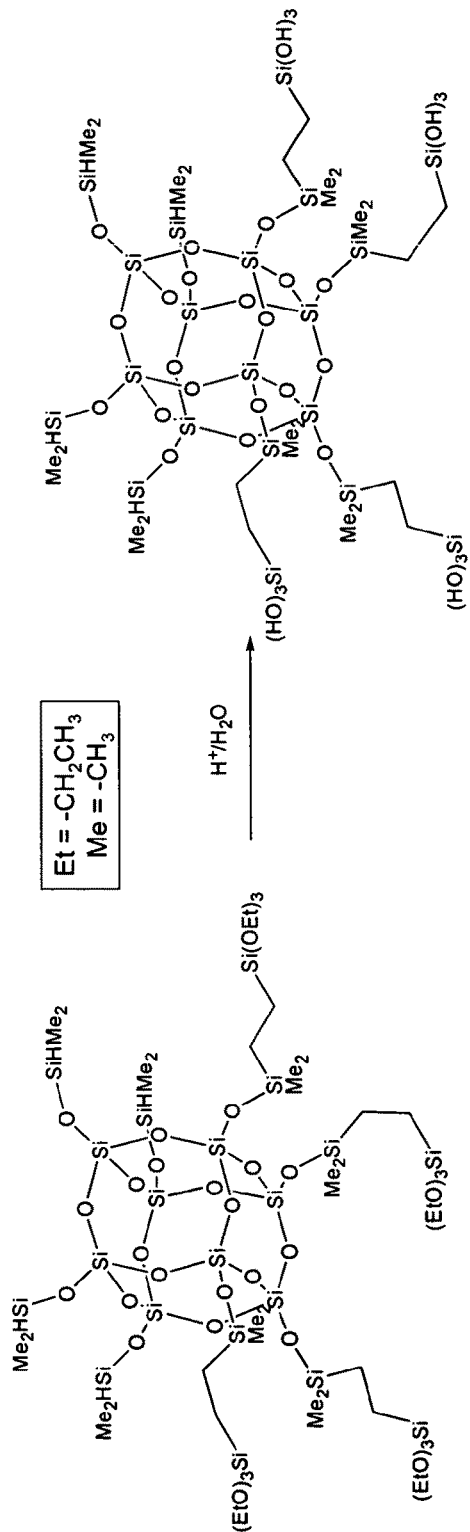
FIG. 5 illustrates an example of the hydrolysis reaction of a silsesquioxane (e.g. having trialkoxysilyl functionality such as TTSE or OTSE).
Figure 6:
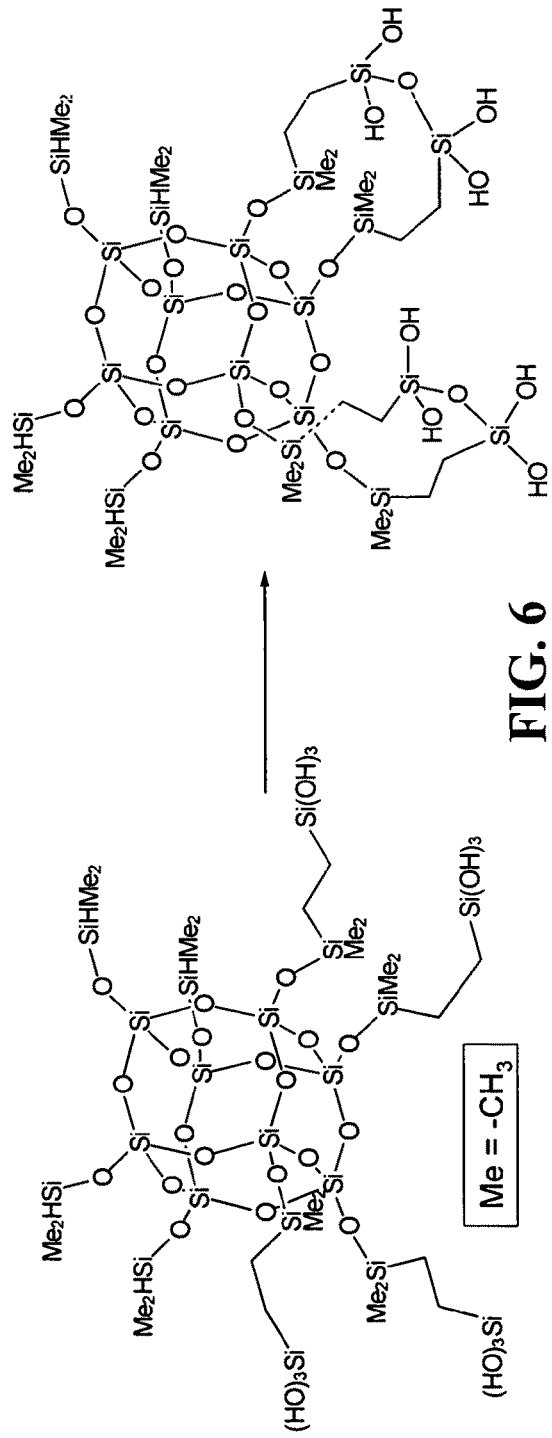
FIG. 6 illustrates an example of a further reaction of the hydrolysis product from FIG. 5 (e.g. a condensation reaction, such as a condensation reaction which combines two Si—OH groups, such as on a single molecule, to produces an Si—O—Si bond).
Figure 7:
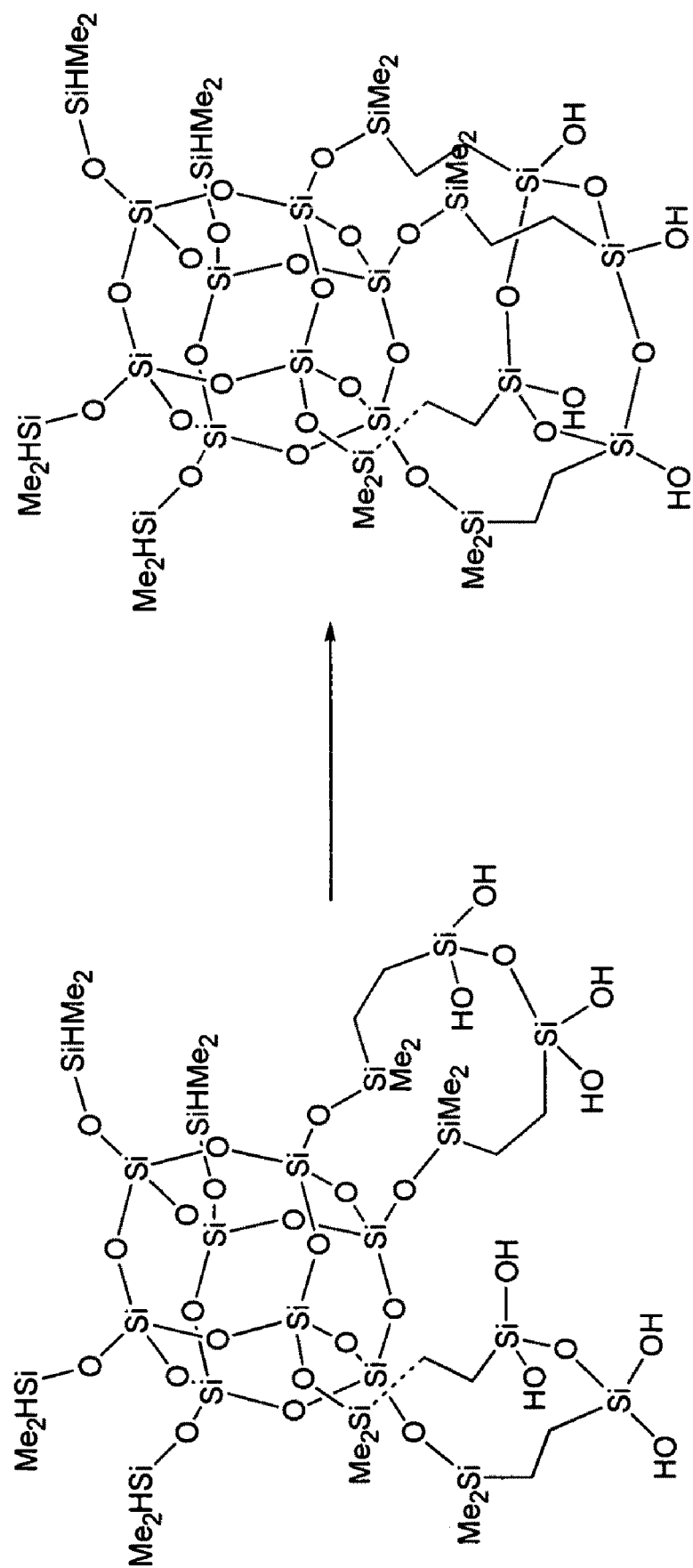
FIG. 7 illustrates another reaction of the hydrolysis product from FIGS. 5 and 6 (e.g. a condensation reaction, such as a condensation reaction which combines two Si—OH groups, such as on a single molecule, to produce a Si—O bond, and more specifically a Si—O—Si bond).

Without being bound by theory, consider what happens if a silsesquioxane having some functional alkoxysilane groups (e.g. the product of the reaction of FIG. 3) is hydrolyzed, such as by the reaction of FIG. 5. Assuming one face is likely to have more —Si(OH)$_3$ groups than another face, it is believed possible that hydrogen bonding followed by condensation will lead to structures suggested but not meant to be limiting as shown in FIGS. 6 and 7. The result of the reaction of FIG. 7 resembles structures seen by "High Modulus Spin-On Organosilicates for Nanoporous Glasses," Adv. Mater., 19, 705-710 (2007), incorporated by reference. From this hydrolysis reaction it is believed possible to make super hard, tough thin films like from a low-cost material (e.g. from silicon derived from rice hull ash).

It is believed possible that films (e.g., TGTSE) according to the invention can exhibit one or any combination of a CTE on the order of about 30 ppm/° C. (e.g. less than about 100 ppm/° C., more preferably less than about 50 ppm/° C.) as measured by ASTM D-696, a dielectric constant of about 2.33 (e.g. less than 5, more preferably from 0.5 to 5) as measured by ASTM D150, a porosity from about 10% to about 30% (e.g. about 20%) as measured by ASTM D6583-04, or an elastic modulus between about 5 and 20 GPa as measured from a load-displacement curve using a nanoindenter (e.g. tested according to ASTM D3363 using a Nanoindenter II, from MTS Systems Corporation, Oak Ridge, Tenn.). Furthermore, the base of this product (i.e. the product after hydrogen bonding followed by condensation) may include plural (e.g., four) Si—OH groups, thus offering the potential for silanization making it possible to form much stronger adhesive bonds to multiple surfaces much superior in terms of resistance to decohesion (e.g. the coating does not flake off), hydrolysis and/or chemical oxidation to silanization agents that depend on a single silane functional group to form surface bonds, e.g. R-Me$_2$SiCl (OR), R-MeSiCl$_2$ or (OR)$_2$, R—SiCl$_3$ or (OR)$_3$. See, *Controlled Interphases in Composite Materials*, H. Ishida Ed., Elsevier Press, New York, 1990; D. E. Leyden, Ed. *Silanes, Surfaces and Interfaces*; Gordon and Breach: New York, 1986; E. P Plueddemann; Silane Coupling Agents; Plenum: New York, 1982; J. Chojnowski, et al, Biocidal Polysilsesquioxanes: "Polysilsesquioxanes and Oligosilsesquioxanes Substituted by Alkylammonium Salts as Antibacterial Biocides" J. Inorganic and Organometallic Poly. and Mater., 16, 219 (2006); all hereby incorporated by reference.

Techniques for silanizing surfaces are practiced commercially in many applications ranging from coatings on silica powders used in dental restoratives, to sizing on carbon and glass fibers used as reinforcing media to coatings applied to grout used between tiling showers and baths. See e.g., already cited above "High Modulus Spin-On Organosilicates for Nanoporous Glasses," Adv. Mater., 19, 705-710, (2007); *Controlled Interphases in Composite Materials*, H. Ishida Ed., Elsevier Press, New York, 1990; D. E. Leyden, Ed. *Silanes, Surfaces and Interfaces*; Gordon and Breach: New York, 1986; and E. P Plueddemann; Silane Coupling Agents; Plenum: New York, 1982, all hereby incorporated by reference.

In general herein it is possible to silanize a surface by reacting chloro- or alkoxysilanes (e.g. R'Me$_2$SiCl or R'Me$_2$SiOEt) with surface hydroxyl groups, SUR-OH, to form R"Me$_2$Si—O-SUR bonds. R can be hydrophobic, hydrophilic or reactive (propylamine, glycidyl epoxy, methylmethacrylate, etc.). It should be recognized, however, that it is possible that SUR-O—Si bonds may be susceptible to hydrolysis and may eventually wash off. Thus, the teachings herein also contemplate the employment of one or more silanizing agents such as R'MeSiCl$_2$, R'MeSi(OEt)$_2$, R'SiCl$_3$, or R'Si(OEt)$_3$. For steric reasons these latter silanizing agents are believed to form dimers and/or trimers (akin to silsesquioxanes) that then bond to the surface. See *Controlled Interphases in Composite Materials*, H. Ishida Ed., Elsevier Press, New York, 1990, hereby incorporated by reference. With more than one SUR-O—Si bond, these latter systems are believed to be potentially more resistant to hydrolysis; however, they still place only one R' group at the surface.

Figure 8:
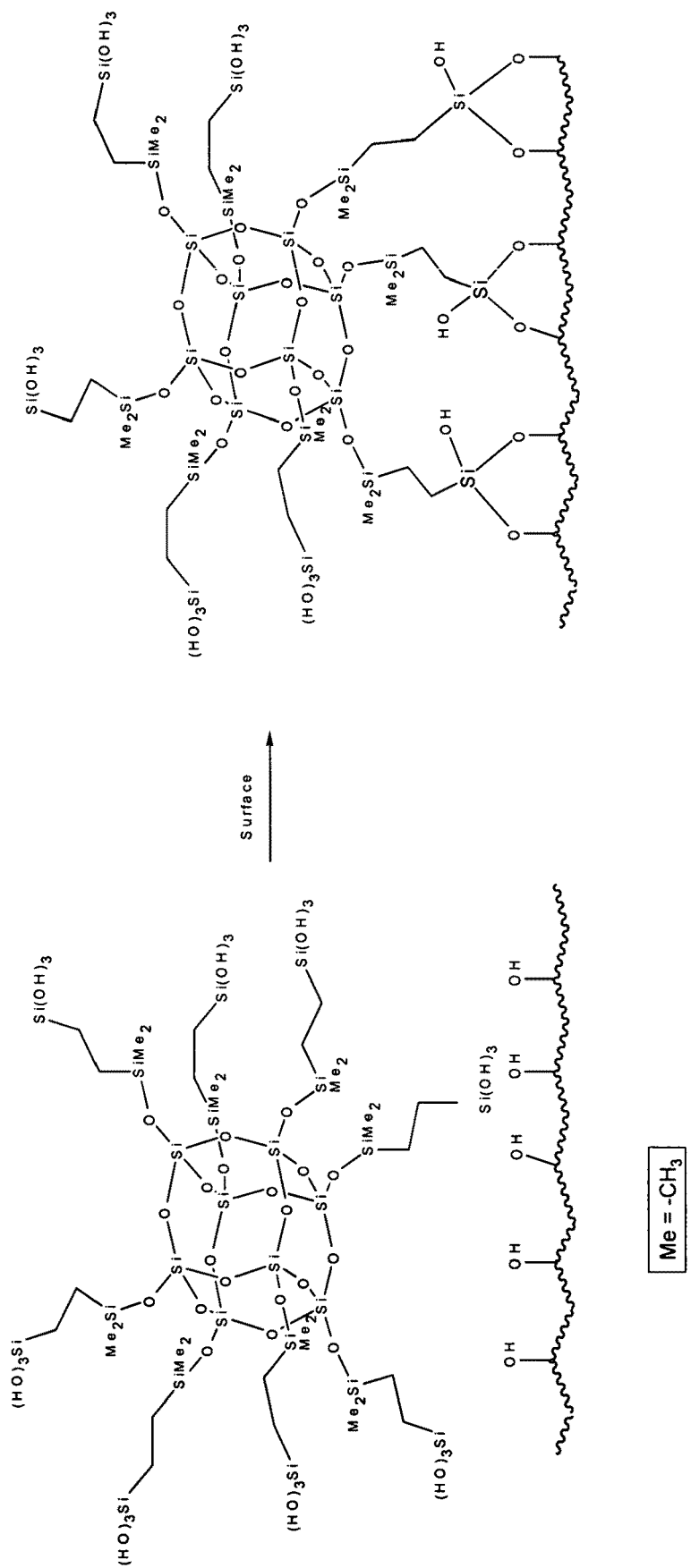
FIG. 8 illustrates an example of the reaction of a silsesquioxane with a functionalized surface, more specifically having one or more functional Si—OH group (e.g. cta(trihydroxysilylethylmethylsiloxy)silsesquioxane or tetratrihydroxysilylethyldimethylsiloxy)(tetrahydridodimethylsiloxy)octa silsesquioxane) with a substrate having surface OH groups (i.e. SUR-OH) to form one or more Si—O-SUR bonds.

Making advantageous use of the multifunctional SQs of the present invention, it is seen that the SQs (e.g., such as the illustrative product of FIG. 7) may be capable of placing plural (e.g., 3-4) Si—OH groups in a position to couple with SUR-OH groups and four R' groups away from the surface. Hence it is possible to obtain excellent adhesion plus anchor sets of three to four functional groups with each structure. These groups do not have to be the same. They could be mixtures of any functional group desirable. Furthermore for OTSE, by way of example, coatings can be made similar to surfaces described in "High Modulus Spin-On Organosilicates for Nanoporous Glasses," Adv. Mater., 19 705-710 (2007), incorporated by reference, for example on A12024 T3 as suggested by FIGS. 8 and 10. Materials that are quite resistant to salt corrosion and yet also offer the potential for further surface modification are thus believed possible as well.

Figure 9:
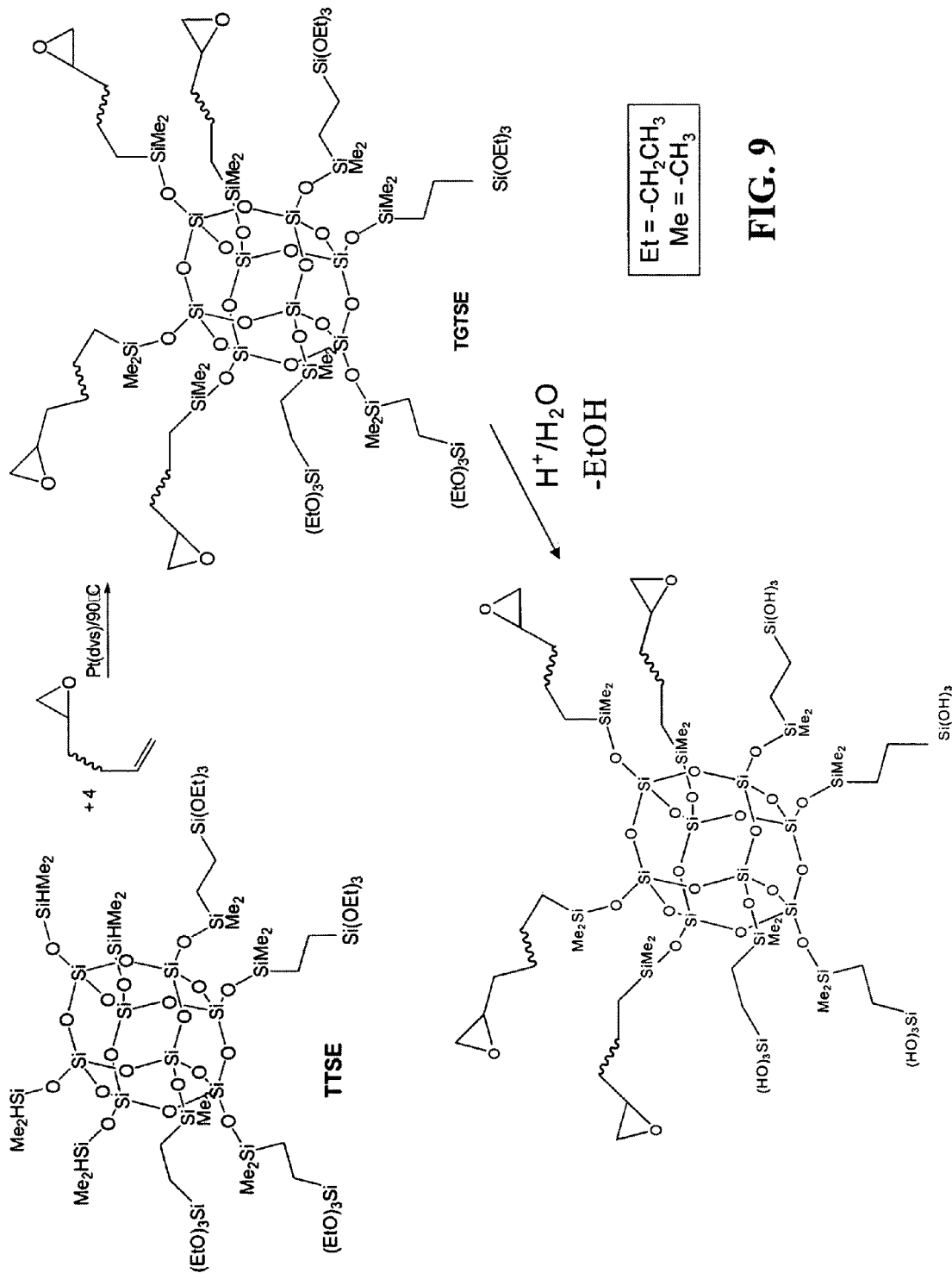
FIG. 9 illustrates an example of the addition of an epoxide functionality to an SQ (e.g. to a multi-functional SQ such as TTSE)
Figure 10:
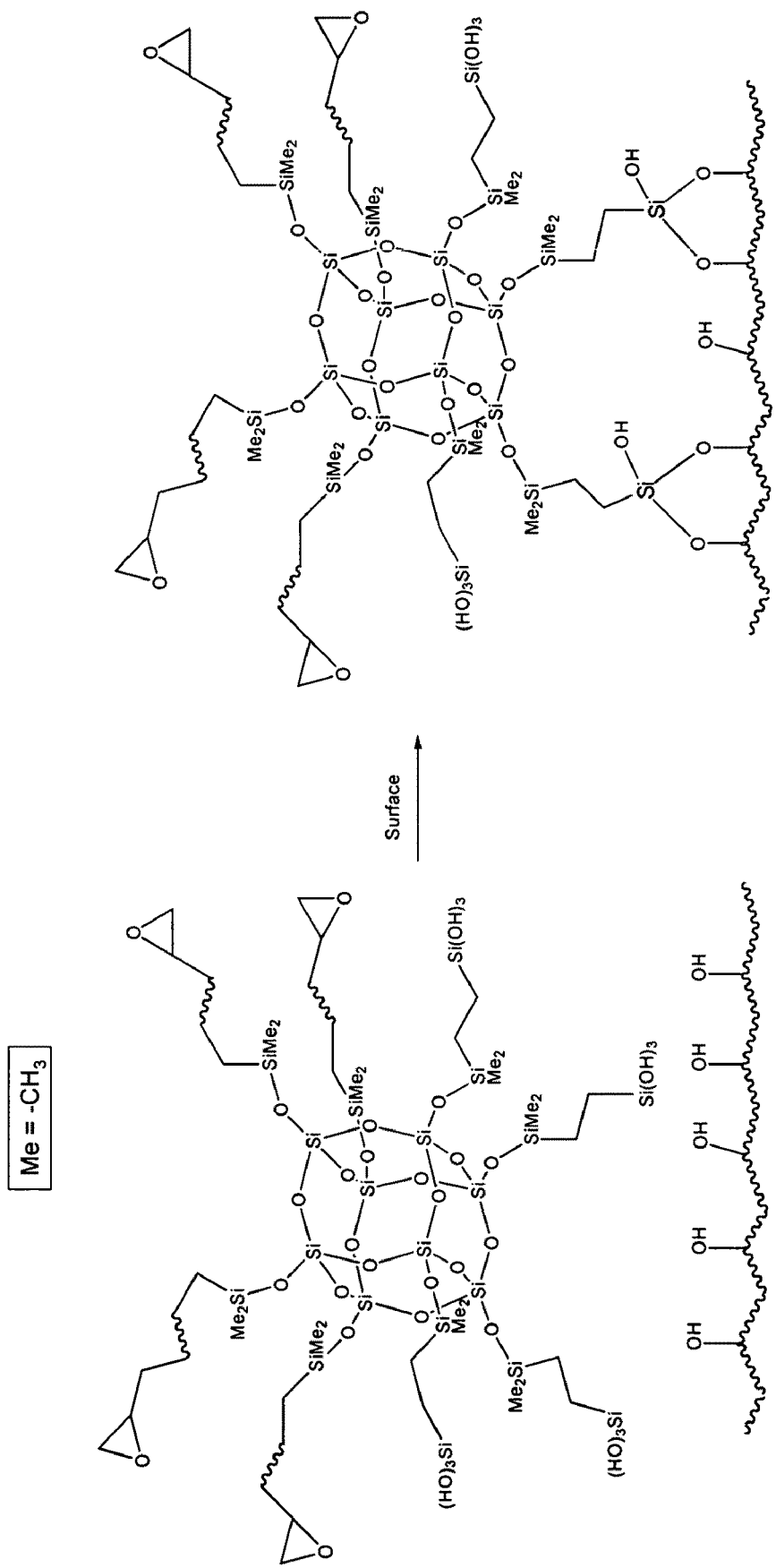
FIG. 10 illustrates an example of the addition of an SQ (e.g. a multifunctional SQ) having an epoxide functionality onto a substrate (e.g. onto a substrate having SUR-OH groups) where the functionality of the surface may change (e.g. from SUR-OH to SUR-epoxy).
Figure 11:
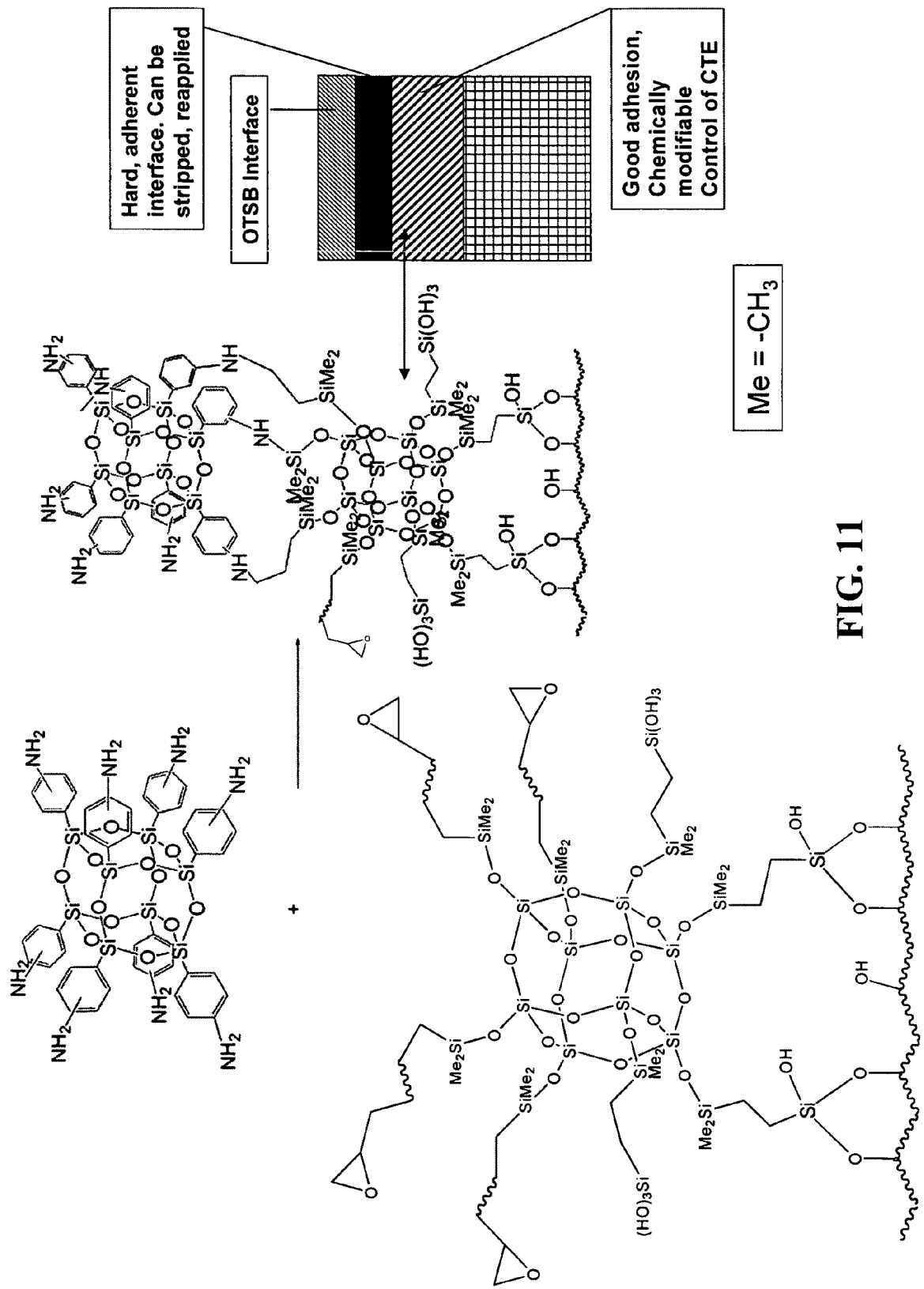
FIG. 11 illustrates an example of a multi-layered material made from different SQs where one or more layers may provide a unique characteristic or feature (e.g. strength, adhesion, chemical resistance, ability to be stripped and even reapplied, hardness, control of coefficient of thermal expansion, ability to be chemically modified, and the like) to the material; this figure further illustrates the reaction of an SQ having epoxy functionality to an SQ having an amine functionality (e.g. OAPS).

By way of further illustration, it is possible to build novel structures based upon one or more of the multi-functional SQs of the invention. For example, with reference to the FIG. 8 OTSE based coating (it being realized that other SQs may be substituted for the OTSE), one approach is to overlay a first SQ layer with a hydrolyzed TGTSE (where G=glycidyl) such as by the reaction of FIGS. 9 and 10. The TGTSE may be prepared by reacting TTSE with vinylexpoxide as illustrated in FIG. 9. The TGTSE may further undergo a hydrolysis reaction (as illustrated in FIG. 9) to provide Si—OH functional groups which may react with SUR-OH groups (as illustrated in FIG. 10), e.g. through a condensation reaction. In this manner, a strongly adherent surface coating may be formed with an adhesive interlayer, which then is capable of bonding to a polymer overcoat. The reactions of FIGS. 10 and 11 depict such an example. The octamino compound (OAPS) of the reaction of FIG. 11 is believed to play a potentially important role in resulting beneficial resin properties, such as one or more of the properties described in the foregoing.

In another possible approach, it is possible to apply the teachings herein for forming a composite coating systems per FIG. 11, which is capable of including a layer that has a relatively low interfacial bond strength relative to the interfacial bond strength of an opposing layer, thus providing the capability of providing strippable layer, (e.g., a strippable surface layer). An example of such an interfacial structure is consistent with that of the high hardness and high modulus layer described in "High Modulus Spin-On Organosilicates for Nanoporous Glasses," Adv. Mater., 19, 705-710 (2007), incorporated by reference.

It is also possible that some SQ molecules (e.g., the TTSE molecule) will have plural (e.g., four) $Me_2SiH$ groups that can serve as points of attachment via hydrosilylation, such as in the reaction FIG. 9. In this manner it may be possible to introduce multiple new functional groups.

It is also possible to create multiple SQ layers that could be put on any surface depending on what bifunctional SQ one started with which would be determined by the chemistry of the substrate surface. See FIGS. 11 and 12.

FIG. 12 illustrates another example of a multilayer SQ film structure that includes a relatively hard interlayer. Such a structure may include one or more layers prepared from OTSE, by way of example.

As previously mentioned, another method for obtaining a multi-functional silsesquioxane uses a tetraanionic silsesquioxane half cube (e.g. a substituted-phenyl tetraanionic silsesquioxane half cube). A benefit of this method is that it may provide improved control of the molecular structure such that most (e.g. greater than about 50%, preferably greater than about 75%) of the molecules have a desired structure. For example, it may be possible, using the SQ half cubes to prepare, and possibly isolate, "perfect Janus cubes", i.e. two-faced SQs where one face contain only a first functional group and a second opposing face contains only a second functional group. In other words, this approach may allow for the production of perfect Janus molecules in yields greater than about 20%, preferably greater than about 50% and more preferably greater than about 75%, e.g. greater than about 85%.

Multi-functional silsesquioxanes as taught in the foregoing, or structures incorporating the same, may also be obtained using a tetra substituted-phenyl tetraanionic silsesquioxane half cube (s-$Ph_4TAHC$) having the structure:

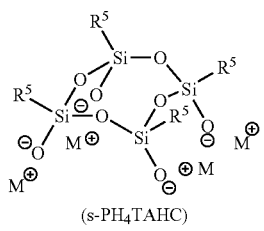

(s-$PH_4TAHC$)

where $R^5$ is a substituted phenyl group and $M^+$ is the cation.

The substituted phenyl group may be phenyl, or a phenyl where one or more of the hydrogen atoms are substituted, e.g. substituted for an alkyl, an allyl, an ether, an amine, a thioether, a halogen, hydroxyl group and any combination thereof. As such, the substituted phenyl group may be an alkyl phenyl, an allyl phenol, an ether phenyl, an amine phenyl, a thioether phenyl, a halophenyl, a phenol, phenyl and any combination thereof. It may be preferable that the substituted phenyl groups, $R^5$, are identical, but in general they may vary. $M^+$ may be any cation having a positive charge of 1 or 2. Preferably, the cation includes a cation selected from the group consisting of an alkali metal cation, an alkaline earth metal cation, a tetraalkyl ammonium cation, a tetraphosphonium cation, and any combination thereof.

The silsesquioxane half cube (s-$Ph_4TAHC$) may be obtained by reacting an octa(substituted-phenyl)octasilsesquioxane (s-$Ph_8SQ$), for example in the presence of a first alcohol. The reaction may be expressed by the reaction in FIG. 31a. In one more specific example, the substituted phenyl may be phenyl, wherein octaphenylocta silsesquioxane (OPS) is reacted to form the tetraphenyltetraanion half cube ($Ph_4TAHC$). An example of this reaction is illustrated by the reaction depicted in FIG. 31b where the resulting half cube is a sodiated half cube. The yield of the $Ph_4TAHC$ may be greater than about 20%, preferably greater than about 50%, more preferably greater than 70% and most preferably greater than about 80%. The s-$Ph_4TAHC$ or $Ph_4TAHC$ salt thus formed may also contain waters of hydration.

Figure 31C:
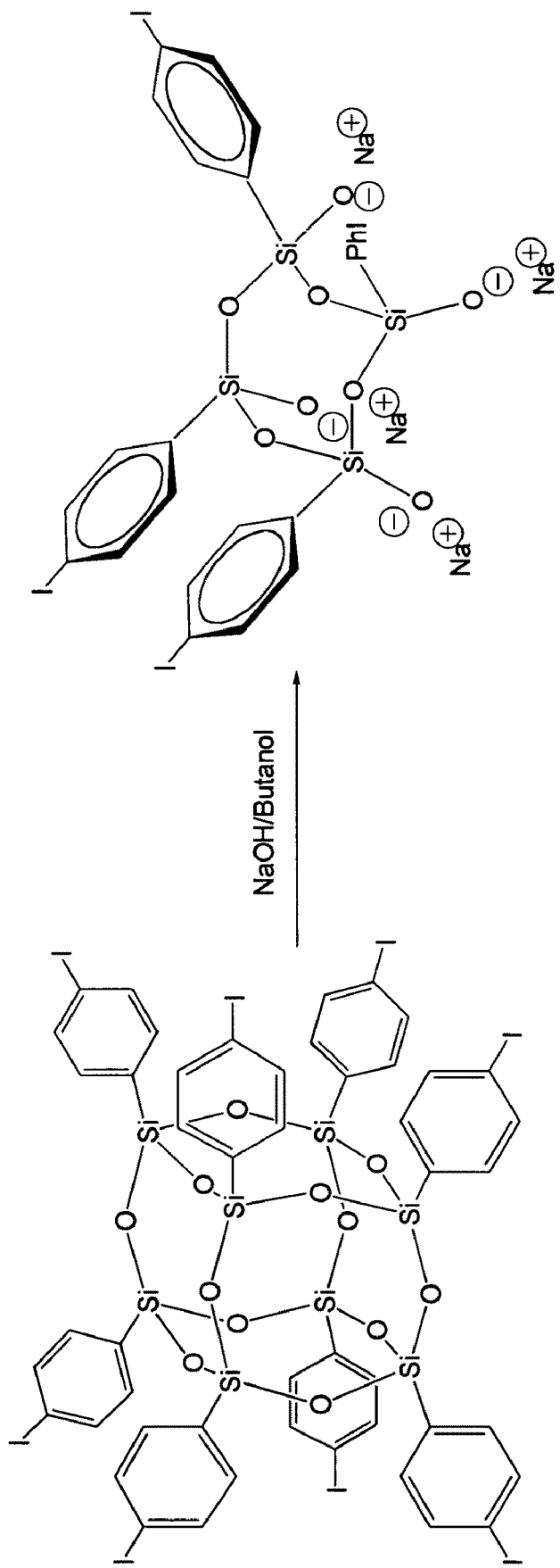
FIG. 31$a$ illustrates an example of a reaction of an SQ (e.g. an octa(substituted-phenyl)octasilsesquioxane cube (s-Ph$_8$SQ) to form two half-cube SQs (e.g. tetra substituted-phenyltetraanionic silsesquioxane half cubes (s-PH$_4$TAHC)).

The OPS may be an iodated OPS as shown in FIG. 31c where the resulting half cube (i.e. s-$Ph_4TAHC$) is the sodiated salt of the tetra(iodophenyl)tetraanionic half cube.

Other nonlimiting examples of halogenated octaphenylsilsesquioxanes that may be used to produce a s-$Ph_4TAHC$ include $Br_{16}OPS$ and $Br_{24}OPS$, as shown in FIGS. 31d and 31e respectively.

Once formed, the silsesquioxane half cube (s-$Ph_4TAHC$) may undergo one or more reactions or reaction steps in order to form a multi-functional silsesquioxane. For example, s-$Ph_4TAHC$ may be reacted with a trichlorosilane having the structure $R^4$—$SiCl_3$ whereupon one chlorine atom is removed and associates with the metal cation and a siloxy bond is formed connecting the silane to the silsesquioxane half cube. This reaction is shown schematically in FIG. 32a, where the product is a half cube intermediate, designated by HCl-I.

The trichlorosilane may be an alkyl trichlorosilane, an aryl trichlorosilane, a heteroaromatic trichlorosilane, a chloroalkyl trichlorosilane, an alkylepoxy trichlorosilane, an alkenyl trichlorosilane, an alkynyltrichlorosilane having a terminal or internal ether, and any combination thereof. Exemplary trichlorosilanes include alkyl trichlorosilanes containing from about 1 to about 22 carbon atoms, more preferably from about 1 to about 8 carbon atoms. For example, without limitation, methyl trichlorosilane may be used.

The ratio of the trichlorosilane to the s-$Ph_4TAHC$ preferably is at least 4, more preferably at least 4.3, and most preferably at least 5.

Besides having chlorosilane groups, the HCl-I molecule may also contain hydroxychlorosilanes which may form from any waters of hydration present in the s-$Ph_4TAHC$. This is also shown in FIG. 32a, where on average the intermediate HCl-I contains x hydroxychlorosilane groups.

An exemplary HCl-I, represented by HCl-II as given in FIG. 33.b may be formed by reacting $Ph_4TAHC$ with a trichlorosilane.

The presence of Si—Cl bonds in HCl-I and HCl-II may result in the polymerization of the intermediate, e.g. by the formation of HCl. A second alcohol may be reacted with the intermediate (e.g. with HCl-I or HCl-II) to form a compound which is more stable than the silicon chloride containing intermediate. The second alcohol may have a general formula of $R^3OH$ and may be a primary alcohol, a secondary alcohol, a tertiary alcohol, or any combination thereof. Preferably, the second alcohol comprises or consists essentially of a bulky alcohol, e.g. a secondary alcohol, a tertiary alcohol, or a combination. The second alcohol may be added after forming the half cube intermediate (e.g. HCl-I or HCl-II). Preferably, the second alcohol is present during the reaction of the trichlorosilane and the s-Ph$_4$TAHC. The reaction of the second alcohol with the half cube intermediate HCl-I is shown in FIG. 33 resulting in half cube intermediates III (HCl-III). This alcoholysis step may allow for the isolation and/or the purification of the HCl-III compound.

Figure 34:
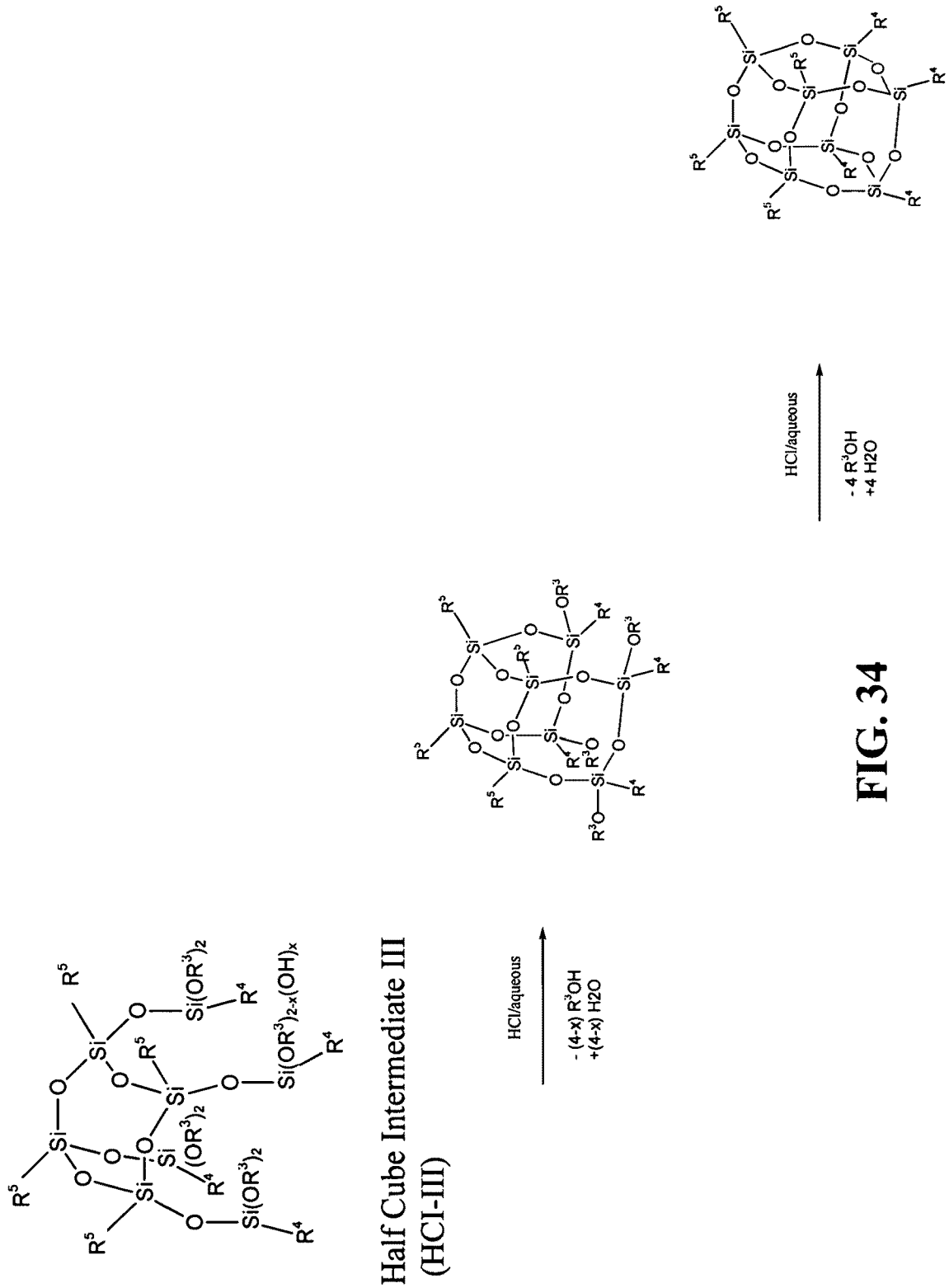
FIG. 34 illustrates an example of a reaction to convert a half cube intermediate (e.g. HCl-III) into a SQ cube having one face with a first functional group ($R^5$) and an opposing face having a second functional group ($R^4$) on each corner.

The process for synthesizing the multifunctional silsesquioxane may further include a step of reacting the HCl-III compound in an acid solution to remove the R$^3$OH and form Si—O bonds, and more preferably Si—O—Si bridges. This reaction may be illustrated by FIG. 34 wherein HCl-III is reacted with 4-x water molecules in an HCl aqueous solution to produce 8-x molecules of R$^3$OH and 4 Si—O—Si bridges, thus forming a multifunctional silsesquioxane having four R$^5$ functional groups and four R$^4$ functional groups.

Figure 35:
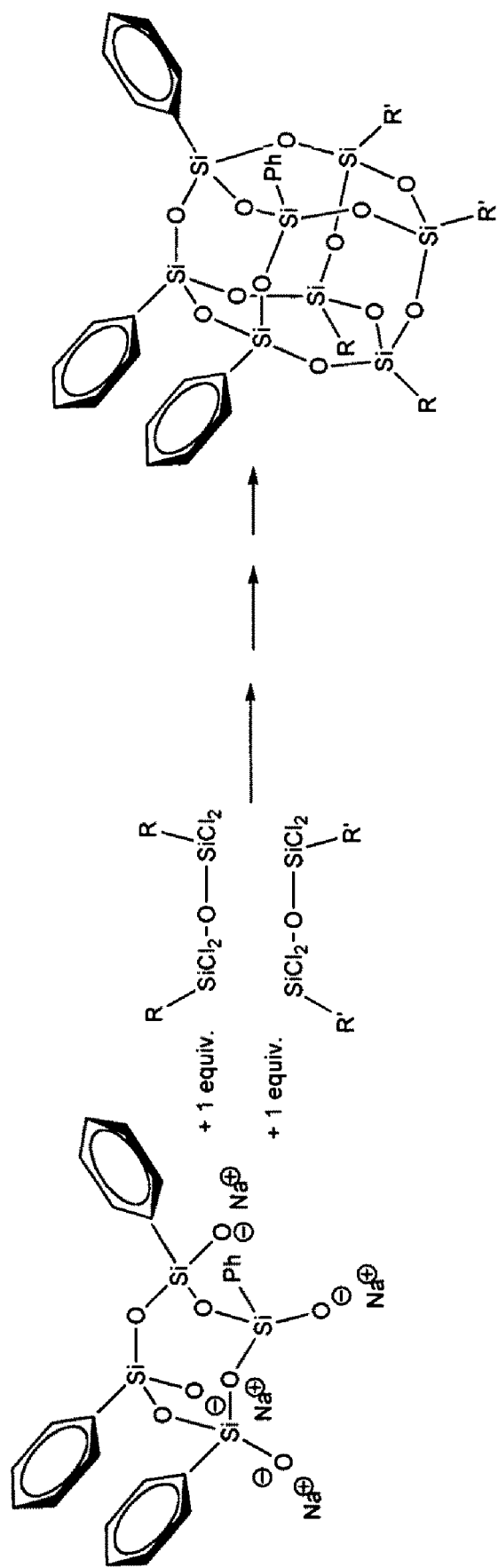
FIG. 35 illustrates an example of a reaction of a half-cube SQ (e.g. a s-PH$_4$TAHC or a PH$_4$TAHC) with two different difunctional silane dimers to form a cubic SQ having a first function group (e.g. a phenyl group or a substituted phenyl group) on one face at each of the corners and two different functional groups on the opposing face of the cube.

The step of reacting the silsesquioxane half cube (s-Ph$_4$TAHC) with a trichlorosiloxane may be substituted for a step of reacting the Ph$_4$TAHC with one or more difunctional silane dimer having the formula: R$^6$SiCl$_2$-O—SiCl$_2$R$^7$, where R$^6$ and R$^7$ are alkyl, aryl, heteroaromatic, chloroalkyl, alkylepoxy, alkenyl, alkynyl, ether, and any combination thereof. The reaction product may be described by HCl-I where the functional groups are R$^5$ and R$^7$. R$^6$ and R$^7$ may be the same or they may be different. If only one difunctional silane dimer is used and R$^6$ and R$^7$ are identical, then a reaction product may be formed having have four R$^6$ functional groups. If only one difunctional silane dimer is used and R$^6$ and R$^7$ are different, then a reaction product may be formed having have about two (e.g. exactly two) R$^6$ functional groups and about two (e.g. exactly two) R$^7$ functional groups. Two different difunctional silane dimers may also be used. For example a first dimer may have a formula: R$^6$SiCl$_2$—O—SiCl$_2$R$^7$ and a second dimer may have a formula: R$^8$SiCl$_2$-O—SiCl$_2$R$^8$. R$^8$ may be the same as R$^6$ or R$^7$ or it may be the different from both R$^6$ and R$^7$. By selecting the concentrations of the two dimers and choosing the R$^6$, R$^7$ and R$^8$ groups to be the same or different, one can tailor the concentration of the functional groups on the HCl-I molecule. FIG. 35 shows the reaction of the silsesquioxane half cube with two different difunctional silane dimers.

As with the trichlorosilanes, the difunctional silane dimers are further reacted with a second alcohol, R$^3$OH, in an alcoholysis step which may allow for the isolation, purification, or both of an intermediate compound and then reacting the this intermediate compound in an acid solution to remove the R$^3$OH and form Si—O—Si bridges, thus synthesizing the multifunctional silsesquioxane Instead of using a trichlorosilane or a difunctional silane dimer, it may be possible to also use a mixture which includes one or more trichlorosilanes and one or more difunctional silane dimers.

SQs may be hydrolyzed according to the teachings herein for forming functionalized mesoporous structures. For example, TGTSE, TCPTSE or another TSE systems may be hydrolyzed using acid or base catalysis with or without added Si(OEt)$_4$ in the presence of a structure directing organic such as plural or one of many alkylammonium salts known to be structure directing, then the products can be mesoporous silicate structures with the functional groups on the surfaces and within the pores of the resulting structure. These functional groups are available for further modification using the techniques used in the following examples.

The present invention is further illustrated, without limitation, by reference to the following examples.

Example 1

Synthesis of tetratriethoxysilylethyldimethylsiloxyocta silsesquioxane (TTSE)

OHS (50 g, 4.9 mmol) is dissolved in 350 mL of hexane. Then 42 mL (19 mmol) of vinyltriethoxysilane (VTES) and 0.3 g of Pt/C are added. The reaction mixture is stirred at reflux for 10 d. The catalyst is recovered for recycling and the solvent is evaporated with a rota-evaporator. The expected product is a transparent viscous liquid. FIG. 4 illustrates.

Figure 13:
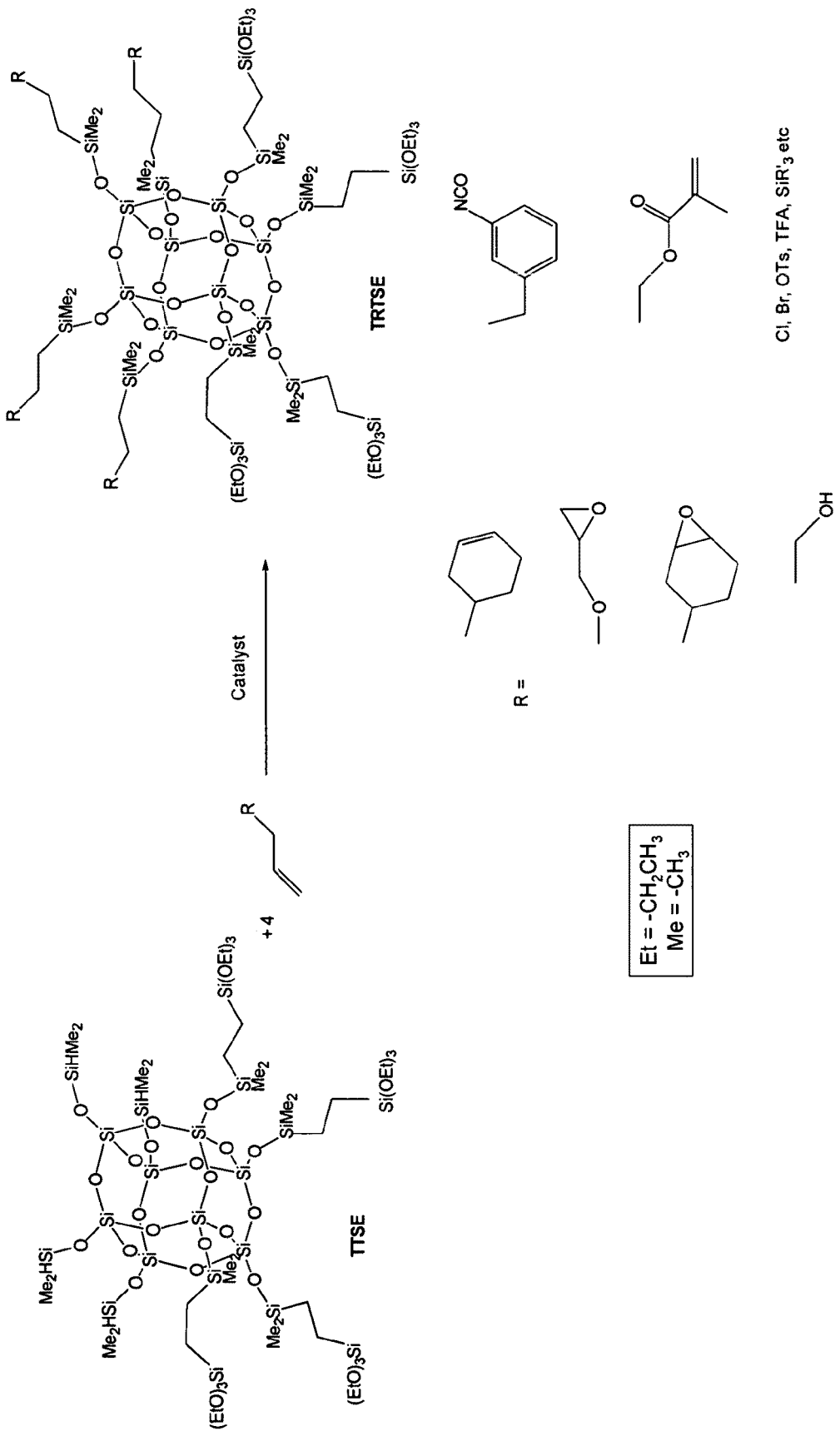
FIG. 13 illustrates an example of the hydrosilylation reaction of a multi-functional SQ (e.g. TTSE) with various vinyl molecules having a desired functional group to form a multi-functional SQ having the desired functional group (e.g. TRTSE).

FIG. 13 depicts other examples of functional groups that may be employed for preparing multi-functional SQs. The FIG. 13 illustrates the modification of TTSE by a reaction, such as in the presence of a catalyst for adding one or any combination of the functional groups depicted in FIG. 13. Such functional groups may be employed for the other disclosed SQs as well. Further, the functional groups shown in the various examples (e.g., those derived by reaction in the presence of catalyst) may be employed with other SQs.

Example 2

Synthesis of Tetracyclohexenyltetratriethoxysilylethane Cube (TCTSE)

TTSE (50 g, 28 mmol) is dissolved in 500 mL of hexane. Then 1-vinyl-4-cyclohexene (16 mL, 113 mmol) and 0.3 g Pt/C are added. The reaction mixture is stirred at reflux and followed by FTIR until the v Si—H peak at 2200 cm$^{-1}$ disappears. The product is obtained in 92% yield.

Example 3

Synthesis of TCPTSE as a Novel Bifunctional SQ

Figure 14:
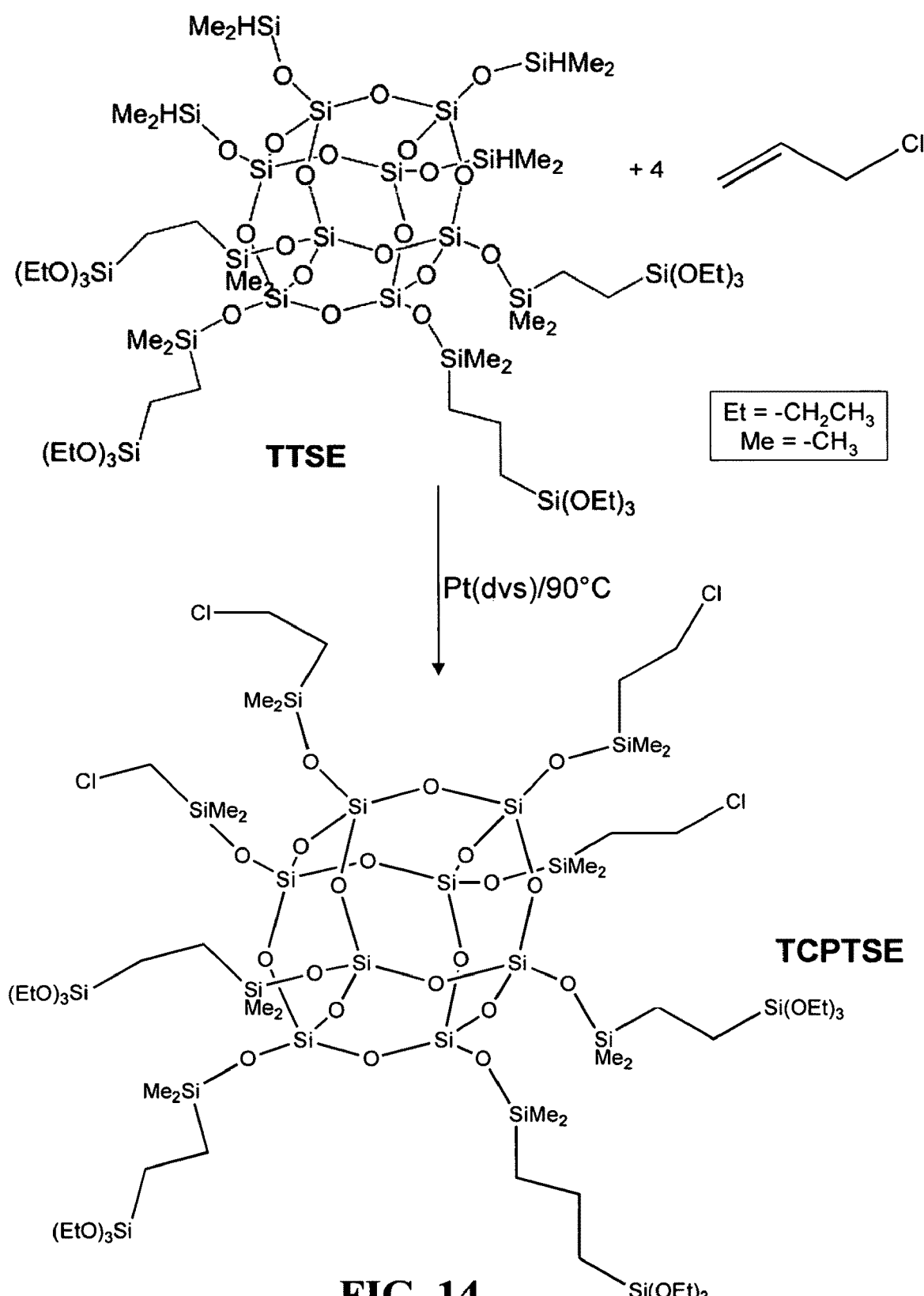
FIG. 14 illustrates an example of the preparation of a multi-functional SQ (e.g. a hexane functional SQ such as tetracyclohexenyltetratriethoxysilylethanesilsesquioxane cube (TCTSE)) by reacting a functional vinyl (e.g. 1-vinyl-4-cyclohexene) with a multi-functional SQ such as TTSE.

TTSE (25 g, 14 mmol) is dissolved in 250 mL of solvent. Then allyl chloride (6 mL, 56 mmol) and 0.1 g Pt/C are added. The reaction mixture is stirred at reflux for 2 days and followed by FTIR until the v Si—H peak 2200 cm$^{-1}$ disappears. The product is isolated by filtration and obtained in 85% yield. FIG. 14 illustrates the reaction.

Example 4

Tetraoxyethanolltetratriethoxysilylethane Cube (TOETSE)

Figure 15:
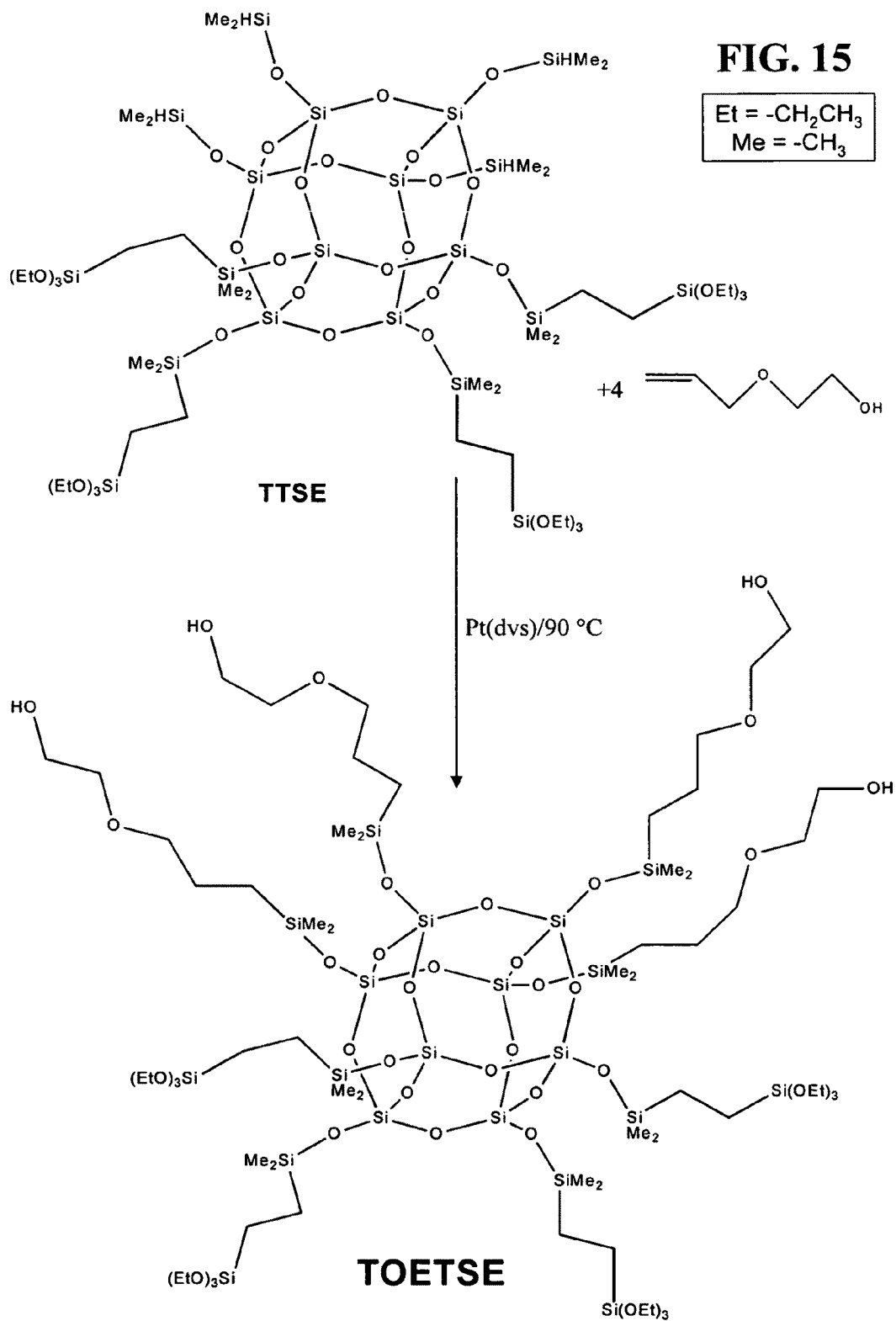
FIG. 15 illustrates an example of a SQ (e.g. a bifunctional SQ such as tetraoxyethanoltetratriethoxysilylethane cube (TOETSE)) having alcohol functionality (e.g. oxyethanol functionality).

TOETSE is prepared as shown in FIG. 15, and is another example of bifunctional cube with improved icephobic properties.

To produce TOETSE, which has an average of four highly crosslinkable triethoxysilyletane units and four propoxyethanol units TTSE is first produced, which is used as starting material to produce TOETSE. TTSE (25 g, 14 mmol) is dissolved in 350 mL of hexane. Then allyloxyethanol (7 mL, 56 mmol) and 0.2 g Pt/C are added. The reaction mixture is stirred at reflux for 6 days and followed by FTIR which show no v Si—H peak at 2200. The yield of TOETSE is 86%.

A coating is prepared. An amount of 6 g of the desired compound is added to 25 mL of 70% methanol 30% acetone solvent mixture and stirred for 30 min. Thereafter, 1 mL of an HCl/water solution (1 mL of 37% HCl to 99 mL water) is added and the solution is allowed to stir for about 10 minutes. Then the solution is applied by dip coating, spin casting, spraying, or any combination thereof ("Method A", which techniques may also be employed for any of the other coatings herein). For example, it can be sprayed using a Binks M1-G HVLP spray gun across the substrate at a pressure to a thickness of 0.1-0.5 mils (2.5-15 microns). A typical nozzle atomizing pressure is 6 psi.

An alternate method ("Method B") of applying coatings in the present example or for any of the other coatings herein is to use spin coating. An example of such an approach is described in "High Modulus Spin-On Organosilicates for Nanoporous Glasses," Adv. Mater., 19, 705-710, (2007), hereby incorporated by reference.

Example 5

Thin Dielectric Films from OTSE

Thin films made by spin coating are prepared using OTSE as the starting materials. The materials show excellent properties, including planarity and low porosity, such as in within about 15% of the values recited as shown in the following Table.

| RI | $ñ_{dry}$ (g/cc) | $ñ_{wall}$ g/cc | Porosity (%) | CTE (ppm/° C.) | Dielectric k |
|---|---|---|---|---|---|
| 1.313 | 1.298 | 1.362 | 4.75 | 29 | ≈2.8 |

Figure 16:
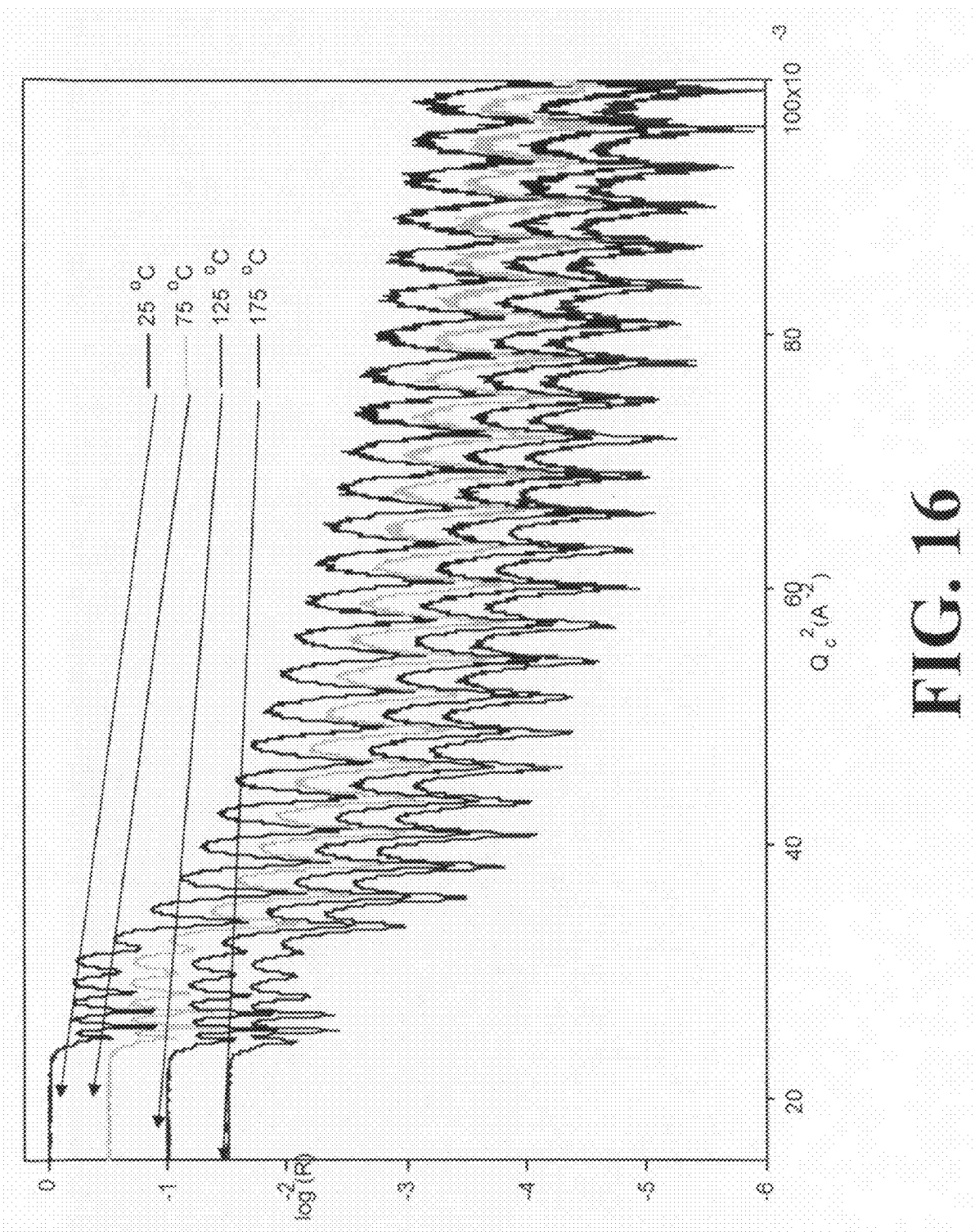
FIG. 16 illustrates an example of X-ray reflectivity of an SQ film (e.g. OTSE films) measured at 25° C., 75° C., 125° C., and 175° C., and demonstrates that a smooth layered structure having long range order is achievable in accordance with the present teachings.

In addition, these films are very smooth as demonstrated by the x-ray reflectivity measurements, in accordance with the teachings of "High Modulus Spin-On Organosilicates for Nanoporous Glasses," Adv. Mater. 19, 705-710, (2007), incorporated by reference. See, FIG. 16, depicting X-ray reflectivity of OTSE films on heating at different temperatures. See also, R. Q. Su, T. E. Müller, J. Prochazka, J. A. Lercher, "A New Type of Low-k Dielectric Films Based on Polysilsesquioxanes," Adv. Mater. 14, 1369-73 (2002), incorporated by reference.

Example 6

Low k Dielectric Films from TGTSE

By replacing about half of the $CH_2CH_2Si(OEt)_3$ groups of OTSE with an epoxy or other organic group, it is also believed possible to make very good films. The films may further include one or more pre-attached porogens (e.g. an organic component that decomposes leaving one or more pores) that will be uniformly distributed in the films and on decomposition make materials that have excellent mechanical properties with very much higher porosities and considerably lower dielectric constants, such as in within about 15% of the values recited in the following table.

| RI | $ñ_{dry}$ (g/cc) | $ñ_{wall}$ g/cc | Porosity (%) | CTE (ppm/° C.) | Dielectric k |
|---|---|---|---|---|---|
| 1.368 | 1.07 | 1.378 | 22.0 | — | ≈2.3 |

Figure 17:
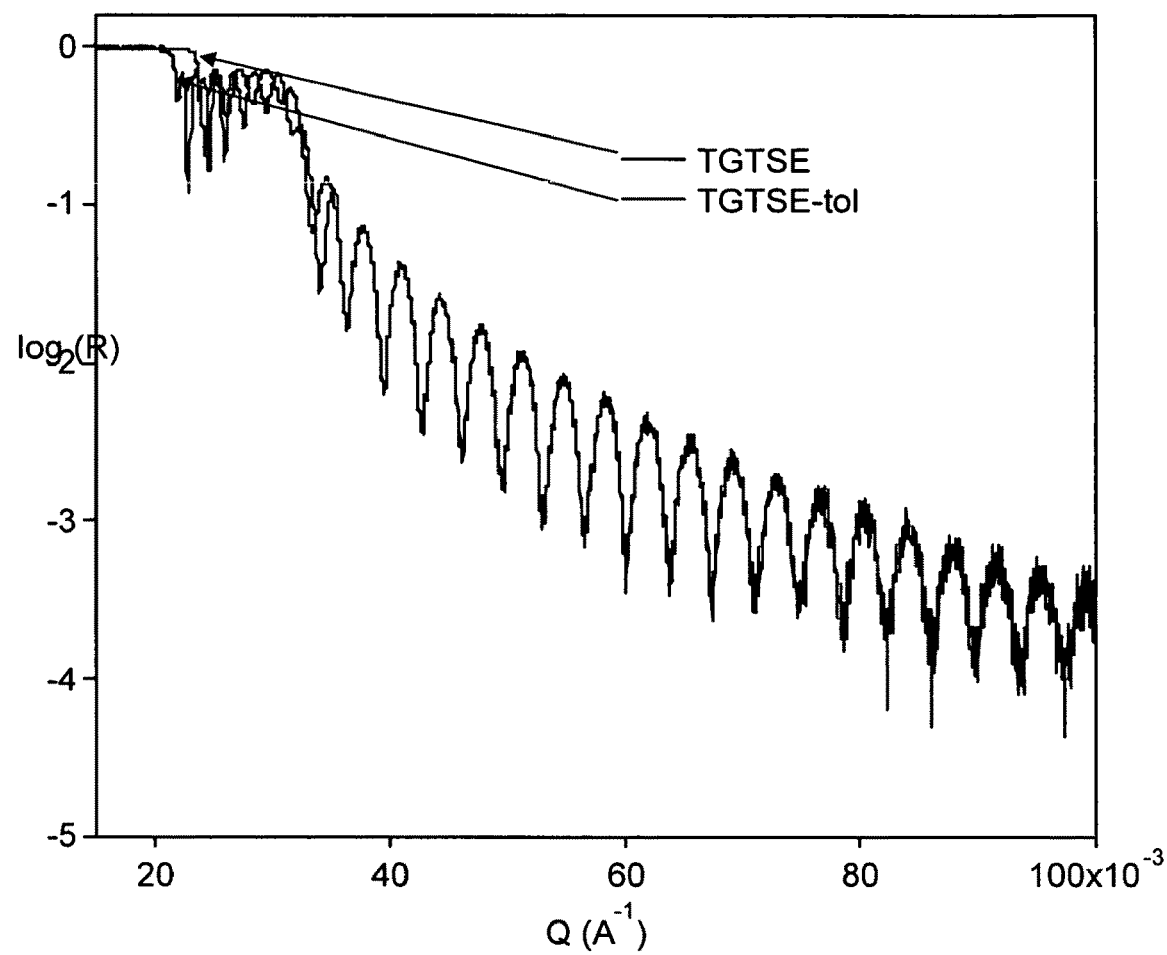
FIG. 17 illustrates an example of X-ray reflectivity of a multi-functional SQ film (e.g. TGTSE or an OTSE where some, and more specifically about half, of the triethoxysilylethyl groups are replaced with an epoxy or other organic group).

Furthermore, the length of the organic group can be modified to incorporate more organic to further lower the dielectric constant without sacrificing the excellent mechanical properties. Finally the film is also believed to be quite smooth and would exhibit characteristics such as shown in the x-ray reflectivity data of FIG. 17.

Example 7

An Example of a Coating Made with TCTSE Using Method A

FIGS. 18 a and b illustrate how wetting is believed to be modified by coating with TCTSE using Method A. Three water droplets are placed on each of the uncoated and coated Al surfaces. Upon close examination, the droplets on bare Al have a wetting angle of about 30±5° while the droplets on the TCTSE coated substrate have a wetting angle of about 80±5° as measured by ASTM D5946. The coating hardnesses after one week at room temperature is expected to be 1 to 2H, which is very hard for a spray-coated material. This is believed to be a significant improvement, and further optimization of the TCTSE coating may yield wetting angles great than this.

Example 8

Hardnesses of Coatings Made by Standard Method After Aging

The following table lists expected hardnesses of coatings made by standard method ASTM D3363 and their hardnesses after 7 days aging at room temperature.

| Coating material | Hardness |
|---|---|
| TCTSE | 6H |
| TGTSE | F |
| TOETSE | 5H |
| OTSE | 5H |
| TCPTSE | 2H |

Except for the epoxy terminated materials all of the other coatings are expected to be very hard with TCTSE being 6H after 7 days.

Example 9

Contact Angles of 7 Day Old Films

The following table lists expected contact angles for the coatings of Example 8, prepared by Method A, measured according to ASTM D5946.

| Coating material | Contact angles (° ± 2°) |
|---|---|
| TCTSE | 82 |
| TGTSE | 80 |
| TOETSE | 81 |
| OTSE | 79 |
| TCPTSE | 90 |

Example 10

Multilayer Films

Figure 19:
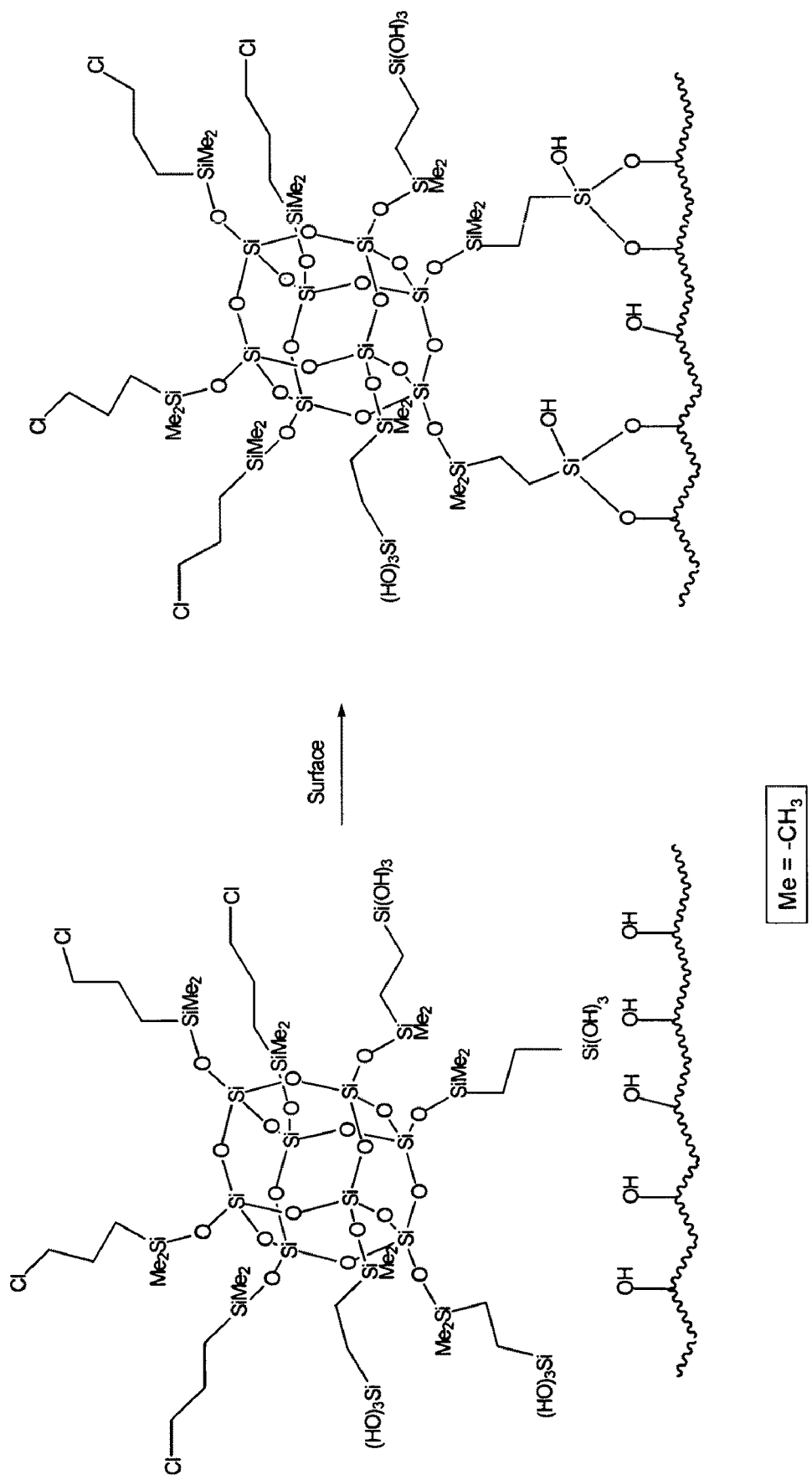
FIG. 19 illustrates an example of a reaction of a multi-functional SQ having Si—OH functionality one face (e.g. a silsesquioxane cube with four trialkoxysilyl functional groups and four other functional groups such as a chlorine containing group) with a functionalized surface, namely a surface having OH functionality.
Figure 20:
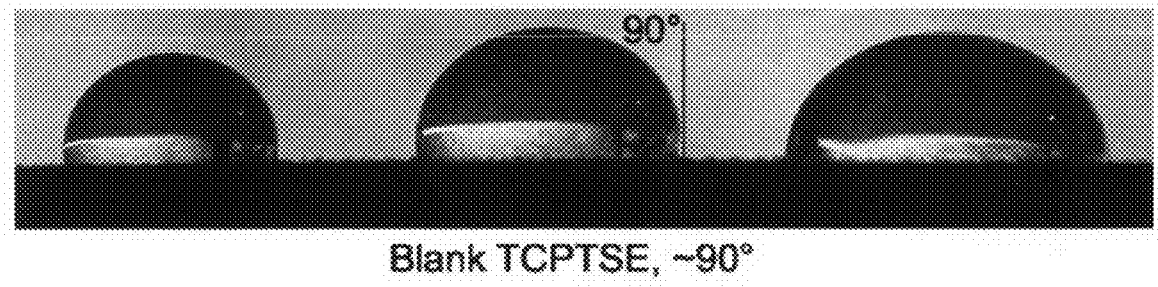
FIG. 20 illustrates a representative wetting of water on a surface coated with a SQ having a simple organic or inorganic nucleophile functional group (e.g. amines, thiols, carboxylates, and the like).
Figure 25:
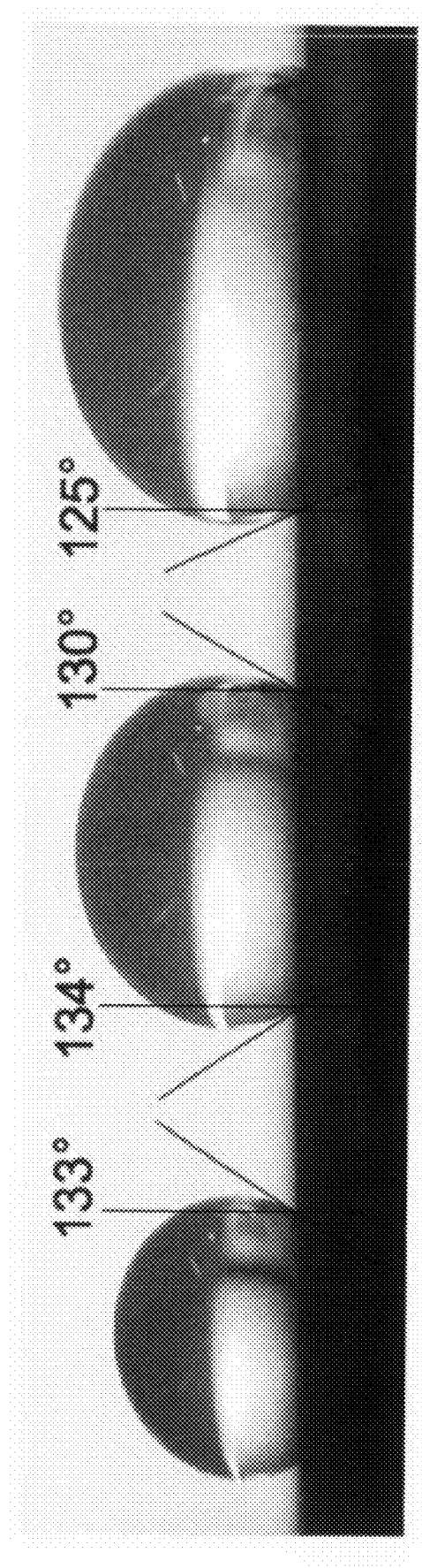
FIG. 25 illustrates the wetting of a surface coated with an SQ having a nucleophilic group (e.g. a surface first coated with TCPTSE and then with 2-methylaminoethanol).

TCPTSE derived films made on appropriate substrates can be modified as follows. After appropriate processing the films can be exposed to any simple organic or inorganic nucleophiles including but not limited to amines, thiols, carboxylates, or any combinations thereof. Strongly basic materials are possible also, but with potentially lower success. On brief exposure at a temperature designed to provide good reactivity, the surface becomes modified as suggested by the general reaction of FIG. 19. The approximate expected contact angles (e.g., within about 15°) for water droplets on coated surfaces are shown in FIG. 20. It is believed particularly beneficial to employ a reaction with N-methylaminoethanol, for providing a relatively high level of hydrophobicity. This is illustrated for example by reference to the FIGS. 25 and 26.

Another possible approach is to making a coating that is antibacterial. Alkyl ammonium salts even on silsesquioxanes are noted to offer antibactieral properties. Thus it is possible to make coatings where the second layer or other layer is antibacterial but abrasion and corrosion resistance is obtainable mainly from a different layer.

Example 11

Making Multilayers

Figure 21:
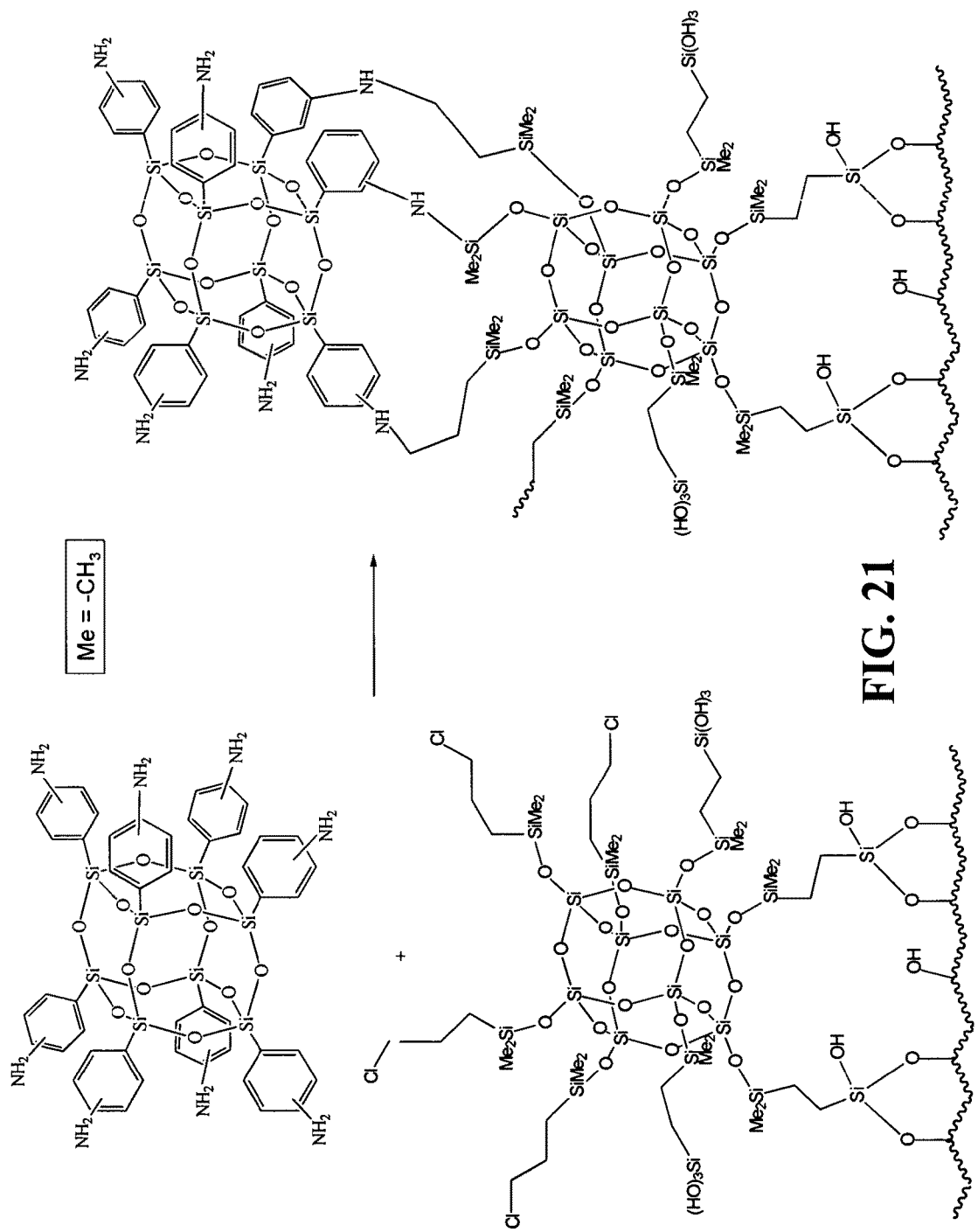
FIG. 21 illustrates the reaction of an SQ having a nucleophilic functional group (e.g. an SQ with amine functional groups, such as AOPS) to an SQ layer having exposed functionality which reacts with the nucleophilic group (e.g. having chlorine functionality exposed).
Figure 28:
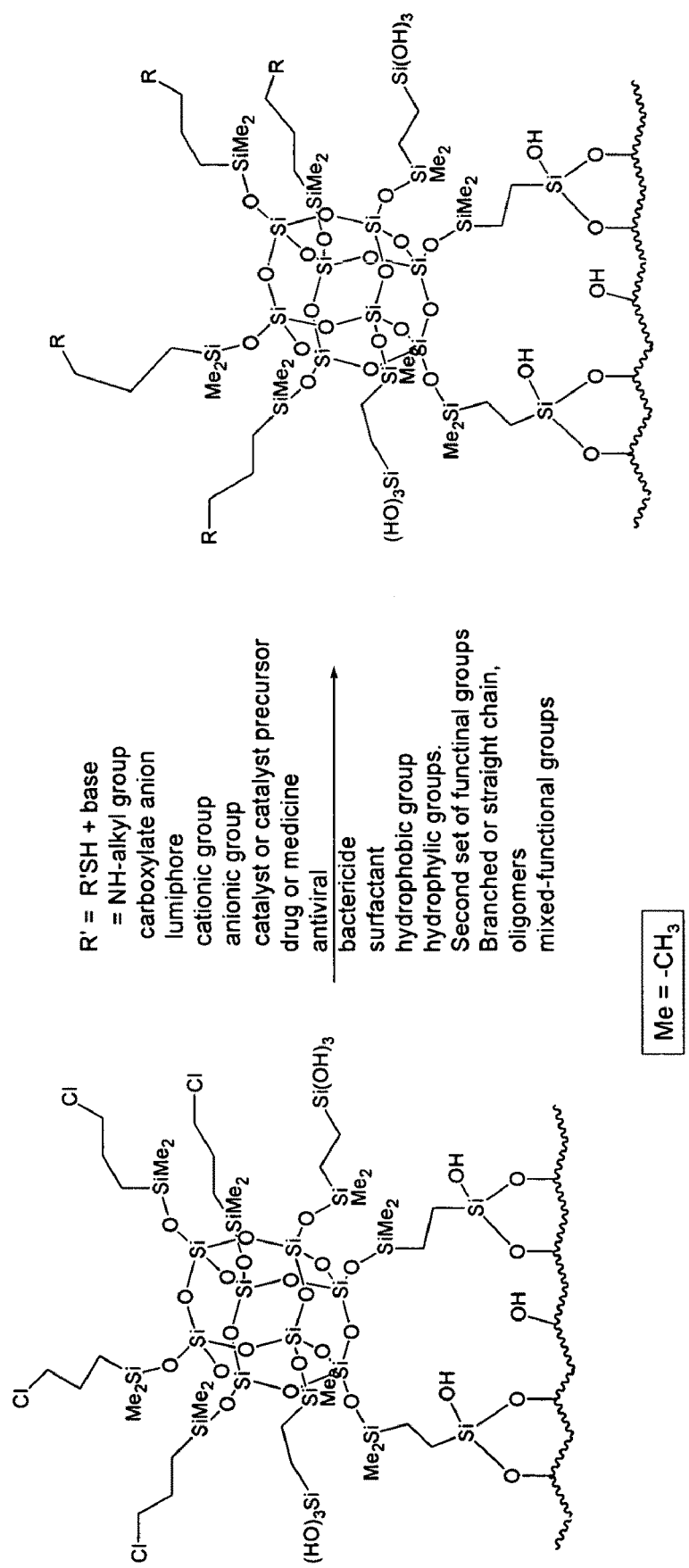
FIG. 28 illustrates an example of a reaction with a SQ surface layer having chlorine functionality where the new functional group on the SQ surface can have one or more of the a bactericide, surfactant, hydrophobic group, hydrophilic group, multiple functional group, branched oligomer, straight chain oligomer, mixed functional groups, antiviral, catalyst, catalyst precursor, anionic group, cationic group, drug, RSH, NH-alkyl group, carboxylate anion, lumiphore, or any combination.

Other multi-layer structures are possible according to the teachings herein, such as is illustrated in FIGS. 21, 27 and 28. Basically, FIG. 27 provides for surface modification with amines or any other mild nucleophile that in turn can be modified.

Example 12

Figure 22:
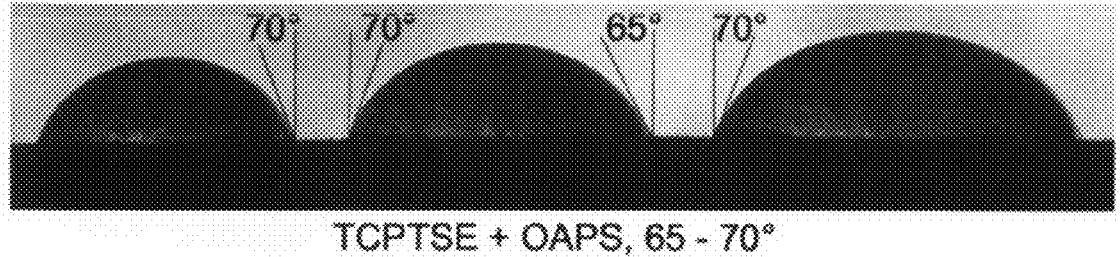
FIG. 22 illustrates the wetting of a surface coated with an SQ having a nucleophilic group where the wetting angle is less than 75° (e.g. a surface first coated with TCPTSE and then with OAPS).
Figure 23:
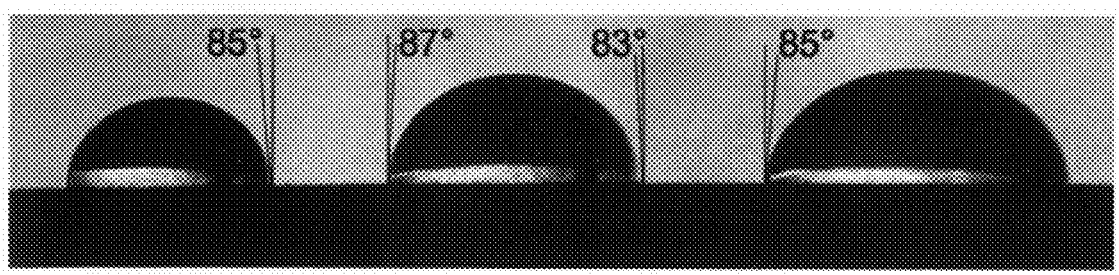
FIG. 23 illustrates the wetting of a surface coated with an SQ having a nucleophilic group where the wetting angle is greater than 75° (e.g. a surface first coated with TCPTSE and then with diaminodiphenylmethane).
Figure 29:
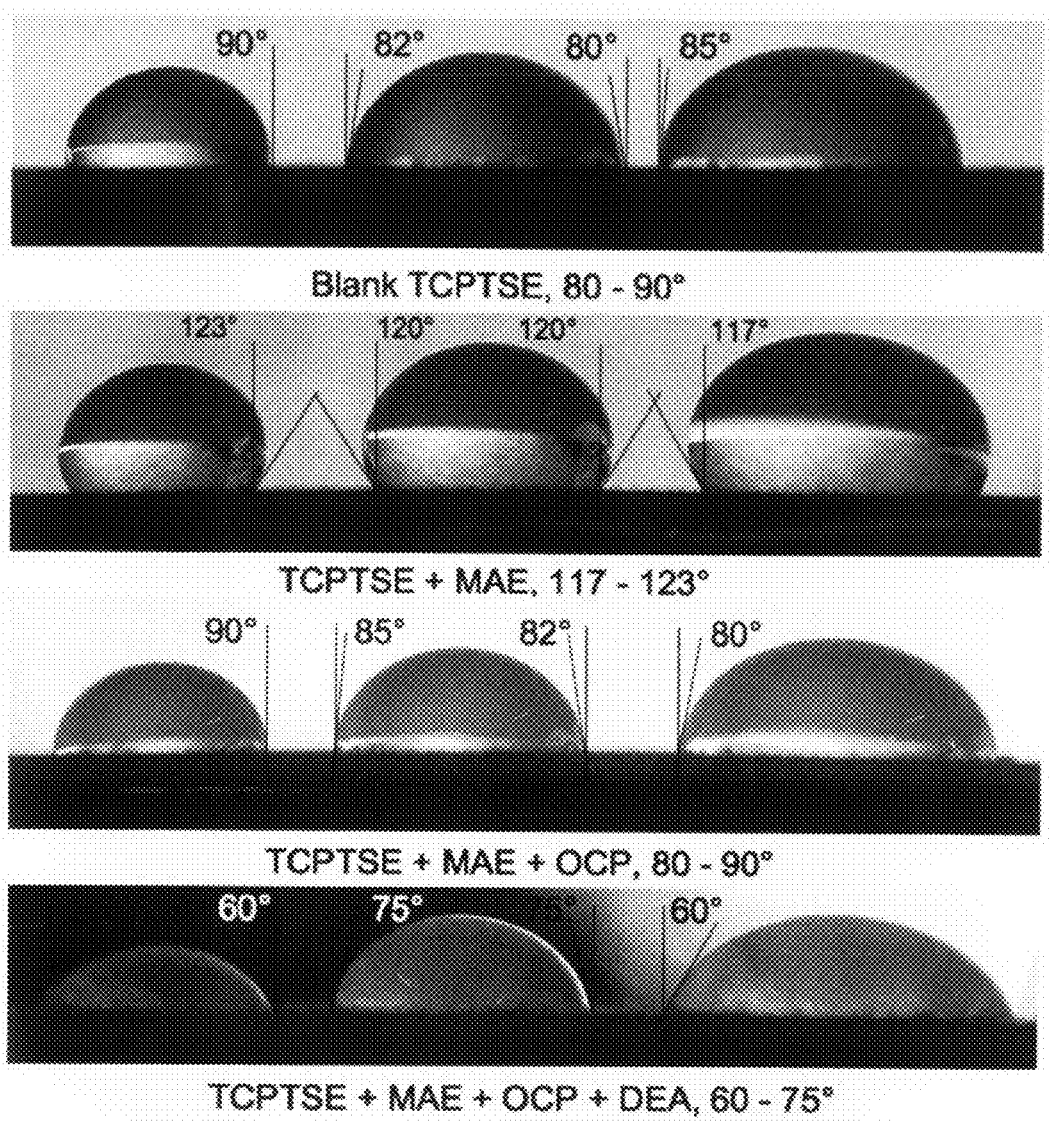
FIG. 29 illustrates that the contact angle of a liquid droplet be varied selectively (e.g. an increase or a decrease) by each distinct SQ layer added to a surface.

FIGS. 22, 23, and 29 illustrates the effect on contact angle believed possible depending upon selection of amine or other functional group for coatings. The surface used in the contact angle study in FIG. 22 is prepared according to a reaction as illustrated in FIG. 21.

Example 13

Multilayer Coatings

Figure 26:
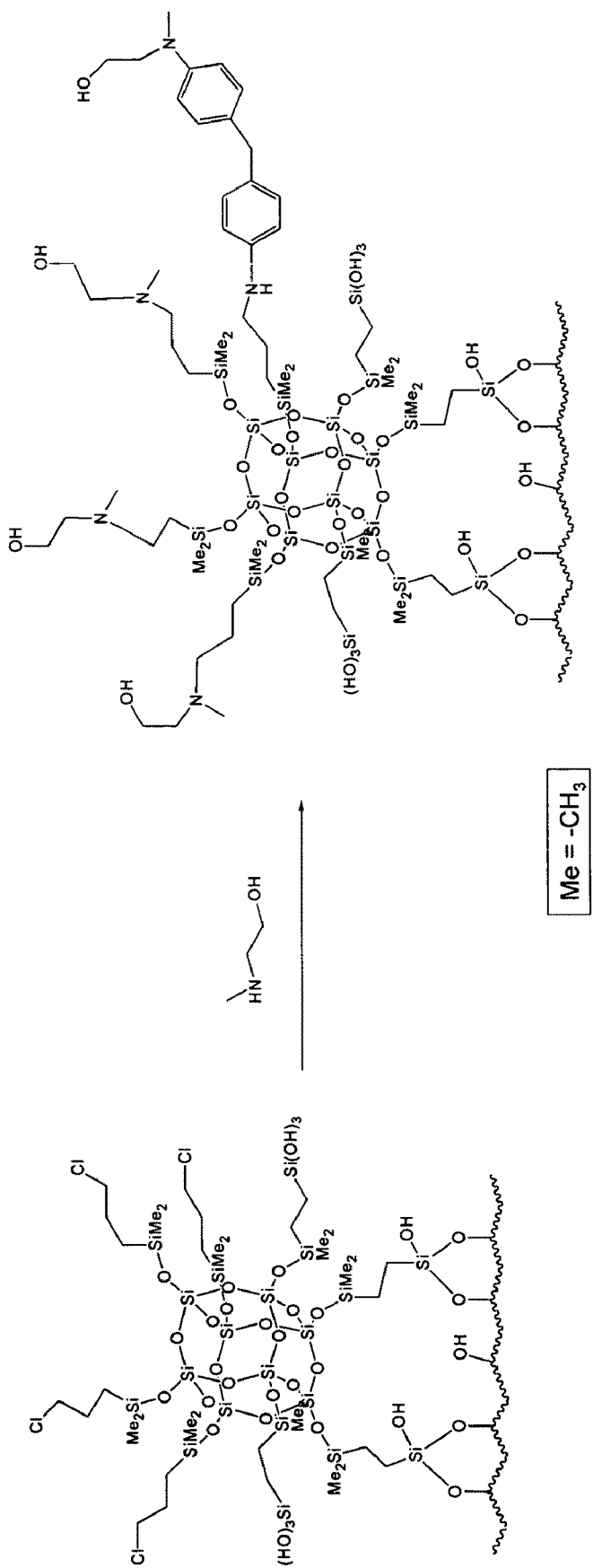
FIG. 26 illustrates an example of a reaction of a molecule having one nucleophilic group and one additional reactive group (e.g. 2-methylaminoethanol (MAE)) to a an SQ or an SQ layer having exposed functionality which reacts with the nucleophilic group (e.g. having chlorine functionality exposed).

Multilayer coatings are prepared as described in FIGS. 26-28.

In addition as noted above, second or additional layers can be added by either chemical reaction or through layer by layer build up of ionic species. It is also possible that metal nanoparticles can be trapped within layers. Metal complexes can also be trapped or added as mixed groups.

Example 14

Figure 24:
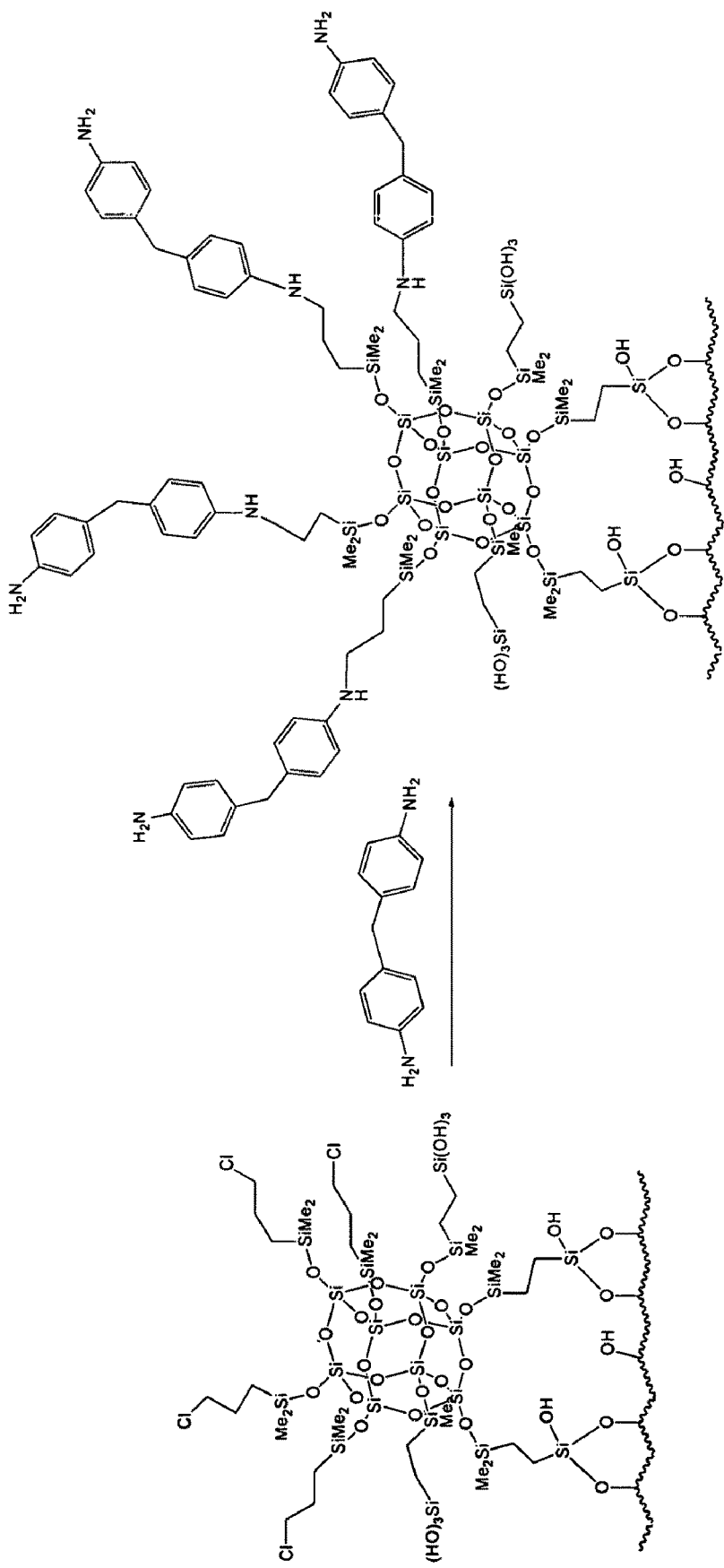
FIG. 24 illustrates an example of a reaction of a difunctional nucleophile (e.g. a diamine such as a diaminodiphenylmethane (DDM)) to a an SQ layer having exposed functionality which reacts with the nucleophilic group (e.g. having chlorine functionality exposed).
Figure 30:
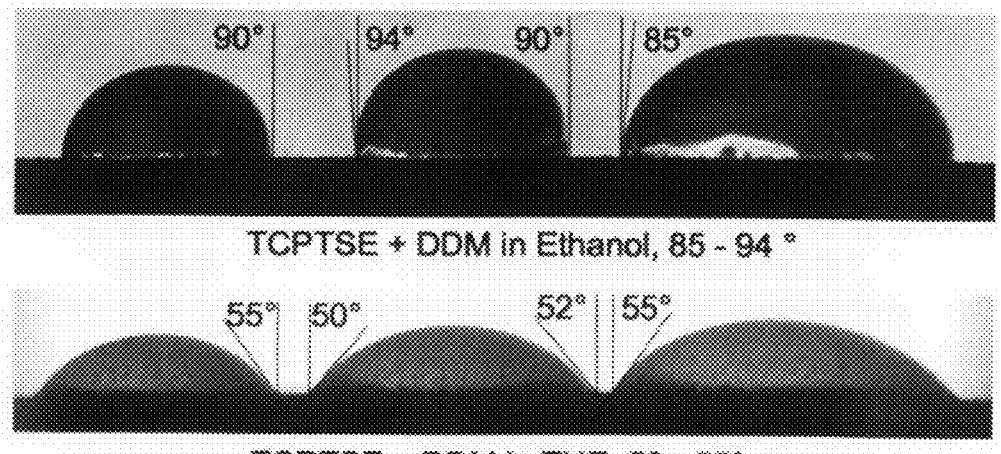
FIG. 30 illustrates the contact angles believed possible depending on the selection of an agent amine for coatings.

The effect on wetting (contact angles) of solvent selection for coatings is illustrated in the following table. Aluminum substrates are coated with TCPTSE and dip coated in solution including the specified amine (as shown for example by the reactions with TCPTSE illustrated in FIG. 24 and FIG. 26 for DDM and MAE respectively and by the wetting angles shown in FIG. 23 and FIG. 25 for DDM and MAE respectively) solvents of the table. FIG. 30 illustrates TCPTSE+DDM in Ethanol (top photo) and TCPTSE+DDM in THF (bottom photo). Bold and italics indicate hydrophilic. Asterisk(*) denotes hydrophobic.

It is thus seen that the teachings herein (i.e., the teachings generally, and not limited to this example) may employ a step of treating a surface (e.g., by contacting it with a coating herein, by reacting at least one of the functional groups of the coating herein with a further compound, or both) for making the surface more hydrophilic or hydrophobic.

|  | Acetone | Ethanol | THF |
| --- | --- | --- | --- |
| EA | 90-110 | 98-105 | 90-105 |
| DEA | 50-57* | 70-85 | 55-65* |
| TEA | 83-90 | 82-85 | 75-80 |
| MAE | 110-130 | 110-125 | 105-115 |
| DDM | 78-87 | 85-95 | 50-60* |
| OAPS | 72-75 | 65-85 | 75-90 |

Example 15

Ph$_4$ Half Cube or Tetraanion Sodium Salt

To a dry 1000 mL round bottom flask under N$_2$ and equipped with a magnetic stir bar and reflux condenser is added about 20.00 g (19.36 mmol) of octaphenylsilsesquioxane, about 6.84 g (170.4 mmol) of NaOH, and about 500 mL of n-butanol. The mixture is heated at reflux for about 24 to about 48 hours. The insoluble solids is filtered from the hot solution and the filtrate is cooled to room temperature and placed overnight in a freezer to give a white crystalline solid. The solid is filtered and dried in vacuo at about 65° C. for about 12 h to give about 22.84 g (92%) of tetraanion sodium salt.

Example 16

Me$_4$Ph$_4$ Alkoxy and Me$_4$Ph$_4$[Si O$_{12}$]

To a dry 500 mL round bottom flask under N$_2$ and equipped with a magnetic stir bar is added a suspension of about 5.00 g (8.2 mmol) of Ph$_4$ half cube sodium salt in about 100 mL of methanol. About 4.25 mL (36.2 mmol) of methyltrichlorosilane in about 100 mL of hexane is added via an addition funnel over about 30 minutes with vigorous stirring. The resulting heterogeneous mixture is stirred at about 25° C. for about 24 hours. The insoluble solids are filtered for separation of the organic phase and is then dried over Na$_2$SO$_4$. Rotary evaporation yields a viscous yellow oil. The oil is dried in vacuo for about 5 hours, giving about 6.92 g (87%). About 0.500 g (0.52 mmol) of the Me$_4$Ph$_4$ derivative is dissolved in about 10 mL of hexane and is added to about 1.5 mL of 37% HCl in about 10 mL of H$_2$O. The mixture is stirred at ambient temperature for about 24 hours to give a white, powdery solid. The solid is filtered and dried in vacuo at about 60° C. for about 8 hours to give about 0.284 g (70%) of Me$_4$Ph$_4$[Si$_8$O$_{12}$]. The thermogravimetric analysis (TGA) of the Me$_4$Ph$_4$[Si$_8$O$_{12}$] is performed in air, e.g. at a rate of about 10° C./min from about 25° C. to about 980° C. in air to burn off the carbon, leaving SiO$_2$. A SiO$_2$ yield of 61.23% is measured. The theoretical yield is 61.21%. The TGA curve of this Me$_4$Ph$_4$[Si$_8$O$_{12}$] sample is given in FIG. 36a where the ratio of the sample weight to the initial sample weight is plotted as a function of temperature. The FTIR curve for this Me$_4$Ph$_4$[Si$_8$O$_{12}$] sample is given in FIG. 37b.

Example 17

Vinyl$_4$Ph$_4$ Alkoxy Derivative and Vinyl$_4$Ph$_4$[Si$_8$O$_{12}$]

To a dry 500 mL round bottom flask under N$_2$ and equipped with a magnetic stir bar is added a suspension of about 5.00 g (8.2 mmol) of Ph$_4$ half cube sodium salt in about 100 mL of methanol. About 4.60 mL (36.2 mmol) of vinyltrichlorosilane in about 100 mL of hexane is added via an addition funnel over about 30 minutes with vigorous stirring. The resulting heterogeneous mixture is stirred at a temperature of about 25° C. for about 24 hours. The insoluble solids are filtered and separation of the methanol layer is followed by drying over Na$_2$SO$_4$ and rotary evaporation. The product is the vinyl$_4$Ph$_4$ alkoxy derivative, which is a white crystalline solid. The solid is dried in vacuo for about 5 hours. Thus dried, the solid weighs about 7.33 g (a yield of about 88%). Then, about 0.500 g (0.49 mmol) of the Vinyl$_4$Ph$_4$ alkoxy derivative is dissolved in about 10 mL of methanol and added to about 1.5 mL of 37% HCl in about 10 mL of H$_2$O. The mixture is stirred at ambient temperature for about 24 hours to give a white, powdery solid. The solid is filtered and dried in vacuo at about 60° C. for about 8 hours to give about 0.331 g (80%) of Vinyl$_4$Ph$_4$[Si$_8$O$_{12}$].

The FTIR spectra of the Vinyl$_4$Ph$_4$[Si$_8$O$_{12}$] sample is given in FIG. 37a. The molecular weight of the reaction product is determined by MALDI as shown in FIG. 37b, where the Vinyl$_4$Ph$_4$[Si$_8$O$_{12}$] sample has a molecular weight near the expected MW=941 Da.

Example 18 iBu$_4$Ph$_4$ Alkoxy Derivative and iBu$_4$Ph$_4$[Si$_8$O$_{12}$]

To a dry 500 mL round bottom flask under N$_2$ and equipped with a magnetic stir bar is added a suspension of about 5.00 g (8.2 mmol) of tetraanion sodium salt in about 100 mL of methanol. Then about 5.97 mL (36.2 mmol) of i-butyltrichlorosilane in about 100 mL of hexane is added via an addition funnel over about 30 minutes with vigorous stirring. The resulting heterogeneous mixture is stirred at about 25° C. for about 24 hours. The insoluble solids are filtered and the separation of the organic phase is followed by drying over Na$_2$SO$_4$ and rotary evaporation. The process yields a viscous yellow oil which is the alkoxy derivative. The oil is dried in vacuo for about 5 hours, and the mass is about 7.46 g (80%). Then about 0.500 g (0.44 mmol) of the iBu$_4$Ph$_4$(OR)$_x$ derivative is dissolved in about 10 mL of hexane and added to about 1.5 mL of 37% HCl in about 10 mL of H$_2$O. The mixture is stirred at ambient temperature for about 24 hours to give a white, powdery solid. The solid is filtered and dried in vacuo at about 60° C. for about 8 hours to give about 0.335 g (80%) of iBu$_4$Ph$_4$-[Si$_8$O$_{12}$].

The molecular weight of the reaction product is determined by MALDI as shown in FIG. 38, where the iBu$_4$Ph$_4$[Si$_8$O$_{12}$] sample has a molecular weight near the expected MW=1061 Da.

Example 19

Octyl$_4$Ph$_4$ Alkoxy Derivative and Octyl$_4$Ph$_4$[Si$_8$O$_{12}$]

To a dry 500 mL round bottom flask under N$_2$ and equipped with a magnetic stir bar is added a suspension of about 5.00 g (8.2 mmol) of Ph$_4$ half cube sodium salt in about 100 mL of methanol. Then about 8.34 mL (36.2 mmol) of n-octyltrichlorosilane in 100 mL of hexane is added via an addition funnel over about 30 minutes with vigorous stirring. The resulting heterogeneous mixture is stirred at about 25° C. for about 24 hours. The insoluble solids are filtered and the separation of the organic phase followed by drying over Na$_2$SO$_4$ and rotary evaporation yields a viscous yellow oil, the alkoxy derivative. The oil is dried in vacuo for about 5 hours, giving about 8.05 g (72%). About 0.500 g (0.37 mmol) of the Octyl$_4$Ph$_4$(OR)$_4$ derivative (or the Octyl$_4$Ph$_4$(OR)$_x$Cl$_{4-x}$ derivative, where x is 4 or less, and x may be less than about 1) is dissolved in about 10 mL of hexane and added to about 1.5 mL of 37% HCl in about 10 mL of H$_2$O. The mixture is stirred at ambient temperature for about 24 hours to give a white, powdery solid. The solid is filtered and dried in vacuo at about 60° C. for about 8 hours to give about 0.281 g (65%) of Octyl$_4$Ph$_4$[Si$_8$O$_{12}$]. The molecular weight of the reaction product is determined by MALDI as shown in FIG. 39, where the Octyl$_4$Ph$_4$[Si$_8$O$_{12}$] sample has a molecular weight near the expected MW=1285 Da.

Example 20

(ClCH$_2$)$_4$Ph$_4$ alkoxy derivative and (ClCH$_2$)$_4$Ph$_4$ [Si$_8$O$_{12}$]

To a dry 500 mL round bottom flask under N$_2$ and equipped with a magnetic stir bar is added a suspension of about 5.00 g (8.2 mmol) of Ph$_4$ half cube sodium salt in about 100 mL of methanol. About 4.54 mL (36.2 mmol) of chloromethyltrichlorosilane in about 100 mL of hexane is added via an addition funnel over about 30 minutes with vigorous stirring. The resulting heterogeneous mixture is stirred at about 25° C. for about 24 hours. The insoluble solids are filtered off and the organic phase is separated and dried over Na$_2$SO$_4$. Following rotary evaporation, a viscous yellow oil of the alkoxy derivative is obtained. The oil is dried in vacuo for about 5 hours, giving about 6.81 g (75%). Then about 0.500 g (0.45 mmol) of the (ClCH$_2$)$_4$Ph$_4$ alkoxy derivative is dissolved in about 10 mL of hexane and added to about 1.5 mL of 37% HCl in about 10 mL of H$_2$O. The mixture is stirred at ambient temperature for about 24 hours to give a white, powdery solid. The solid is filtered and dried in vacuo at about 60° C. for about 8 hours to give about 0.317 g (76%) of (ClCH$_2$)$_4$Ph$_4$[Si$_8$O$_{12}$].

The molecular weight of the reaction product is determined by MALDI as shown in FIG. 40, where the (ClCH$_2$)$_4$Ph$_4$ [Si$_8$O$_{12}$] sample has a molecular weight near the expected MW=1031 Da.

Measurements may be made using art-disclosed techniques. For example, unless stated otherwise, contact angle measurements are per ASTM D5946, hardness is by pencil hardness testing (per ASTM D3363), refractive index is per ASTM D542, and dielectric constant is ASTM D150. Porosity may be measured per ASTM D6583-04. CTE may be measured by ASTM D-696.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter. The scope of the invention should, therefore, be determined not with reference to the above description, but should instead be determined with reference to the appended claims, along with the full scope of equivalents to which such claims are entitled. Properties recited herein for examples are approximate and amounts recited may vary (e.g., within about 20% of the stated values). Recitation in the Examples of one specific SQ is not intended as foreclosing the use of other SQs. Thus, it is possible to employ TTSE, TCTSE, TCPTSE, TOETSE, OTSE, TGTSE, OCPTSE, or any combination thereof, in place or in addition to the SQ recited in the Examples.

What is claimed is:

1. A multi-functional silsesquioxane, comprising:
  a. a polyhedral silsesquioxane including at least one first face and at least one second face that is spaced apart from the at least one first face;
  b. at least one first functionality bonded to the at least one first face; and
  c. at least one second functionality different from the first functionality, and being bonded to the at least one second face, with the at least one first functionality being adapted for bonding to a surface, another silsesquioxane, an organic functional group, or any combination thereof;
  wherein the polyhedral silsesquioxane is generally cubic, is generally octahedral, or a combination thereof;
  wherein silicon is positioned in each corner of the generally cubic structure;
  wherein the multi-functional silsesquioxane is selected from (tetratriethoxysilylethyldimethyl siloxy)(tetrahydridodimethylsiloxy)octasilsesquioxane, tetracyclohexenyltetratriethoxysilylethylsilsesquioxane, tetratriethoxysilylethyldimethylsiloxy)(tetra-3-chloropropyldimethylsiloxy)octasilsesquioxane, (tetraoxyethanolethyldimethylsiloxyl)tetratriethoxysilylethylsilsesquioxane, (tetratriethoxysilylethyldimethylsiloxy)(tetraglycidyldimethylsiloxy)octasilsesquioxane, or any combination thereof.

2. The multi-functional silsesquioxane of claim 1, wherein the silica of the silsesquioxane is derived from rice hull ash via an octa(tetramethylammonium)silsesquioxane octaanion.

3. The multi-functional silsesquioxane of claim 1, wherein the multi-functional silsesquioxane is bonded to a surface selected from a plastic, metal, ceramic, carbon, a composite of any of the foregoing, or any combination thereof.

4. The multi-functional silsesquioxane of claim 3, wherein the multi-functional silsesquioxane is bonded to the surface by way of a Si—OH group.

5. The multi-functional silsesquioxane of claim 3 wherein the multi-functional silsesquioxane is a porous structure.

6. The multi-functional silsesquioxane of claim 1, wherein the multi-functional silsesquioxane has a dielectric constant of about 1 to about 4.

7. An article including the multi-functional silsesquioxane of claim 1.

8. The article of claim 7, wherein the multi-functional silsesquioxane is a coating.

9. The article of claim 8, wherein the coating exhibits a wetting angle of water of at least about 75°.

10. The article of claim 7 wherein the multi-functional silsesquioxane is bonded to a substrate selected from metal, ceramic, carbon, a composite of any of the foregoing, or any combination thereof, via at least two SiOH groups of the at least one first functionality.

11. The article of claim 7, further comprising nanoparticles trapped within the space defined between either or both of the substrate and the multi-functional silsesquioxane or the multi-functional silsesquioxane and the at least one outer layer.

12. The article of claim 7, wherein the at least one outer layer includes a plurality of layers.

13. A method for making a multi-functional silsesquioxane coating, comprising the steps of:
  a. providing at least one source of silica;
  b. reacting at least a portion of the silica for forming a polyhedral cage that includes silicon at its corners, and for defining at least one first face and at least one second face spaced apart from the at least one first face;
  c. bonding at least one first functional group to the at least one first face;
  d. bonding at least one second functional group to the at least one second face, so that a multi-functional silsesquioxane of claim 1 is formed; and
  e. bonding the first functional group to a substrate via a Si—OH functionality for defining a first multi-functional silsesquioxane coating on the substrate.

14. The method of claim 13, wherein the bonding step (c) includes bonding at least three of the first functional group to the at least one first face.

15. The method of claim 13, wherein the bonding step (d) includes bonding at least three of the second functional group to the at least one second face.

16. The method of claim 13, wherein the coating is applied to the substrate in the presence of an amine-functional agent, wherein the amine-functional agent is selected from EA, DEA, TEA, MAE, DDM, OAPS or any combination thereof.

* * * * *